(12) United States Patent
Landegren et al.

(10) Patent No.: US 10,174,366 B2
(45) Date of Patent: Jan. 8, 2019

(54) LOCALISED RCA-BASED AMPLIFICATION METHOD

(71) Applicant: Olink AB, Uppsala (SE)

(72) Inventors: Ulf Landegren, Uppsala (SE); Lei Chen, Yangzhou (CN); Di Wu, Uppsala (SE); Yuan Nong, Nanning (CN); Caroline Gallant, Uppsala (SE)

(73) Assignee: OLINK BIOSCIENCE AB, Uppsala (SE)

( * ) Notice: Subject to any disclaimer, the term of this patent is extended or adjusted under 35 U.S.C. 154(b) by 0 days.

(21) Appl. No.: 14/442,701

(22) PCT Filed: Nov. 14, 2013

(86) PCT No.: PCT/EP2013/073880
§ 371 (c)(1),
(2) Date: May 13, 2015

(87) PCT Pub. No.: WO2014/076209
PCT Pub. Date: May 22, 2014

(65) Prior Publication Data
US 2016/0376642 A1    Dec. 29, 2016

(30) Foreign Application Priority Data

Nov. 14, 2012   (GB) .................................. 1220503.5
May 23, 2013   (GB) .................................. 1309327.3

(51) Int. Cl.
| | | |
|---|---|---|
| C12Q 1/68 | (2018.01) | |
| C12Q 1/6848 | (2018.01) | |
| C12Q 1/6804 | (2018.01) | |
| C12Q 1/682 | (2018.01) | |

(52) U.S. Cl.
CPC .......... *C12Q 1/6848* (2013.01); *C12Q 1/682* (2013.01); *C12Q 1/6804* (2013.01)

(58) Field of Classification Search
CPC ..................................................... C12Q 1/68
See application file for complete search history.

(56) References Cited

U.S. PATENT DOCUMENTS

| | | | |
|---|---|---|---|
| 5,854,033 A | 12/1998 | Lizardi | |
| 6,291,187 B1 | 9/2001 | Kingsmore et al. | |
| 6,596,486 B2 | 7/2003 | Frank-Kamenetskii et al. | |
| 6,610,481 B2 | 8/2003 | Koch | |
| 6,686,157 B2 | 2/2004 | Ward et al. | |
| 6,867,028 B2 | 3/2005 | Janulaitis et al. | |
| 7,320,860 B2 | 1/2008 | Landegren et al. | |
| 2001/0041340 A1* | 11/2001 | Kingsmore | C12Q 1/6804 435/6.12 |
| 2002/0192649 A1* | 12/2002 | Lizardi | C12Q 1/6804 435/6.12 |
| 2002/0192658 A1* | 12/2002 | Ward | C12Q 1/6816 435/6.1 |
| 2003/0059786 A1* | 3/2003 | Ward | C12Q 1/6816 435/6.12 |
| 2004/0248103 A1 | 12/2004 | Feaver et al. | |
| 2005/0069939 A1* | 3/2005 | Wang | C12N 15/1096 435/6.11 |
| 2005/0118616 A1* | 6/2005 | Kawashima | C12Q 1/682 435/6.12 |
| 2005/0186590 A1* | 8/2005 | Crothers | C12Q 1/682 435/6.11 |
| 2009/0233277 A1 | 9/2009 | Murakami | |
| 2014/0170654 A1* | 6/2014 | Landegren | C12Q 1/6816 435/6.11 |

FOREIGN PATENT DOCUMENTS

| | | |
|---|---|---|
| WO | 92/01813 A1 | 2/1992 |
| WO | 97/19193 A2 | 5/1997 |

(Continued)

OTHER PUBLICATIONS

Weibrecht et al. (Visualising individual sequence-specific protein-DNA interactions in situ, N Biotechnol. Jun. 15, 2012;29(5):589-98. doi: 10.1016/j.nbt.2011.08.002. Epub Aug. 31, 2011).*
Weibrecht et al: "Visualising individual sequence-specific protein-DNA interactions in situ", New Biotechnology, 29(5):589-598 (Jun. 2012).
Nong, "Proximity Ligation Assays for Disease Biomarkers Analysis", Acta Universitatis Upsaliensis, Oct. 7, 2011.
Thomas et al, "Amplification of Padlock Probes for DNA Diagnostics by Cascade Rolling Circle Amplification or the Polymerase Chain Reaction", Archives of Pathology & Laboratory Medicine, 123(12): 1170-1176 (1999).

(Continued)

*Primary Examiner* — Aaron A Priest
(74) *Attorney, Agent, or Firm* — Porter Wright Morris & Arthur LLP

(57) ABSTRACT

The present invention provides a method for performing a localised RCA reaction comprising at least two rounds of RCA, wherein the product of a second RCA reaction is attached, and hence localised, to a product of a first RCA reaction, said method comprising: (a) providing a first RCA product; (b) directly or indirectly hybridising to said first RCA product a probe which comprises or provides a primer for a second RCA reaction; and (c) performing a second RCA reaction using said RCA primer of (b) to form a second RCA product, wherein in said reaction: (i) said probe and said primer are not able to prime extension using said first RCA product as template or any such extension is limited to avoid displacement of any probe hybridised to the first RCA product; (ii) the direct or indirect hybridisation of the RCA primer of (b) to the first RCA product is maintained and, by virtue of said hybridisation, the second RCA product is attached to the first RCA product; (iii) a RCA template for said second RCA reaction is comprised in or provided by the probe, or is separately provided. The method finds particular utility in the detection of analytes, wherein the analyte is a nucleic acid or wherein a nucleic acid is used or generated as a marker for the analyte.

33 Claims, 25 Drawing Sheets
Specification includes a Sequence Listing.

(56) References Cited

FOREIGN PATENT DOCUMENTS

| | | | |
|---|---|---|---|
| WO | 97/20948 | A1 | 6/1997 |
| WO | 99/49079 | A1 | 9/1999 |
| WO | 01/61037 | A1 | 8/2001 |
| WO | 01/88190 | A2 | 11/2001 |
| WO | 03/012119 | A2 | 2/2003 |
| WO | 2004/094456 | A2 | 11/2004 |
| WO | 2005/047474 | A2 | 5/2005 |
| WO | 2005/111236 | A1 | 11/2005 |
| WO | 2006/020515 | A1 | 2/2006 |
| WO | 2006/108422 | A2 | 10/2006 |
| WO | 2007/005649 | A2 | 1/2007 |
| WO | 2009/037659 | A2 | 3/2009 |
| WO | 2012/049316 | A1 | 4/2012 |
| WO | 2012/152942 | A1 | 11/2012 |

OTHER PUBLICATIONS

Söderberg et al, "Direct observation of individual endogenous protein complexes in situ by proximity ligation", Nature Methods, 3(12): 995-1000 (2006).

Weibrecht et al., Proximity ligation assays: a recent addition to the proteomics toolbox, Expert Rev. Proteomics, 7(3), 401-409 (2010).

Kuhn et al., Rolling-circle amplification under topological constraints, Nucleic Acids Research, 30(2):574-580 (2002).

Dean et al., Rapid Amplification of Plasmid and Phage DNA Using Phi29 DNA Polymerase and Multiply-Primed Rolling Circle Amplification, Genome Research, 11:1095-1099 (2001).

Goransson, et al., A single molecule array for digital targeted molecular analyses, Nucleic Acids Research, 37(1):1-9 (2009, online Nov. 25, 2008).

Lizardi et al., Mutation detection and single-molecule counting using isothermal rolling-circle amplification, Nature Genetics, 19:225-232 (1998).

Olasagasti et al., Replication of individual DNA molecules under electronic control using a protein nanopore, Nature Nanotechnology, 5:798-806 (Nov. 2010, online Sep. 26, 2010).

Rashid, Blocking Oligomer Design Update (Mar. 2010-Mar. 2011), University of California, Department of Biomolecular Engineering, Nanopore Lab, p. 1-20 (2011).

Walby et al., Sequential Immunofluorescence Staining and Image Analysis for Detection of Large Numbers of Antigens in Individual Cell Nuclei, Cytometry 47:32-41 (2002).

\* cited by examiner

A

B

A

B

LOCALISED RCA-BASED AMPLIFICATION METHOD

The present invention lies generally in the field of nucleic acid amplification by rolling circle amplification (RCA), and particularly in the concept of generating a localised, more than linear, amplification based on RCA in at least two rounds of amplification. The product of the second (or further) RCA reaction is not physically derived from the first (or earlier) RCA product and the second or further round of RCA amplification provides a means for amplifying the signal obtainable from a rolling circle amplification reaction. The method of the invention involves generating a second RCA product by RCA of a second, separate, RCA template. By ensuring that the reaction product of the second RCA is physically attached to the product of a first RCA reaction a localised amplification reaction may be obtained. The present invention provides such a method, and has particular utility in the amplification of signals from detection assays based on detecting RCA products.

Rolling circle replication (RCR) is a mechanism used in nature for the replication of circular DNA molecules such as plasmids or viruses The reaction has been adopted as the basis for a laboratory method for amplifying circular molecules and has been demonstrated to be useful in a variety of assays which use or generate a circular nucleic acid molecule as a reporter, wherein the circular molecule is amplified (replicated) by RCA and the replicated or amplified circular nucleic acid molecule is detected. In other methods, desired, or target molecules may be circularised and amplified by RCA. Accordingly, rolling circle replication (RCR) is now commonly referred to as rolling circle amplification (RCA), and these terms are used interchangeably herein.

RCA relates to the synthesis of nucleic acid molecules using a circular single stranded nucleic acid molecule, e.g. an oligonucleotide, as rolling circle template and a strand-displacing polymerase to extend a primer which is hybridised to the circular template (the strand displacing activity displaces the primer and effectively causes the circle to "roll"). The primer may in certain typical assays be provided by a target nucleic acid (RNA or DNA) molecule. The addition of a polymerase and nucleotides starts the synthesis reaction, i.e. polymerisation. As the rolling circle template is endless, the resultant product is a long single stranded nucleic acid molecule composed of tandem repeats that are complementary to the rolling circle template (i.e. a concatemer).

In practice, RCA reactions often utilise linear nucleic acid molecules, e.g. oligonucleotides such as padlock probes as described in more detail below, which are manipulated to generate circular nucleic acid template molecules, typically by ligating the ends of the nucleic acid molecule together, e.g. using a ligase enzyme. For instance, the ends of the nucleic acid molecule may be brought into proximity to each other by hybridisation to adjacent sequences on a target nucleic acid molecule which acts as a ligation template. The formation of the circular nucleic acid molecule allows it to be copied in a RCA reaction. This reaction may be initiated by adding a primer to the closed circle or a primer may be generated from the target nucleic acid molecule, i.e. ligation template. The initial primer therefore forms part of the RCA product. This can be particularly advantageous because it may allow localised detection of the target nucleic acid, i.e. in embodiments where the nucleic acid molecule used to prime RCA is immobilized, the RCA product will also be immobilized.

Thus, the RCA product may remain as a string of tandemly repeated complementary copies of the nucleic acid circle, a concatemer, which can be particularly useful for in situ detection, but may also be detected in homogenous ("in solution") assays. For instance, a RCA reaction may result in a 1000-fold amplification of the circle in just 1 hour (based on a circle consisting of about 100 nucleotides). Thus, the RCA of a circular oligonucleotide may result in a RCA product that forms a bundle or "blob" of DNA that can be about 1 μm in diameter. The product, i.e. blob, may be detected by the hybridisation of nucleic acid probes conjugated to fluorescent labels which allows the blob to be visualised by fluorescence microscopy or flow cytometry. In other embodiments, the RCA products may be reduced to monomers by digestion with a restriction enzyme or a ribozyme, which are then detected.

Due to the ability of the RCA reaction to generate a readily detectable signal it is useful as a reporter system for detection of any nucleic acid molecule in a sample, which may be a target nucleic acid molecule (i.e. a nucleic acid molecule to be detected, or where the nucleic acid molecule is the "analyte" of the assay), or it may be a nucleic acid molecule which is to be detected as a marker (or proxy) for the presence of the target analyte. Thus the RCA reaction has been used to detect directly target nucleic acids in cell and tissue samples, e.g. in situ, i.e. localised, detection of nucleic acid molecules, which is of significant interest both for research and diagnostic purposes. However, RCA assays are not limited to use in heterogeneous formats and may also find utility in homogeneous assays (see e.g. WO 2009/037659).

RCA has also been utilised in methods for the detection of other analytes, i.e. analytes other than nucleic acid molecules such as proteins, peptides etc. In this respect, a variety of assays have been developed in which a nucleic acid molecule may be used to directly or indirectly tag or label a target analyte in a sample and detection of the nucleic acid molecule serves to indicate the presence of the analyte in the sample. In some methods a new nucleic acid molecule may be generated in a sample (i.e. a nucleic acid molecule that was not present in the original sample and was not one of the components added to the sample) when one or more molecules that interact with, e.g. bind to, the target analyte. The detection of the generated nucleic acid molecule is indicative of the analyte in a sample.

Various methods based upon detecting such a proxy or marker nucleic acid molecule using an RCA reaction as part of the detection strategy are well described in the art, including for example, immuno-RCA, assays using padlock probes and proximity probe assays which generate a circular nucleic acid molecule. In all these cases, the methods rely on providing or generating a circular nucleic acid molecule which may then be used as a substrate (template) for an RCA reaction, and the RCA product may then be detected as a substitute for detecting the target analyte directly.

Immuno-RCA involves labelling an antibody for a specific target analyte with a nucleic acid molecule. Typically, the target analyte is captured on a substrate, e.g. with a first antibody and contacted with the antibody:nucleic acid complex. A circular (or circularisable) oligonucleotide is hybridized to the nucleic acid molecule conjugated to the antibody (the oligonucleotide may be pre-hybridized or added after the antibody has been allowed to interact with the target analyte). Excess antibody may be washed away before the sample is subjected to an RCA to amplify the circular/circularised oligonucleotide. The nucleic acid molecule conjugated to the antibody is used as the primer for RCA. Thus, the RCA product is tethered to the antibody that is interacting with the target analyte, thereby allowing localised detection of the analyte in the sample, e.g. in a cell or tissue sample.

A proximity assay relies on the principle of "proximity probing", wherein an analyte is detected by the binding of multiple (i.e. two or more, generally two or three) probes, which when brought into proximity by binding to the analyte (hence "proximity probes") allow a signal to be generated. Typically, at least one of the proximity probes comprises a nucleic acid domain linked to the analyte-binding domain of the probe, and generation of the signal involves an interaction between the nucleic acid moieties and/or a further functional moiety which is carried by the other probe(s). Thus signal generation is dependent on an interaction between the probes (more particularly by the nucleic acid or other functional moieties/domains carried by them) and hence only occurs when the probes have bound to the analyte, thereby lending improved specificity to the detection system. The concept of proximity probing has been developed in recent years and many assays based on this principle are now well known in the art. For example, proximity ligation assays (PLAs) rely on proximal binding of proximity probes to an analyte to generate a signal from a ligation reaction involving or mediated by (e.g. between and/or templated by) the nucleic acid domains of the proximity probes.

The nucleic acid domains of the proximity probes when in proximity may template the ligation of one or more added oligonucleotides to each other, including an intramolecular ligation, to circularise one or more added linear oligonucleotides, to form a nucleic acid circle, based on the so-called padlock probe principle, as described for example by Landegren et al. in WO 99/49079. In such a method the ends of the added linear oligonucleotide(s) are brought into juxtaposition for ligation by hybridising to one or more circularisation templates provided by the nucleic acid domain of one or more proximity probes. Various such assay formats are described in WO 01/61037.

It will accordingly be evident that RCA may be of utility in the specific detection of any nucleic acid molecule in a sample, regardless of whether it is the "original" target analyte in a sample or it is a "proxy" target analyte generated by the interaction of specific detection molecules, e.g. proximity probes, with the target analyte, e.g. protein. RCA may also be useful in the detection of amplified nucleic acid molecules. For instance, in samples in which the target nucleic acid molecule is present in low amounts, e.g. rare transcripts, RCA can be used to "enhance" detection by increasing the amount of nucleic acid that is available to be detected.

Various modifications of the basic RCA reaction have been proposed, including to provide a more than linear amplification, for example to improve sensitivity in assays based upon detecting an RCA product.

Many of these methods include further amplification of the signal generated in the first RCA reaction, that is amplification based on the first RCA product. In general these are focused on techniques which use the product of the first RCA reaction as a template for primer extension. For example, in the hyperbranched RCA reaction (HBRCA), a primer is hybridised to each tandem repeat in the concatemeric RCA product generated by the first RCA reaction. The primers are then extended using the first RCA product as a template. As each primer is elongated it runs into and displaces the product of a downstream primer to generate a single-stranded tandem repeat of the sequence of the original first RCA reaction product. Further, the primer for the first RCA reaction may then hybridise to the tandem repeats in the generated (displaced) single strands and be extended to form further displacing strands, and so on. Thus, alternate strand copying and strand displacement processes generate a continuously expanding pattern of DNA branches, and by virtue of the strand displacement, also a discrete set of free DNA fragments comprising double-stranded pieces of the unit length of the circle, and multiples thereof. This is described by Lizardi in Nature Genetics 1998, 19, 225-2323 and in WO 97/19193.

A similar method is the DNA cascade reaction, as described by Koch in WO 97/20948, but in this case the primer extension time is controlled so that copying of the strands does not proceed to the end and the displaced strands remain attached to the template (RCA product).

In WO 03/012199 a method, termed the circle-to-circle (C2C) method, based on repeat RCA reactions, is described, which may also be used for amplifying the signal generated from a first RCA reaction. Again, the first generation RCA product is used as a template for extension of a primer hybridised to said product. However, in this method the first generation RCA product is cleaved into monomers (each monomer corresponding to one tandem repeat in the concatemeric product), which are circularised and then used as RCA templates in a further round of RCA. Since in this method the first RCA product is cleaved, there can be no localisation of the second RCA products to the first product.

In U.S. Pat. No. 5,854,033 Lizardi describe a further method termed nested ligation-mediated RCA (nested LM-RCA). LM-RCA involves generating an RCA product based on a principle analogous to padlock probing, in which a circularisable oligonucleotide (an "open circle probe") is hybridised to a target nucleic acid sequence (if present) and is then ligated to form a circle. After ligation a primer is hybridised to the circle and an RCA reaction is preformed to generate a linear RCA product comprising tandemly repeated complementary copies of the circle (termed the "tandem sequence DNA; TS-DNA). In the nested LM-RCA reaction, in order to amplify the signal, a further circularisable oligonucleotide is hybridised to the TS-DNA, ligated, and subjected to a second round of RCA. It will be understood that in these procedures during the RCA reaction the circularised oligonucleotide may become displaced, and hence separated, from its target (to which it was hybridised). For in situ methods where a localised signal is desired an alternative method is proposed in which the first circularisable oligonucleotide (OCP) is ligated but not amplified, and the second circularisable oligonucleotide is hybridised to the first, circularised, oligonucleotide (OCP).

Ward in U.S. Pat. No. 6,686,157 describes novel probes, termed lollipop probes, as a means for enabling signal amplification by RCA. The lollipop probe is a branched three-tailed structure with two target-binding arms, and a third arm providing a binding site and primer for RCA of an added circular DNA molecule. The target-binding arms are designed to bind to adjacent sequences on a target nucleic acid molecule, such that upon hybridisation to the target they may be ligated together, topologically linking the probe to its target sequence. The nucleic acid targets of Ward are analyte nucleic acid molecules it is desired to detect and there is no suggestion that the target may itself be an RCA product.

Whilst methods for signal amplification based on carrying out secondary amplifications of primary RCA products have been described, there is a continuing need to develop assays with increased sensitivity and/or performance, e.g. with stronger signal, more rapid signal generation, and/or improved signal to noise ratio. In particular, there is a need to develop assays in which the secondary signal may be localised to the first, for example but not only in the case of in situ detection processes. It may in certain cases be useful or desirable to couple and co-localise signal detection based on the primary detection product, to signal detection based on a secondary detection product.

The present invention is directed to addressing this need, and is based on the concept of performing a second RCA reaction, which is dependent upon a first RCA reaction, but which does not amplify the first RCA product, in order to amplify the signal which may be generated by the first RCA reaction (in other words to generate more "signal product" by the second RCA, which is detected to generate the signal). An important feature of the present method is that the second RCA product is and remains physically attached to the first RCA product, in order that the signal from the second RCA product is localised to the first RCA product.

By utilising an RCA primer which is hybridised (directly or indirectly) to the first RCA product to amplify a second RCA template circle, a second RCA product may be generated by extension of the RCA primer, which, by virtue of hybridisation of the primer, is hybridised, and hence attached to the first RCA product. Since the first RCA product is a concatemer comprising tandem repeat complementary copies of the template circle for the first RCA reaction (the "first RCA circle"), the RCA primer for the second RCA will bind to repeated copies of its cognate primer-binding sequence, repeated throughout the first RCA product. In other words, the first RCA product will comprise repeated binding sites for the RCA primer for the second RCA, one in each of the tandem repeats ("monomers" of the concatemer). Each such primer can prime a second RCA reaction, leading to increased, more than linear, amplification.

In order to preserve the hybridisation of the RCA primer (and hence the localisation of the second RCA product) to the first RCA product, it is necessary to ensure that no extension using the first RCA product as template can take place, or that any extension which does occur is limited such that there is no displacement of any downstream hybridised primers. Accordingly a further feature of the invention is that the second RCA primer is unable to prime extension using the first RCA product as template, or that any such extension is limited to avoid displacement of downstream hybridised primers. Whilst a simple RCA primer will anneal to the first RCA product at its 5' end, and will have a free, non-hybridised, 3' end available to bind to a second RCA template circle, and hence should not have a hybridised 3' end available for priming extension on the first RCA product, it is possible that a construct able to prime extension on the first RCA product might be generated, for example by the exonuclease action of a polymerase enzyme degrading the single stranded 3' end of the primer. It is important therefore to carry out the method in such a way that the RCA primer is made unable to prime on the first RCA product to any significant degree. As will be described in more detail below, such extension may be prevented or limited by designing or modifying the RCA primer such that it is not capable of functioning as a primer on the first RCA product, e.g. by incorporating an "exonuclease block" into the primer, to prevent exonuclease digestion from creating a primer capable of priming on the first RCA template, and/or by ensuring that no exonuclease activity is present in the reaction mixture, e.g. by using a polymerase enzyme with no exonuclease activity. Furthermore, as also will be described in more detail below, it is envisaged that probes may be provided in various forms, which hybridise to the first RCA product and which may comprise or provide the primer for the second RCA, including for example by unfolding (i.e. release or opening up of a double-stranded portion of the probe to reveal a single-stranded region) or cleavage of the probe. Such probes may also comprise or provide other components of the second RCA reaction (for example the second RCA template). Such probes may comprise a 3' end which is hybridised to the target. In such embodiments it is important to ensure that such a hybridised 3' probe end (which is not to function as the second RCA primer) is protected or blocked from extension on the first RCA product as template. This may be achieved by incorporating a blocking group into the hybridised 3' end, and/or by using blocking oligonucleotides, which are themselves blocked from extension and displacement, hybridised in between the primer-providing probes. In this way, any first RCA product-templated extension which does take place may be limited from extending into, and displacing any downstream-hybridised probes. This is described further below.

Advantageously, therefore, the method of the present invention, allows the second RCA to be localised to the first RCA. As will be explained further below, this may have benefits in localised (spatial) detection of target analytes (e.g. in in situ detection procedures). Since the template molecule for the second RCA is not bound directly to the first RCA product, any possible issues of topological constraint resulting from hybridisation and catenation of the circle, (which are recognised in the art to inhibit RCA reactions) are avoided.

The strong signal amplification afforded by the second RCA reaction may increase the sensitivity of the method and provide the ability easily to detect or visualise the RCA products, for example at low microscopic magnification or with digital image scanning methods, or possibly even without the aid of microscopy. The strong signal from the increased amount of second RCA product may also open up the possibility of using other detection modalities, e.g. flow cytometry, in RCA-based detection assays, and thereby increase the instrument base possible to use in such assays. Signal amplification may be increased even further by a possible third or further generations of RCA all linked by virtue of the primers for each RCA generation, which link the previous RCA product to the next RCA product.

Further, since the second RCA reaction may be initiated during the first RCA reaction (i.e. as the first RCA product is being formed, or whilst the first RCA reaction is ongoing), a more rapid signal generation may be achieved, leading to faster assays.

In view of this coupling of two more RCA generations to yield both increased and faster signal amplification, we have termed this new method super RCA (sRCA).

In it broadest and first aspect, the present invention provides a method for performing a localised RCA reaction comprising at least two rounds of RCA, wherein the product of a second RCA reaction is attached, and hence localised, to a product of a first RCA reaction, said method comprising:
(a) providing a first RCA product;
(b) directly or indirectly hybridising to said first RCA product a probe which comprises or provides a primer for a second RCA reaction; and
(c) performing a second RCA reaction using said RCA primer of (b) to form a second RCA product, wherein in said reaction:
(i) said probe and said primer are not able to prime extension using said first RCA product as template or any such extension is limited to avoid displacement of any probe hybridised to the first RCA product;

(ii) the direct or indirect hybridisation of the RCA primer of (b) to the first RCA product is maintained and, by virtue of said hybridisation, the second RCA product is attached to the first RCA product;

(iii) a RCA template for said second RCA reaction is comprised in or provided by the probe, or is separately provided.

Steps (a), (b) and (c) may be performed simultaneously or sequentially.

The RCA template for the second RCA reaction (the "second RCA template") may be in circular or circularisable form. By "circularisable" is meant that the RCA template is in the form of a linear molecule having ligatable ends which may circularised by ligating the ends together directly or indirectly, i.e. to each other, or to the respective ends of an intervening ("gap") oligonucleotide or to an extended 3' end of the circularisable RCA template. A circularisable template may also be provided in two or more parts, namely two or more molecules (i.e. oligonucleotides) which may be ligated together to form a circle. When said RCA template is circularisable it is circularised prior to RCA by ligation. Ligation may be templated using a ligation template. Accordingly, when the RCA template is circularisable, a ligation template may be comprised in or provided by said probe, or it may be separately provided. The circularisable RCA template (or template part or portion) will comprise at its respective 3' and 5' ends regions of complementarity to corresponding cognate complementary regions (or binding sites) in the ligation template, which may be adjacent where the ends are directly ligated to each other, or non-adjacent, with an intervening "gap" sequence, where indirect ligation is to take place. In an embodiment in which the ligation template for the circularisation of the circularisable RCA template is separately provided, it may for example be provided by a different, second, probe which also hybridises, directly or indirectly, to the first RCA product. Such a second probe may be viewed as a "ligation template probe" or "circularisation probe", or as a "secondary probe" (in which case the primer-providing first probe mentioned in the method above may be viewed as a "primary probe").

The first RCA product may be the product of a primary (i.e. initial) RCA reaction, or it may be the product of a further or later RCA reaction. The second RCA reaction may be a secondary or further, or later, RCA reaction. It will thus be understood that the method of the invention may involve multiple, successive rounds of RCA, e.g. two, three, four or more, wherein in each round a probe is used which is hybridised, directly or indirectly, to the reaction product of a previous round of RCA. Expressed in other words, the method of the invention may comprise repeating steps (a), (b) and (c) one or more times.

It is a feature of the present invention that the first RCA product remains intact in the method, i.e. it is not cleaved (e.g. it is not cleaved into monomers).

Since an RCA product contains multiple repeat (or tandem) copies (or monomers) of a sequence (i.e. it is a concatemer of monomers), multiple probes will be bound. Thus, the method of the invention more particularly comprises hybridising (directly or indirectly) a multiplicity of probes to the first RCA reaction product. As used herein the term "multiple" or "multiplicity" means two or more, e.g. at least 2, 3, 4, 5, 6, 10, 20, 30, 50, 70 or 100 or more. The probe is hybridised, directly or indirectly, to a binding site present in each repeat unit or monomer of the first RCA product (each repeat unit or monomer being a complementary copy of the circular RCA template used to produce the first RCA product (the "first RCA template")). It will be understood that whilst each of the repeat units or monomers of the product of the first RCA reaction comprise the binding site for the probe, in practice not all of these binding sites may (or will) be occupied by a probe after probe hybridisation. It suffices that a number, or multiplicity, of such binding sites are bound by a probe. Thus, in the method of the invention the probe may hybridise to a probe-binding site present in a monomer of the first RCA product or to an intermediate nucleic acid molecule hybridised to a complementary sequence present in a monomer of the first RCA product. More specifically, the probe hybridises to a probe-binding site in at least one monomer of the RCA product or to an intermediate nucleic acid molecule hybridised to a complementary sequence present in at least one monomer of the first RCA product.

The probe may be hybridised directly to the first RCA product i.e. it binds directly to a probe-binding site present in the first RCA product which is complementary or "cognate" to a binding site in the probe. Alternatively, the probe may be hybridised indirectly, for example by binding to an intermediate nucleic acid molecule which is itself hybridised (directly or indirectly) to the first RCA product. In such an embodiment, the probe is bound to a complementary (or cognate) binding site present in the intermediate nucleic acid molecule. The intermediate nucleic acid molecule may be bound to the first RCA product by hybridising to a complementary (or cognate) binding site present in each repeat unit (or monomer) of the first RCA product). However, as indicated above, it may be the case that not every intermediate molecule, or not every probe-binding site in the intermediate molecule, will be bound by a probe. If a second probe, as described above, is used to provide a ligation template for circularisation, then analogous considerations apply.

In the method of the invention the probe comprises or provides a primer for the second RCA reaction. It may in certain embodiments also comprise or provide a circular or circularisable RCA template for the second RCA reaction, and if required a ligation template to circularise a circularisable such second RCA template. As will be described in more detail below, the probe may comprise or contain a portion or domain which is directly able to function as a primer, or as an RCA template etc. Thus at it simplest, and as described further below, the probe may simply comprise a stretch of nucleotides able to hybridise to an RCA template and prime its replication. Likewise in other embodiments a preformed circular nucleic acid molecule able to function as an RCA template may be provided as part of the probe (e.g. the probe may comprise such a circle hybridised to another oligonucleotide—see further below). However, in other embodiments, the probe is designed to release, or to give rise to, or to generate, or allow to be generated, the primer, RCA template, and optionally ligation (circularisation) template components required for the RCA reaction (in other words the nucleic acid components of an RCA reaction). This may be achieved for example by unfolding and/or cleavage of the probe to release or reveal portions or domains which are then able to function as an RCA component, for example as an RCA primer, and/or a ligation (circularisation) template for generation of an RCA template (which may be generated either from released probe domains or from added components, e.g. added oligonucleotides). Accordingly, such a component released by unfolding or cleavage of a probe may be able to function directly as an RCA component, e.g. primer, or released nucleic acid components or domains may interact with one another, or with further added components (e.g. further probes (for example a second probe as above) or added oligonucleotides) to form a circular template for RCA, and ultimately an RCA primer/template complex to enable the second RCA to be performed. A component is "provided" by the probe if it released from or generated from (rather than generated by) a part or domain of the probe. However a probe component (e.g. circularisation/ligation template) may be used to generate a further RCA component from added materials e.g. an added oligonucleotide or an added circularisable RCA template.

It will thus be seen that the probe may indirectly contain, or give rise to, the RCA primer, and if desired also a circular or circularisable RCA template, and optionally ligation (circularisation) template for circularisation of a circularisable RCA template to form a circular RCA template. The term "provides" is accordingly to be interpreted with this in mind. Thus, as used herein the term "provides" means that the probe "contains" or is able to give rise to the component (or RCA element) in question. Taking as an example the RCA primer, "the probe provides a primer" means that the primer element, or sequence of nucleotides (oligonucleotide sequence) of the primer is contained within the probe, and the primer may be generated or released from the probe, for example by cleavage and/or unfolding of the probe. The primer is thus derived from the probe.

The probe of the invention may thus take various forms and may comprise or consist of one or more strands, or component oligonucleotides. One such strand or component oligonucleotide may be a preformed circle (which may be the template for the second RCA reaction). Thus in certain embodiments the probe may comprise a preformed circle hybridised to one or more other strands or oligonucleotides. The probe may thus be viewed as a nucleic acid construct, which may comprise one or more (e.g. two or more or three or more) constituent strands (or oligonucleotides) hybridised together. The probe may contain one or more double-stranded regions, which may be formed by intra-molecular hybridisation e.g. one or more hairpin, or stem-loop structures, or by inter-molecular hybridisation of separate oligonucleotide components (strands).

The probe comprises:
(i) a domain comprising a region of complementarity to (and hence capable of hybridising to) a target nucleic acid molecule, which may be a first RCA product or an intermediate molecule hybridised (directly or indirectly) to the first RCA product (a "binding domain", or more particularly "target-binding domain"). The region of complementarity thus constitutes a binding site for the target molecule (which will itself contain a cognate or complementary binding site (or region of complementarity)).
(ii) a domain comprising or capable of providing a primer for the second RCA reaction (a "primer domain");
(iii) a domain comprising a region of complementarity to (and hence capable of hybridising to) a circular or circularisable template for said second RCA reaction ("second RCA template") (a "RCA-template complementary domain"). The region of complementarity thus constitutes a binding site for the template (which will itself comprise a cognate or complementary binding site (region of complementarity)). The domains may be separate or overlapping. For example, domains (ii) and (iii) may be overlapping.

In an embodiment in which domain (iii) is complementary to a circularisable template, the domain may also function as a ligation template for circularisation of the circularisable template. Thus the probe may further comprise:
(iv) a domain comprising or capable of providing a ligation template (or circularisation template) for circularisation of a circularisable template for the second RCA (a "ligation-template domain"). Domain (iv) may be overlapping with domain (iii).

In certain embodiments, the probe may further comprise:
(v) a domain comprising or capable of providing a circular or circularisable template for the second RCA reaction ("second RCA template") (a "RCA template domain").

Domains (ii) to (v), and particularly domains (ii), (iv) and (v), may be viewed as comprising or providing the nucleic acid components of an RCA reaction. Accordingly in certain embodiments the probe may comprise or provide all the nucleic acid components required for an RCA reaction, namely an RCA primer and an RCA template, which may be in circular or circularisable form, and if said RCA template is circularisable, a ligation template for circularisation of the circularisable RCA template. Such probes are termed herein "RCA reporters" and are described further below (and in our co-pending UK application entitled "Product and Use thereof" filed on even date herewith, the disclosures of which are herein incorporated by reference).

However, the probe need not provide all the nucleic acid components for the second RCA reaction, and the second RCA template may be separately provided. For example a circular template for the second RCA may be separately provided. In other embodiments, a circularisable RCA template is separately provided. This may be a linear oligonucleotide with free 3' and 5' ends available for ligation together (directly or indirectly). The circularisable RCA template may hybridise to a ligation template with the respective 5' and 3' ends juxtaposed for ligation, either directly together, or indirectly, to the respective ends of an intervening "gap" oligonucleotide, or prior to ligation the hybridised 3' end of the circularisable molecule may be extended by a "gap-filling" polymerase extension reaction to meet the 5' end, before the ends are joined by ligation to circularise the molecule. Advantageously, according to the present invention, the ligation template for circularisation is comprised within or provided by the probe.

In other embodiments the probe may interact with other added reactants e.g. added oligonucleotides to generate the circular template for the second RCA reaction. Thus the probe may provide a ligation template which acts in concert with another, separately provided, ligation template to allow the circularisation of two or more added oligonucleotides. For example the probe may comprise a ligation template domain which may act, together with a further separate ligation template domain (e.g. provided by a second, different, probe), to template the ligation of two or more added oligonucleotides into a circle, thereby generating a circular template for the second RCA. Alternatively, the probe may comprise a domain which is complementary to a region of a circularisable second RCA template which is separate to a ligatable end of said template (e.g. in a mid-portion of the circularisable molecule) and the ends of said circularisable molecule may hybridise to a separate ligation template domain provided separately, e.g. by a second probe.

It will be understood that domain (ii) (the primer domain) will comprise a region of complementarity to the RCA template, in order that the primer may hybridise to, and prime RCA of, the RCA template. However, the probe may also contain further, separate, domains comprising a region of complementarity to the second RCA template. For example, a ligation template domain (iv) will also contain a region of complementarity to the second RCA template. Thus a probe of the invention may comprise more than one of certain domains indicated above, notably domains (i) and (iii). As will be apparent from more detailed descriptions below, the probe may also contain more than one of domains (iv) and (v).

In particular, the probe may contain more than one domain (i) containing a region of complementarity to its target sequence, e.g. two or more, or three or more. In particular the probe may contain two domains (i). In other embodiments it may comprise three domains (i). The domains may lie on the same or different strands or component oligonucleotides of the probe. For example, where the probe is or comprises a linear oligonucleotide, the two domains (i) may be provided at each of the 3' and 5' ends of the oligonucleotide. In certain such embodiments, the probe may hybridise to its target molecule in such a manner that the ends are juxtaposed for ligation, either directly, or indirectly, as indicated above for ligation of a circularisable RCA template.

As indicated above and as will be described in more detail below, in certain embodiments the probe may be cleaved and/or unfolded to release one or more of the domains indicated above. For example the probe may be cleaved and/or unfolded to release the primer for a second RCA reaction.

Accordingly, in one particular embodiment the invention provides a method for performing a localised RCA reaction comprising at least two rounds of RCA, wherein the product of a second RCA reaction is attached, and hence localised, to a product of a first RCA reaction, said method comprising:
(a) providing a first RCA product;
(b) directly or indirectly hybridising to said first RCA product a probe which comprises or provides a primer for a second RCA reaction, wherein said probe is cleaved and/or unfolded to release said RCA primer; and
(c) performing a second RCA reaction using said RCA primer of (b) to form a second RCA product, wherein in said reaction:
(i) said probe and said primer are not able to prime extension using said first RCA product as template or any such extension is limited to avoid displacement of any downstream probe hybridised to the first RCA product;
(ii) the direct or indirect hybridisation of the RCA primer of (b) to the first RCA product is maintained and, by virtue of said hybridisation, the second RCA product is attached to the first RCA product;
(iii) a RCA template for said second RCA reaction is comprised in or provided by the probe, or is separately provided.

The term "release" is used broadly herein to indicate that the domain (or probe component) is made available to function, for example unfolding of a hairpin structure within the probe may release a 3' end of the probe which is then available to act as primer, or a region of complementarity may be revealed. Unfolding by displacement of a hybridised strand or oligonucleotide may also release domains (or components). It will thus be noted that the term "unfolding" is used broadly herein to include any means of opening up, or separating, a double-stranded structure (duplex). Thus, it includes not only opening up of hairpins, but also strand displacement, e.g. displacement of all or part of a hybridised oligonucleotide or strand. In other embodiments, the primer may be released by cleavage, which may be exo- or endonucleolytic cleavage. For example an extended free 3' end of the probe (or component probe oligonucleotide) may be digested by an exonuclease (which may be provided by a separate enzyme or by the polymerase used for RCA) to cleave back to a 3' end which is hybridised to a circular RCA template, and which is hence able to prime RCA of the template. Alternatively a primer may be released by cleavage of a cleavage site in the probe, for example for an restriction enzyme, or more particularly for a nickase enzyme (such that only one strand is cleaved). Various such embodiments are described below. In other embodiments both unfolding (for example displacement of a hybridised oligonucleotide component of the probe, or opening of a hairpin) may be used in conjunction with cleavage (e.g. exonucleolytic cleavage) to release the primer. In still other embodiments, different cleavage mechanisms may be combined (e.g. nickase cleavage combined with exonucleolysis of a released 3' end).

Release of other probe domains or components e.g. a ligation template and/or a circular or circularisable RCA template, may optionally take place analogously. For example cleavage of the probe may, in addition to the primer, release a circularisable RCA template, which may be circularised using either the primer as ligation template, or by a separate ligation template, which may in certain embodiments also be released by cleavage of the probe.

In the methods of the invention it is undesired that the template for the second RCA reaction should hybridise to the first RCA product. Thus, either the second RCA template is not able to hybridise to the first RCA product of the conditions of the method are such as to inhibit or minimise any such hybridisation. In particular, it should not be able to hybridise to the first RCA product at the same time as binding to the primer for the second RCA reaction. Accordingly, and in particular where the second RCA template is provided as a preformed circle, especially when separately provided as a preformed circle, it is a preferred feature that the second RCA template is not able to bind simultaneously to both the first RCA product and the probe or primer for the second RCA. In particular, in this embodiment the second RCA template does not contain separate binding sites for both the first RCA product and the probe, or for both the first RCA product and the primer for the second RCA reaction.

Alternatively put, the probe/primer and second RCA template are such that a 3-way junction (3WJ) RCA reaction is not possible. A 3WJ-RCA requires the primer for the RCA to bind both to a target sequence and to the RCA template in order to the RCA reaction to take place and at the same time the RCA template binds directly to the target sequence. In other words in such a reaction the RCA primer is designed such that it cannot bind to the RCA template unless the target molecule is present, and the RCA template binds simultaneously to the target molecule. The present invention does not include a 3WJ-RCA.

In further embodiments of the method of the invention, when the second RCA template is separately provided as a preformed circle, then (i) the primer is provided by cleavage and/or unfolding of the probe; and/or (ii) priming of extension on the first RCA product in step (c)(i) of the method is prevented or limited by an extension and/or degradation and/or displacement block (see further below).

The method of the invention may be homogenous or heterogeneous. That is, it may be performed in solution, without a solid phase or support (i.e. without immobilisation of any reaction components) or it may be performed in an immobilised or solid phase-based format, particularly where the first RCA product is immobilised. Immobilisation of the first RCA product may be achieved in various ways. For example in an in situ assay the first RCA product may be formed in a first RCA reaction primed using a target (analyte) nucleic acid as first RCA primer. Here the first RCA product is attached to the target tissue sample which is itself fixed to a solid support. This may occur for example where a target nucleic acid is detected using a padlock probe. Alternatively, the first RCA may be primed by an nucleic acid domain of an immuno RCA or a proximity probe, which is bound to an immobilised (or fixed) analyte target. In other embodiments, the primer for the first RCA reaction may simply be immobilised to a solid support. Use of a heterogeneous, immobilised format allows washes to be readily performed, and hence for example allows for ready removal of unbound probes, and/or or other unreacted reaction components added, or spurious unwanted reactions, not physically attached to the surface. Thus, a heterogeneous, or solid phase-based method may readily be performed sequentially.

In one preferred embodiment of the invention, the RCA primer and/or a circular RCA template are unable to form (e.g. be released), or to generate a primer/RCA template complex, unless said probe has hybridised (directly or indirectly) to the first RCA product. In other words the primer and/or circular RCA template are not able, or are not available, to take part in the second RCA reaction unless the probe has hybridised to the first RCA product. Thus, the second RCA reaction is dependent upon the presence of the first RCA product. In this way the specificity of the method may be improved. The second RCA reaction may thus be viewed as a target-dependent RCA reaction, wherein the target of the second RCA reaction is the first RCA reaction product.

This may be achieved by controlling how the method is conducted, and/or by designing the probe such that release of the primer, and optionally other probe components/domains, is not able to take place until or unless the probe has bound to the first RCA product (or intermediate molecule). In other words, in certain embodiments, only upon hybridisation (directly or indirectly) of the probe to the first RCA product, may the probe be cleaved and/or unfolded to release the primer (and optionally other probe domains/components, for example a ligation template for circularisation of an added circularisable RCA template, or of a circularisable RCA template also released by cleavage and/or unfolding of the probe).

Most simply the primer (and optionally the circular or circularisable RCA template and/or other probe domains/components) may be rendered unable to take part in the second RCA reaction by removing any unhybridised probes. This may readily be achieved in a solid phase or immobilised format by washing away any unbound reactants. Accordingly, in the absence of the first RCA product, the probe has no "binding target" (i.e. no first RCA product or no intermediate nucleic acid molecule), and hence is not immobilised by binding to its target, and may be washed away. In this way the probe is not available for the second RCA if the first RCA product is absent.

Thus, in a preferred embodiment of the method of the invention, the primer is unable to prime said second RCA reaction unless the probe has hybridised to the first RCA product. Such a prevention, or reduction, of priming of the second RCA reaction in the absence of the first RCA product may be achieved by conducting the method such that unbound probe (that is probe which has not hybridised to the first RCA product) is removed before carrying out the RCA reaction of step (c). This may readily be achieved for example by carrying out the method in a solid phase format and washing after the step of probe addition and hybridisation. Alternatively or additionally, as mentioned above and discussed further below, the probe may be designed to release one or more of the nucleic acid components of an RCA reaction (primer, RCA template, optionally ligation template for circularisation to form a circular RCA template) by cleavage and/or unfolding, and this release is either dependent on (e.g. requires) hybridisation of the probe to the first RCA product, and/or the released components may only react to form a primer/template complex for RCA if the probe has hybridised to the first RCA product.

Accordingly, the method is designed or conducted in such a way that production of the second RCA product is prevented to minimised in the absence of the first RCA product. More particularly, in the method of the invention, in the absence of the first RCA product production of the second RCA product is prevented or reduced to stochastic levels.

It will be understood that whilst in such an embodiment the method is designed or conducted such that the second RCA reaction should not take place unless the first RCA product is present, it is the nature of such methods that non-specific reactions can occur, and absolute prevention cannot be guaranteed. Thus, certain undesired non-specific or random reactions or interactions may take place in the sample or reaction mixture, and these may lead to the generation of a second RCA product, for example primed by a component or nucleic acid molecule other than the probe/primer. This is what is meant by production of second RCA product at stochastic levels.

As noted above, a significant feature of the method of the invention is that the probe, and in particular the primer comprised in or provided by the probe, is unable to prime extension using the first RCA product as template, or that any such extension which does take place is limited to avoid displacement of any downstream probes (or primers) hybridised to the first RCA product. It will be understood of course that this requirement applies to any method component or reactant which is hybridised to the first RCA product. This will include any intermediate oligonucleotide molecules which are used, or any second, or different, probes which are hybridised to the first RCA product.

To achieve this feature (the feature of step (c)(i)), various means and procedures may be used, singly or in combination, depending on the precise nature of the method steps and probe design employed. For example, modifications (e.g. blocking groups or modified residues) can be incorporated into the probe (and any second probe which is used), which inhibit polymerase and/or exonuclease action (i.e. which inhibit extension and/or degradation), or which inhibit strand displacement. Blocking oligonucleotides (e.g. with modifications as above) may be used to protect a 3' end hybridised to the first RCA template (or intermediate molecule) from extension. For example, such blocking oligonucleotides may be hybridised to the first RCA template in between the probes of the invention (e.g. adjacent to a 3' end it is not desired to ligate). To prevent unwanted exonuclease digestion of any hybridised probes or probe components from creating a primer/template construct capable of priming on the first RCA product, the presence of any reagents having exonucleolytic activity can be avoided, for example an exonuclease-deficient polymerase can be used. In certain embodiments washing steps may be used. For example, in the case of a probe which is designed to have one or more ligatable ends which hybridise to the first RCA product in juxtaposition for ligation, any probes which have hybridised but not ligated may be removed by stringent washing (according to principles well known in the art). This is particularly applicable in the case of heterogeneous, or solid phase-based methods. Any combination of such means may be employed.

In terms of preventing or inhibiting priming on the first RCA product as template, there are a number of scenarios to be considered. Firstly in the case of probes which comprise or release a free 3' end which is not hybridised to the first RCA product (e.g. a free 3' end intended to act as a RCA primer), it is important to inhibit cleavage of the 3' end back down to the hybridised region (which would lead to the creation of a primer hybridised to the first RCA template). This may be achieved by using exonuclease-deficient and/or exonuclease-free reagents (e.g. a polymerase deficient in or lacking 3' exonuclease activity). Alternatively or additionally a so-called exonuclease block, as indicated above, may be used (namely a modification which acts to block, or inhibit, exonuclease activity, particularly 3' exonucleolytic activity). For example the probe or probe component may comprise such a block in the region between the 3' end of the probe or primer and the hybridised region, e.g. a stretch of nuclease-resistant nucleotides.

In the case of probes or probe components having a 3'end which hybridises to the first RCA product, where this 3' end is not required for ligation, a modification or block may be included at or near the 3' end which acts to inhibit extension (e.g. a "polymerase-block" or "extension block"). Alternatively or additionally a blocking oligonucleotide may be used, to prevent any extension which may occur from the 3' end from extending into and displacing any downstream probes. As noted above, such a blocking oligonucleotide will itself be modified to incorporate an extension and/or degradation block (e.g. at the 3'end) and a displacement block (e.g. at the 5' end).

In certain embodiments a probe may comprise a 3'end which hybridises to the first RCA product and is required for ligation (e.g. either to the 5' end of the probe, or to another probe). In such a situation it would not be appropriate to include an extension and/or degradation block at the hybridised 3'end, in order to ensure that the 3' end is available for ligation. In this case, unwanted 3' extension of any unligated 3' ends may be inhibited by stringent washing to remove any unligated probes. Alternatively or additionally, in such a case the probe may be modified at or near a hybridised ligatable 5' end to include a displacement block. In such a case any extension which does take place from the 3'end will not be to displace the hybridised 5'end (of the probe itself or of a downstream hybridised probe).

Modifications or blocking groups for inhibiting or blocking exonuclease and/or polymerase action (i.e. for inhibiting or blocking degradation and/or extension), as well as inhibiting or blocking displacement are well known in the art and described in the literature, and any of these may be used. Accordingly a nucleotide may be modified to include or incorporate a blocking group which may inhibit an enzyme (e.g. polymerase) from functioning, e.g. from binding. For example an exonuclease block may comprise a region of nuclease-resistant nucleotide residues. These may for example be 2'O-Me-RNA residues, Locked Nucleic Acid (LNA) residues, Peptide Nucleic Acid (PNA) residues, phosphothiate-modified nucleic acids, or a polyethylene-linker backbone moiety incorporated in between nucleotide residues. Abasic (apurinic or apyramidinic, or AP) sites may also be included as exonuclease blocks. Further the probe or probe component may in include a hairpin structure as an exonuclease block. There are several means of modifying nucleic acids so that they are exonuclease resistant and/or do not function as a primer and it is not intended that the methods of the invention are limited to the examples listed above.

Similarly, an extension or polymerase block may include any of the modified residues or blocks indicated above as exonuclease blocks. Any group or modification which inhibits binding of polymerase may be incorporated into the relevant region of the probe. For example, any groups having an intercalating function may be used, e.g. acridine groups.

A blocking oligonucleotide may include or incorporate any of the exonuclease or extension/polymerase blocks mentioned above. Blocking oligonucleotides which may inhibit unwanted extension reaction are described in the literature, for example in Olasagasti et al., 2010, Nature Nanotechnology, 5, 798-806 and in the Senior Thesis of Rashid, at the University of California, Santa Cruz, entitled Blocking Oligomer Design (3/10-3/11).

Displacement blocks are also known in the art and any reported or known displacement block may be used. A displacement block may comprise any stretch or region of modified nucleotide residues that form more stable hybrids with DNA and/or RNA than unmodified DNA and/or RNA. Such modifications include LNA, PNA, and 2'-O-Me RNA residues. Thus a stretch or region of such residues of sufficient length, or strength, to avoid displacement may be used. Abasic (AP) sites may be also be used. DNA clamps as reported in the literature may also be used.

Accordingly, in one preferred embodiment, the method of the invention comprises the use of a probe which incorporates (or comprises) one or more modified regions which act to inhibit degradation, extension and/or strand displacement, and/or blocking oligonucleotides are used (which may themselves incorporate such modified regions).

In such a preferred embodiment the invention can be seen to provide a method for performing a localised RCA reaction comprising at least two rounds of RCA, wherein the product of a second RCA reaction is attached, and hence localised, to a product of a first RCA reaction, said method comprising:

(a) providing a first RCA product;

(b) directly or indirectly hybridising to said first RCA product a probe which comprises or provides a primer for a second RCA reaction; and (c) performing a second RCA reaction using said RCA primer of (b) to form a second RCA product, wherein in said reaction:

(i) said probe comprises one or more modified regions and/or blocking oligonucleotides are used, such that said probe and said primer are not able to prime extension using said first RCA product as template or any such extension is limited to avoid displacement of any probe hybridised to the first RCA product;

(ii) the direct or indirect hybridisation of the RCA primer of (b) to the first RCA product is maintained and, by virtue of said hybridisation, the second RCA product is attached to the first RCA product;

(iii) a RCA template for said second RCA reaction is comprised in or provided by the probe, or is separately provided.

More particularly, in this embodiment, the modified region, as indicated above, acts to inhibit degradation, extension and/or strand displacement. Accordingly, the modified region may comprise or constitute an exonuclease block, an extension block and/or a displacement block. The modified region may comprise modified nucleotides and/or blocking groups and/or hairpin structures. Modified nucleotides include abasic nucleotides. Blocking oligonucleotides comprising one or more such modified regions may be added to hybridise to the first RCA product in such a manner that the probe or primer is not able to extend using the first RCA product as template, or any such extension is limited to avoid displacement of any downstream probe hybridised to the first RCA product. For example, the blocking oligonucleotide may be hybridised adjacent to a hybridised 3' end of the probe, or blocking oligonucleotides may be hybridised to the first RCA product in between a multiplicity of probes, e.g. such that there is at least one blocking oligonucleotide in between any two probes.

As noted above, one of the advantages for the present invention is that the second RCA may be initiated whilst the first RCA in ongoing, or in other words, as soon as the first RCA product has started to form. This leads to the advantage of faster signal generation. Thus signal amplification might optimally might proceed as $v^2/2$, compared to where v is the rate of nucleotide incorporation by the polymerase, compared to v for a single RCA, and hence at a multiple of the rate at which new RCA products are generated. This can speed up any RCA-dependent protocol, and may be of particular value for rapid detection assays. Further increases of signal strength or speed or both are possible with a further round of RCA initiating off and linked to the second RCA reaction product and so forth (e.g. a third, fourth, fifth . . . generation of RCA).

Thus, in one embodiment, the method of the invention may include as step (a) the step of generating a first RCA product, (or performing a first RCA reaction to produce a first RCA product). Steps (b) and (c) may take place as soon as the first RCA product starts to form. Accordingly, steps (a) and/or (b) and/or (c) may be performed simultaneously or substantially simultaneously. In particular, step (b) may be performed simultaneously with step (a). Accordingly, in certain embodiments the reagents for the second RCA reaction, e.g. the probe and any additional reactants required (for example a circular or circularisable second RCA template and/or any second probe) may be added directly to the reagents for the first RCA reaction.

The method of the invention relies upon multiple probes being able to hybridise to the first RCA product. Accordingly, it will be understood that the first RCA product needs to be available for probe hybridisation. This requirement is a feature of all RCA-based detection methods, where an RCA product is detected by hybridising a probe, e.g. a detection probe, to the product, and is well understood in the art. Thus, it may be advantageous for the first RCA product to have low secondary structure. However, this feature may be compensated for by performing the method in conditions which favour hybridisation, according to principles well known in the art. Thus, for example, the method can be performed in the presence of formamide e.g. in buffers containing formamide.

The first RCA product may be derived from the RCA of any nucleic acid (e.g. DNA or RNA) circle, or indeed the circle may be of any modified nucleic acid, as long as it is capable of templating a RCA reaction. The circle (first RCA template) may for example be a reporter DNA circle, namely from any RCA-based detection assay which uses or generates a nucleic acid circle (circular nucleic acid molecule) as a reporter for the assay. Thus the first RCA product may be the product of an immunoRCA or a proximity probe assay in which a circular nucleic acid molecule is generated, for example as discussed above, or it may be obtained by RCA of a circularised padlock probe. Alternatively, the first RCA template used to generate the first RCA product may be a circularised target (analyte) nucleic acid molecule. Circularisation of target nucleic acid molecules using circularisation adaptors (so-called "Selectors") is described by us in WO 99/049079, WO 2003/012119 and WO 2005/070630.

A simple representative embodiment of the invention is depicted in FIG. 1. In this solid phase-based method the product of a first RCA reaction is directly or indirectly immobilised on a solid support. As shown the primer for the first RCA reaction is immobilised. A probe comprising the primer, or more particularly a primer domain (ii), for a second RCA reaction and a binding domain (i) is contacted with and allowed to hybridise to the product of the first RCA reaction, either directly or indirectly (directly is shown). One probe may bind to each repeat sequence (monomer) in the concatemeric first RCA product. The circular or circularisable template for the second RCA reaction is introduced and allowed to hybridise to the probe. If the template is circularisable the probe acts as a ligation template for the circularisation of the RCA template (i.e. also comprises a ligation domain (iv)). Unhybridised or unbound probes are removed, e.g. by performing a washing step. This may be performed after the step of contacting and hybridising the probes but before introduction of the RCA template. Alternatively unbound probes may be removed after both the probes and the RCA templates have been introduced, but before the second RCA is initiated e.g. before reagents necessary for RCA and/or ligation have been introduced (e.g. polymerase and/or ligase enzymes). Further alternatively the RCA template may be pre-hybridised to the probe and the probe/RCA template complex may be added to the first RCA product together (i.e. to the sample or reaction mixture) and allowed to hybridise to the first RCA product. Washing may then be performed to remove unbound probes. Thus the probe (primer) is unable to prime the second RCA reaction unless it has bound to the first RCA product. After the washing steps, and/or any necessary ligation step to circularise a circularisable RCA template, the second RCA reaction may be initiated. The template may hybridise to the probe in such a manner that the probe provides a hybridised 3' end for priming of the RCA, or if the template is hybridised in such a manner that a the probe has a free 3'end, a primer may be generated ("released") by 3' exonucleolytic cleavage to cleave back the free 3' end. This may be provided by a polymerase having 3' exonuclease activity or by a separate exonuclease enzyme. To ensure that the probe is not able to prime extension on the first RCA product, either an exonuclease-deficient polymerase may be used (in this case exonuclease digestion is not required to generate a primer) or an exonuclease block is introduced into the probe, for example in between the 3' end of the primer and the region hybridised to the first RCA product. Alternatively, blocking oligonucleotides may be hybridised to the product of the first RCA reaction between the hybridised probes.

Accordingly, in one more particular aspect the present invention provides a method for performing a localised RCA reaction comprising at least two rounds of RCA, wherein the product of a second RCA reaction is attached, and hence localised, to a product of a first RCA reaction, said method comprising:

(a) providing a first RCA product which is immobilised on a solid support;

(b) directly or indirectly hybridising to said first RCA product a probe which comprises or provides a primer for a second RCA reaction;

(c) washing to remove any unbound probes (probes which have not hybridised); and (d) performing a second RCA reaction using said RCA primer of (b) to form a second RCA product, wherein in said reaction:

(i) said probe and said primer are not able to prime extension using said first RCA product as template or any such extension is limited to avoid displacement of any probe hybridised to the first RCA product; preferably wherein said probe comprises one or more modified regions and/or blocking oligonucleotides are used;

(ii) the direct or indirect hybridisation of the RCA primer of (b) to the first RCA product is maintained and, by virtue of said hybridisation, the second RCA product is attached to the first RCA product;

(iii) a RCA template for said second RCA reaction is comprised in or provided by the probe, or is separately provided.

Another representative embodiment of the method of the invention is depicted in FIG. 2. This embodiment represents a method which may be carried out in a homogenous, in solution, format without a solid phase. It may be performed sequentially or simultaneously. The probe comprises a binding domain (i) and a primer domain (ii) located at the respective 5' and 3' ends of the probe. The domains are complementary to each other (with non-complementary sequences in between) and are hybridised together to form a hairpin structure. The binding domain is complementary to a corresponding binding site present in each monomer of the first RCA product (or in an intermediate molecule), and upon contact with the first RCA product (or an intermediate molecule), hybridises to its binding site, causing the hairpin to open. It will be understood in this regard that the probe can be designed such that the competing hybridisation to the binding site on the target molecule is stronger than to the primer domain, such that in the presence of the target molecule (first RCA product or intermediate molecule) the hairpin is opened. Alternatively, or additionally, the probe may be designed such that the binding domain (i) is contained in the loop region and hybridisation of the probe to its target binding site causes the hairpin to open. Opening of the hairpin structure releases a free 3' end of the probe which is available to act a primer (the primer domain). Thus, the primer for the second RCA reaction is only made available, or released, upon hybridisation of the probe to the first RCA product. Accordingly, the probe is designed to protect the primer from binding to the second RCA template until the probe has hybridised to the first RCA product.

The released primer domain hybridises to a circular template for the second RCA reaction and primes the second RCA reaction. It will be seen that this embodiment may be modified to use a circularisable second RCA template, in which case, the probe also comprises a ligation template domain (iv). The primer domain (i) may thus also function as a ligation template domain.

In a further modification of the method shown in FIG. 2, the second RCA template may hybridise to the probe in such a manner as to leave a free 3' end which may be cleaved back to create a primer e.g. by an exonuclease activity. In such an embodiment, the primer domain does not lie at the 3' end of the probe, but may for example be located in the loop region.

To prevent unwanted extension using the first RCA product as template, the above strategies are available. Thus, an exonuclease-deficient polymerase may be used, or the probe may contain an exonuclease block, e.g. between the 3' end of the primer domain and the hybridised region (binding domain). Alternatively blocking oligonucleotides may be used.

It will be appreciated from the above description of FIG. 2 that the second RCA template may contain a region of complementarity (to the primer domain) which is also complementary to the first RCA product. Any undesired hybridisation of the RCA template to the first RCA production can be minimised by appropriate design of reagents and/or reaction conditions, for example by taking advantage of differential stability of intra-versus inter-molecular hybrids, differences in hybrid length, and possible introduction of mismatches to destabilise undesired hybrids.

Accordingly, in a further more particular aspect the present invention provides a method for performing a localised RCA reaction comprising at least two rounds of RCA, wherein the product of a second RCA reaction is attached, and hence localised, to a product of a first RCA reaction, said method comprising:

(a) providing a first RCA product;

(b) directly or indirectly hybridising to said first RCA product a probe comprising a hairpin structure which upon said hybridisation is unfolded to release a primer domain capable of functioning as a primer for a second RCA reaction;

(c) performing a second RCA reaction using said RCA primer of (b) to form a second RCA product, wherein in said reaction:

(i) said probe and said primer are not able to prime extension using said first RCA product as template or any such extension is limited to avoid displacement of any probe hybridised to the first RCA product; preferably wherein said probe comprises one or more modified regions and/or blocking oligonucleotides are used;

(ii) the direct or indirect hybridisation of the RCA primer of (b) to the first RCA product is maintained and, by virtue of said hybridisation, the second RCA product is attached to the first RCA product;

(iii) a RCA template for said second RCA reaction is comprised in or provided by the probe, or is separately provided.

In one embodiment a circular or circularisable second RCA template is separately provided, and when said RCA template is circularisable it is further preferably circularised by ligation using a ligation template comprised on or provided by said probe.

A further representative embodiment is depicted in FIG. 3. This is a further solid phase embodiment, in which a first RCA product is immobilised on a solid support. This embodiment requires two probes to be hybridised to the first RCA product directly or indirectly (directly is shown), and ligated together to form a ligation template for circularisation of added one or more added oligonucleotides to form a circular template for the second RCA. One of the probes is a probe according to the invention, and the other probe is a second probe which contains a second binding domain, hybridising to a different binding site on the first RCA product, and a ligation template domain or a domain comprising a region of complementarity to a circularisable RCA template. Thus the (first) probe of the invention comprises a binding domain at its 5' end and a primer domain at its 3' end, and a domain comprising a region or regions of complementarity to one or more oligonucleotides which together constitute a circularisable RCA template (two added oligonucleotides are shown in FIG. 3). These regions of complementarity may constitute a ligation template domain (as shown). The second probe comprises a binding domain at its 3' end and a ligation template domain or a region of complementarity to the one or more added oligonucleotides. The added oligonucleotides are able to hybridise to the probes with their ends juxtaposed for ligation. Thus, as shown in FIG. 3, the second probe comprises a ligation-template domain for the added oligonucleotides. A ligation step is performed which ligates the two probes together, thereby stabilising their hybridisation to the first RCA product. Ligation also serves to join together and circularise the added oligonucleotides to form or generate a circular RCA template for the second RCA. A washing step is performed to remove unbound (un-hybridised probes). Thus in the absence of first RCA product the probes are washed away and the probe is not available to prime a second RCA reaction (nor indeed are probes available to generate an RCA template). Such a washing step may take place before or after the oligonucleotides for circularisation are added, but before ligation and/or initiation of RCA.

To prevent unwanted extension on the first RCA product as template, the probes (specifically the first, primer-providing probe) may comprise an exonuclease block, as earlier described, or an exonuclease-deficient polymerase may be used. To prevent extension of any hybridised or unligated 3' ends of the second probe a stringent washing step may be included after the ligation step to remove any unligated probes. Alternatively or additionally the hybridised 5' end of the (first) probe may include a displacement block (i.e. a displacement block may be included in the binding domain of the probe of the invention). Alternatively or additionally blocking oligonucleotides may be used.

Modifications may be made to the method as depicted in FIG. 3. For example, the two oligonucleotides might be replaced by a single circularisable RCA template, and ligation to circularise the template might be ligated by one or other of the probes, e.g. the second probe may comprise a ligation template domain for circularisation. Alternatively, the two oligonucleotides may be replaced by three or more or oligonucleotides, hybridising to and in juxtaposition for ligation on the two probes. In a further modification, the probes need not be ligated together. In such an embodiment, the hybridised end of the second probe will be blocked from extension and/or displacement, The hybridised 5' end of the first probe may include a displacement block, and/or a blocking oligonucleotide may be used, hybridising between the two probes. In a still further modification, the primer domain need not be located at the very 3' end of the probe, and exonuclease digestion may be used to cleave back to release the primer.

Accordingly, a further more particular aspect the present invention provides a method for performing a localised RCA reaction comprising at least two rounds of RCA, wherein the product of a second RCA reaction is attached, and hence localised, to a product of a first RCA reaction, said method comprising:

(a) providing a first RCA product which is immobilised on a solid support;
(b) directly or indirectly hybridising to said first RCA product a (first) probe which comprises or provides a primer for a second RCA reaction, and a second probe, said second probe optionally being hybridised in juxtaposition for ligation directly or indirectly to the first probe, wherein said probes each comprise at least one binding site complementary to a cognate binding site in one or more RCA template oligonucleotides, which oligonucleotides are ligatable together to form a circular RCA template for a second RCA reaction;
(c) hybridising to said probes the said one or more RCA template oligonucleotides, wherein said oligonucleotides are hybridised in juxtaposition for ligation to circularise the oligonucleotides;
(d) performing a ligation step to ligate together and circularise said RCA template oligonucleotides thereby generating a circular RCA template for a second RCA reaction, and optionally ligating together said probes;
(e) washing one or more times to remove any unbound probes (probes which have not hybridised) and/or unligated probes, wherein to remove unbound probes said washing step may be performed before or after step (c) and to remove any unbound and unligated or any unligated probes, washing may be performed after step (d);
(f) performing a second RCA reaction using said circular RCA template and said RCA primer of (b) to form a second RCA product, wherein in said reaction:
    (i) said probes and said primer are not able to prime extension using said first RCA product as template or any such extension is limited to avoid displacement of any probe hybridised to the first RCA product; preferably wherein said probes comprises one or more modified regions and/or blocking oligonucleotides are used;
    (ii) the direct or indirect hybridisation of the RCA primer of (b) to the first RCA product is maintained and, by virtue of said hybridisation, the second RCA product is attached to the first RCA product.

As noted above, in one advantageous aspect the probe of the invention is a so-called RCA reporter probe which comprises or provides all of the nucleic acid components (or substrates) required for an RCA reaction, notably a primer and a RCA template. The RCA template may be in circular or circularisable form, and if circularisable it will need to be circularised prior to RCA. In such an embodiment one or more ligation templates will be required for circularisation, and will also be comprised in or provided by the probe.

Accordingly in one preferred aspect, the present invention provides a method for performing a localised RCA reaction comprising at least two rounds of RCA, wherein the product of a second RCA reaction is attached, and hence localised, to a product of a first RCA reaction, said method comprising:

(a) providing a first RCA product;
(b) directly or indirectly hybridising to said first RCA product a probe (more particularly a RCA reporter probe) which comprises or provides the following nucleic acid components for an RCA reaction:
    (i) a primer for a second RCA reaction;
    (ii) a circular or circularisable RCA template for the second RCA reaction; and; where said RCA template is circularisable
    (iiii), a ligation template for circularisation of said RCA template;
    wherein said probe is cleavable and/or unfoldable to release at least the primer to enable an RCA reaction to be performed;
(c) cleaving and/or unfolding the probe to release the primer, and optionally the RCA template, and the ligation template if present;
(d) where said RCA template is circularisable, performing a ligation step to circularise the RCA template;
(e) performing a second RCA reaction using said RCA primer and RCA template of (b) to form a second RCA product, wherein in said reaction:
    (i) said probe and any unfolded or cleaved part thereof (e.g. any of the nucleic acid components comprised in or released from the probe) are not able to prime extension using said first RCA product as template or any such extension is limited to avoid displacement of any probe hybridised to the first RCA product;
    (ii) the direct or indirect hybridisation of the RCA primer of (b) to the first RCA product is maintained and, by virtue of said hybridisation, the second RCA product is attached to the first RCA product.

Advantageously, the RCA components provided by the probe are unavailable for a RCA reaction until the probe has been cleaved and/or unfolded, i.e. at least one of the components of the RCA reaction must be released by unfolding the probe and/or a cleavage of the probe before the RCA reaction can take place. Thus, such a "single" or "self-contained" probe the has the effect of reducing the number of distinct initial nucleic acid components added to the reaction to achieve RCA, i.e. decreasing the complexity of the initial components present in the method whilst retaining the advantages associated with RCA assays. The use of such a single probe may also help to simplify assays to reduce errors and inefficiencies that arise from a large number of steps, e.g. handling errors, and to reduce costs and reaction times. Further by reducing the number of components in an assay, the number of potential interactions between components in the sample may be minimised, whilst maintaining multiple specific interactions that contribute to the specificity and selectivity of the assay, i.e. the use of such probes may allow to be retained the multiple processing steps that yield the specificity but without having to add more components or steps to the assay.

More particularly, the RCA nucleic acid components provided by (i.e. comprised as part of or generated from) the probe are able to initiate a RCA reaction following hybridisation to the first RCA product and cleavage and/or unfolding of the probe. Accordingly, the probe achieves specificity through a number of precise interactions without increasing the number of components to be added to the reaction.

At its broadest, an RCA reporter probe for use in the method of the invention may be defined a probe which provides or is capable of providing nucleic acid components for a RCA reaction (more particularly nucleic acid components sufficient to initiate a RCA reaction), said probe being a nucleic acid construct comprising:

(i) one or more domains binding domains capable of binding (e.g. hybridising) to (or more particularly one or more domains comprising a region of complementarity to) a first RCA product or to an intermediate molecule bound, (e.g. hybridized) directly or indirectly, to the first RCA product;

(ii) one or more domains together comprising or capable of providing a circular or circularisable RCA template;

(iii) a domain comprising or capable of providing a primer for RCA of said RCA template, wherein said domain hybridizes to a region of said circular or circularisable RCA template; and, when said RCA template is circularisable, (iv) one or more domains comprising or capable of providing a ligation template that templates the ligation (or circularisation) of the circularisable RCA template;

wherein at least part of the probe must be cleaved and/or unfolded to release said primer to enable said RCA.

It will be understood that each probe generates a single circular RCA template (for the second RCA reaction). Thus, it will be understood that in part (ii), where more than one domain provides a circular or circularisable RCA template, each such domain may contribute a part or portion of the ultimate RCA template, which parts or portions are ligated together to form the circle. Accordingly part (ii) may alternatively be expressed as:

(ii) a domain which comprises or provides a circular or circularisable RCA template, or two or more domains which together are capable of providing a circularisable RCA template.

Advantageously in preferred embodiments, the probe is unable to generate a RCA product unless the probe is bound to said first RCA product or intermediate molecule, i.e. the probe may be viewed as a target-dependent RCA probe, i.e. a RCA product is generated only in the presence of a target molecule, this being the ultimately the first RCA product, although in the case of the binding target for the probe, this may be the first RCA product or the intermediate nucleic acid molecule. For instance, in the case of the RCA reporter probe the primer and/or circular or circularisable RCA template may be unable to participate in, or initiate, the RCA reaction because, in the absence of the first RCA product (or intermediate nucleic acid molecule), the RCA nucleic acid components released from the probe are not in sufficient proximity to enable a RCA reaction to proceed, e.g. the probe may rely on a target-dependent ligation reaction to generate a RCA product. In some embodiments the primer and/or circular or circularisable RCA template may be inaccessible (e.g. unavailable) for a rolling circle amplification reaction when the probe is not bound to said first RCA product or intermediate molecule, e.g. the probe may rely on a target-dependent cleavage and/or unfolding to release one or more RCA nucleic acid components.

Target-dependent probes, i.e. probes that require an interaction with the target (first RCA product or intermediate molecule) to generate a RCA product, may be particularly useful in, but not limited to, homogeneous reactions. Probes that do not rely on an interaction with the target nucleic acid molecule to generate a RCA product are particularly useful in heterogeneous assays, in which probes and/or RCA products that are not bound to target nucleic acid molecules (e.g. excess probes or non-bound products) may be removed from the sample, e.g. by washing, prior to detection of the RCA product.

In some embodiments, the primer and ligation template may be provided by the same part of the probe, i.e. the same domain/sequence may function as the primer and ligation template. It will be evident that in embodiments that utilise a circularisable RCA template, the RCA template must be ligated to form a circular nucleic acid molecule in order that it can function as a template for RCA, i.e. in a probe dependent ligation.

It will be apparent from the description below that there are a large number of RCA reporter probe permutations and it is not feasible to provide a detailed description of each embodiment. Nevertheless, some exemplary embodiments are described below and it will be clear that other probes that fall within the scope of the claimed invention may be produced by combining features of these exemplary embodiments and this is readily achievable by a person of skill in the art, based on the description of the invention herein.

The probes of the invention are formed of one or more nucleic acid molecules or oligonucleotides, i.e. one or more nucleic acid strands, e.g. one, two, three or more nucleic acid strands or oligonucleotides. Accordingly, whilst the probe of the invention may be viewed as a single nucleic acid molecule, it may more appropriately be considered to be a nucleic acid construct, wherein when the probe comprises more than one nucleic acid strand (or oligonucleotide), each strand (or oligonucleotide) comprises a region of complementarity to at least one other strand (or oligonucleotide) in the construct such that the strands (oligonucleotides) are prehybridized (hybridized before the probe is contacted with a sample, i.e. each nucleic acid strand (oligonucleotide) of the probe is not added to the sample separately) so that the probe may be provided as a single nucleic acid construct. Thus, the probe of the invention may be a single stranded nucleic acid molecule (i.e. a continuous nucleic acid strand), comprising at least two hairpin structures, which are defined in detail below. Whilst the hairpin structures form regions in the probe that are double stranded, the probe may be regarded as single stranded because it is formed of a single continuous nucleic acid molecule, i.e. all of the nucleotides in the molecule are joined by covalent bonds, i.e. phosphodiester linkages.

In other embodiments, the probe may be a partially double stranded nucleic acid molecule, i.e. comprising at least two nucleic acid strands that are joined by one or more regions of complementarity (by hydrogen bonds, i.e. standard base pairing, as described below), wherein at least part of at least one of the nucleic acid strands is single stranded. In some embodiments, at least one of the strands of the partially double stranded construct is a circle or pre-circle (i.e. circularisable) oligonucleotide (a RCA template). In some embodiments, one strand of the partially double stranded molecule comprises at least one hairpin structure and a second strand is provided as an oligonucleotide that is hybridized to a part of the first strand that does not form a hairpin structure. More than two nucleic acid strands may be hybridized together to form a probe of the invention, e.g. 3, 4, 5 or more nucleic acid strands.

The representative descriptions given below of the RCA reporter probes and how they generate a RCA product illustrate the features required by the probes and the variation with which the features may be incorporated into a probe design.

One of the simplest forms of a RCA reporter probe is depicted in FIG. 4. The probe is in the form of a nucleic acid construct comprising two nucleic acid strands and is referred to herein as a type of "circle RCA probe" as defined below.

The first nucleic acid strand comprises two domains that each have binding site for, specifically a region of complementarity to, the target nucleic acid molecule, namely the first RCA product or intermediate molecule (so-called target complementary domains, binding domains or target recognition domains). The target complementary domain ("binding domain") at the 5' end of the first nucleic acid strand is used to secure (i.e. attach) the RCA product to the target nucleic acid molecule (first RCA product or intermediate molecule). The binding domain at the 3' end of the first nucleic acid strand comprises a sequence that is recognised by a cleavage enzyme when bound to the target nucleic acid molecule, i.e. the domain comprises a cleavage recognition site, i.e. a site or domain that may be cleaved or result in the cleavage of an adjacent site or domain in the probe. The binding domains are linked by a domain that comprises a region of complementarity to the RCA template (a circular nucleic acid molecule in this embodiment). Thus, the sequence (or region) linking the (target complementary) binding domains may be viewed as comprising a RCA template complementary domain or RCA template binding domain. This domain will form at least part of the primer for RCA and therefore may be viewed as a primer domain (i.e. the RCA primer domain). Accordingly, the first nucleic acid strand of the probe may be referred to as the "primer strand", i.e. the RCA primer is provided by, or generated from, the first strand.

The second nucleic acid strand is in the form of a circular nucleic acid molecule (RCA template) that is hybridized to at least part of the primer domain (i.e. hybridized to the RCA template complementary domain part of the primer domain). Thus, the second nucleic acid strand may be referred to as the "RCA template strand", "template strand" or "circle strand". As discussed below in more detail, it will be evident that in some embodiments the RCA template may be a circularisable nucleic acid molecule (or circularisable oligonucleotide), e.g. effectively a padlock probe (for the primer strand). Accordingly, the primer domain (e.g. the RCA template complementary) domain part of the primer domain) may template the ligation of the circularisable RCA template. Hence, the primer domain and/or the RCA template binding domain may also be viewed as a ligation template domain.

In the presence of the first RCA product (or intermediate nucleic acid molecule) (i.e. the target molecule), the binding domains of the probe hybridize to their cognate (target) binding sites in the nucleic acid molecule (probe binding sites). Hybridization of the probe and target forms a "functional" cleavage recognition site (FIG. 4A). In the presence of an enzyme that recognizes the cleavage recognition site, specifically an endonuclease which cleaves only one strand, such as a nickase, the first strand of the probe is cleaved, which results in the release of an extendable 3' end that is not hybridized to the target nucleic acid molecule (i.e. a single stranded domain) (FIG. 4B). This 3' extendable end may be complementary to the RCA template. Alternatively, the single stranded part of the first strand of the probe may be degraded, e.g. by exonuclease digestion. In either case, cleavage of the primer strand (which may involve more than one cleavage event) results in the release of the primer domain, i.e. the RCA primer. The primer domain is extended using the RCA template as a template for polymerisation to generate the second RCA product which is secured, or attached, to the target nucleic acid (first RCA product or intermediate molecule) by the 5' target complementary binding domain of the probe (FIG. 4C).

To inhibit or prevent unwanted extension using the first RCA product as template, the 3'end binding domain (which is hybridised to the first RCA product) may comprise an extension block. The primer domain may comprise an exonuclease block (for example between the 3' end of the primer and the 5' binding domain). The 5' binding domain may include a displacement and/or extension block etc. Alternatively or additionally blocking oligonucleotides may be used.

Another exemplary embodiment of an RCA reporter probe of the invention is depicted in FIG. 5, which depicts a type of "hairpin RCA probe", as defined below. The probe is in the form of a first nucleic acid strand that has a hairpin structure, which comprises a cleavage recognition site (as shown, in the loop region). The first nucleic acid strand is capable of providing the nucleic acid components sufficient to initiate a RCA reaction, i.e. a primer, RCA template and ligation template can be generated from the first nucleic acid strand. In some variant embodiments the ligation template may be provided as part of the second nucleic acid strand. Accordingly, the first nucleic acid strand of the hairpin RCA probes may be viewed as the primer strand or RCA template strand, i.e. the first nucleic acid strand of the hairpin RCA probes always provides the primer and RCA template. The first strand comprises two target complementary domains (binding domains), one at each end, which hybridize to the target nucleic acid molecule (first RCA product or intermediate molecule). A second nucleic acid strand is hybridized to the first nucleic acid strand and the double stranded portion of the probe acts as a cleavage recognition site, e.g. a site or domain that is recognised by a cleavage enzyme. Accordingly, the second nucleic acid strand may be viewed as a cleavage strand.

In FIG. 5 the target complementary binding domains at each end of the probe are hybridized to the first RCA product or intermediate molecule. (which may comprise directly or indirectly adjacent probe binding sites, see e.g. FIG. 15A). Moreover, in some embodiments the binding domains of the probe may hybridize to the target nucleic acid molecule such that the 5' and 3' ends of probe are directly or indirectly ligatable, such that the probe may be ligated to form a circular nucleic acid molecule using the target nucleic acid molecule as a ligation template (see FIG. 6).

Following contact with a sample (i.e. reaction mix) under conditions that allow the probe to hybridize with its target nucleic acid molecule, one or more cleavage agents that recognize the cleavage recognition sites are added to the sample which results in the cleavage of at least two sites in the probe, i.e. the loop of the hairpin structure and the double stranded portion of the probe or a region adjacent thereto. Upon cleavage of the probe the hairpin structure is able to unfold to provide the RCA template (a circularisable nucleic acid molecule) that is attached to the target nucleic acid molecule via hybridization to a portion of the probe comprising a target complementary binding domain. In some embodiments, the portion of the probe to which the RCA template is hybridized (i.e. attached) may function as the primer for the RCA reaction (e.g. FIG. 6). In other embodiments the primer is provided by the portion of the probe that is attached to the target nucleic acid molecule via the other target complementary binding domain. In these embodiments, the same portion of the probe may provide both the primer and ligation template. However, it will be evident from the description below that the primer and ligation template may be provided as separate domains of the probe, e.g. the ligation template may be provided by the second nucleic acid strand of the probe.

In the presence of the target nucleic acid molecule, the RCA nucleic acid components are directly or indirectly hybridized to the target nucleic acid molecule (via the binding domains) thereby maintaining the RCA nucleic acid components in close proximity. The RCA template (circularisable nucleic acid molecule) hybridizes to both the primer and ligation template, which may be the same part of the probe nucleic acid construct. The ligation template part of the probe templates the circularisation of the RCA template in the presence of a ligase enzyme. The primer part of the probe can be extended using the circularised RCA template as a polymerisation template to generate the second RCA product. It will be evident that in the absence of a target nucleic acid molecule the cleaved parts of the probe that form the RCA nucleic acid components are not maintained in proximity, thereby preventing the production of a second RCA product in the absence of target nucleic acid (first RCA product or intermediate molecule).

To prevent or inhibit unwanted extension templated by the first RCA product, one or more exonuclease and/or extension and/or displacement blocks may be included, and/or blocking oligonucleotides used, based on the principles above. Thus for example, an extension block may be included in the 3' binding domain. A displacement block and/or extension block may be included in the 5' binding domain. An exonuclease block may be included in the primer domain (upstream or downstream of the 3' primer end, depending upon which part of the probe provides the primer).

The exemplary embodiments described above demonstrate that the RCA reporter probe of the invention may require two types of ligation events to enable a RCA reaction to proceed. In other embodiments, no ligation events are required. A first ligation event may be defined as a "target dependent ligation", wherein the binding domains of the probe may hybridize to its target nucleic acid molecule such that the 5' and 3' ends of probe are directly or indirectly ligatable using the target nucleic acid as a ligation (circularisation) template (see FIG. 6).

This may be particularly advantageous because it may allow the generation of the second RCA product to be target dependent, i.e. a second RCA product may be generated only in the presence of the first RCA product. For instance, the binding domains of the probe may be designed so that the RCA components generated by cleavage of the probe will remain bound to (i.e. attached to or hybridized to) the target nucleic acid molecule only if the ends of the probe have been directly or indirectly ligated by virtue of a target-templated ligation. This may be achieved, for example, by designing the probe to ensure that at least one of the target complementary binding domains may hybridize stably only in the presence of the other target complementary binding domain(s), e.g. at least one of the target complementary binding domains of the probe may be a short sequence. Prior to cleavage of the probe, the combination of the interaction of the target complementary binding domains (which are joined by the internal part of the nucleic acid molecule) with the target nucleic acid molecule is sufficient to attach the probe to the target nucleic acid. However, if the target complementary binding domains are not ligated (directly or indirectly), upon cleavage of the cleavable sites in the probe, at least one of the nucleic acid components of the probe required to enable RCA will dissociate from the target nucleic acid. Accordingly, the RCA reaction will not be able to proceed unless a target-templated ligation has occurred to secure (i.e. attach) all of the RCA nucleic acid components to the target nucleic acid in proximity (i.e. to stabilize the interaction of the probe target complementary binding domains with the target nucleic acid molecule).

A second ligation event may be defined as a "probe dependent ligation", wherein the RCA template is provided as a circularisable nucleic acid molecule (or as two or more "parts" or separate molecules which are ligatable together to form a circle) and its intramolecular (or intermolecular if more than one molecule is involved) ligation is templated by one or more domains of the probe, i.e. the ligation template domain(s) of the probe. A probe dependent ligation is essential in embodiments where the RCA template is provided by the probe by cleavage of a hairpin structure, e.g. a stem loop structure, i.e. hairpin RCA probes. However, a probe dependent ligation event may also be required for circle RCA probes if the RCA template strand is a circularisable nucleic acid molecule.

In some embodiments, the probe requires both a target-dependent ligation and a probe-dependent ligation, preferably wherein the probe-dependent ligation cannot occur unless there has been a target-dependent ligation, e.g. when part of the probe required for the probe-dependent ligation will dissociate from the target nucleic acid molecule after cleavage of the probe if a target-dependent ligation has not occurred.

It will be seen, therefore, that an RCA reporter probe of the invention may enable the method to proceed in controlled distinct (discrete or separable) stages. In practice it may be preferable to combine all or most of the reactants simultaneously, to allow the reaction to proceed without intervention. Nevertheless, an RCA reporter probe of the invention requires a sequence of events to occur in order to generate the second RCA product (which may in certain detection assay embodiments be indicative of the presence of a target nucleic acid molecule, and hence a target analyte, in a sample) and, in the embodiments described above, the sequence of events (i.e. stages of the reaction) can be considered as:

(i) binding of the probe to the target (first RCA product or intermediate) nucleic acid molecule (this may include unfolding the probe as described below) and optionally ligating the target complementary binding domains (i.e. a target-dependent ligation);

(ii) cleaving the cleavable site(s) in the probe (i.e. releasing at least one of the components of the RCA reaction);

(iii) optionally ligating the RCA template to circularise it (ligating the circularisable nucleic acid molecule or two or more RCA template molecules, i.e. a probe dependent ligation);

(iv) extending the RCA primer to form a second RCA product; and (v) optionally detecting the second RCA product (detecting the extended primer, which is part of the probe).

Thus, the reagents of the method (or assay) may be contacted with the target nucleic acid containing sample (i.e. the sample or reaction mixture containing the first RCA product, and optionally intermediate molecule) simultaneously without the generation of the second RCA product prior to cleavage and/or unfolding of the probe to release the nucleic acid components that are required to enable the second RCA. The provision of the nucleic acid components to enable RCA in the form of a single probe is advantageous and it is particularly beneficial that the single probe also allows the method to proceed in stages whilst enabling the addition of the method reagents simultaneously.

As described in more detail below, the present invention provides numerous RCA reporter probe variants. However, in its simplest form, the RCA reporter aspect of the invention can be seen to provide a single probe (a nucleic acid construct) that interacts directly or indirectly with the first RCA product and provides the nucleic acid components that are necessary and sufficient to enable a second RCA reaction following cleavage and/or unfolding of the probe (i.e. the RCA nucleic acid components form part of, and/or are generated from, the nucleic acid construct). Accordingly, as noted above, present invention may be seen as providing a single RCA probe or self-contained RCA probe. In particular embodiments the invention may be seen as providing an RCA reporter probe that must interact with a target nucleic acid and be cleaved and/or unfolded to release the components to enable a RCA reaction, e.g. a target nucleic acid molecule dependent RCA probe. The probe may also be viewed as a probe for target-dependent production of a second RCA product, wherein the sequence of the second RCA product is not related to the sequence of the first RCA product (i.e. the second RCA product does not comprise a sequence that has significant sequence identity to a first RCA product).

The RCA reporter probes of the invention may fall into one of two categories, depending on the form in which the RCA template is provided by the probe.

In a first category, the probes comprise a RCA template, i.e. the RCA template is provided as one of the nucleic acid strands of the nucleic acid construct, i.e. the RCA template is provided as a pre-formed circle oligonucleotide or pre-circle (i.e. circularisable) oligonucleotide. Accordingly, these probes may be referred to generally as circle or pre-circle RCA probes, or RCA template probes, wherein the term "circle RCA probes" may be used to refer both to probes comprising a circular and circularisable RCA template.

In a second category the probes provide a RCA template, i.e. the RCA template, or two or more parts thereof, is/are generated by the cleavage of the probe into multiple parts that are held in proximity by the binding domain of each part of the probe. Hence, these probes may be viewed as "multi-part probes", e.g. two-part, three-part probes etc. In some embodiments the RCA template is generated by cleavage of a hairpin structure, e.g. a stem loop domain. Accordingly, these probes may be referred to generally as hairpin or stem loop RCA probes. In other embodiments, the RCA template is generated by the cleavage of a linear domain i.e. a domain without intramolecular complementarity. Accordingly these probes may be referred to generally as linear RCA probes. Both hairpin RCA probes and linear RCA probes may be referred to as pre-RCA template probes or releasable RCA template probes.

Whilst both circle RCA probes, linear RCA probes and hairpin RCA probes may require a probe dependent ligation event to generate the RCA template, it is preferred that the RCA template of circle RCA probes is in the form of a preformed circle oligonucleotide. Hence, circle RCA probes also may be viewed as probe templated ligation independent RCA probes (although these probes may still be target templated ligation dependent probes). In contrast, the hairpin RCA probes and linear RCA probes require a probe dependent ligation event to form the RCA template and hence also may be viewed as probe templated ligation dependent RCA probes.

As discussed below, in some embodiments the circle RCA probes may comprise a hairpin or stem loop structure. However, the hairpin or stem loop structure in the circle RCA probes is not required to generate the RCA template. In contrast, one of the hairpin structures in the hairpin RCA probes will release the RCA template (i.e. the RCA template is generated from a hairpin structure in a hairpin RCA probe).

A variant of the "circle RCA probe" described above is shown in FIG. 19, in which the probe forms a hairpin structure when the target complementary binding domains bind to the target nucleic acid molecule, e.g. a stem loop structure forms in between the target complementary domains. The stem loop structure forms a cleavage domain, wherein cleavage of the probe releases the RCA primer. Thus, the probe requires a target dependent cleavage to release a RCA component, although the cleavage recognition site does not need to involve the target nucleic acid molecule directly.

Two further exemplary embodiments of "circle RCA probes" are shown in FIGS. 7 and 8, which are variants of the embodiment described above and shown in FIG. 4. Optionally, in these embodiments, the target complementary binding domains of the first nucleic acid strand (the primer strand) hybridize to the target nucleic acid molecule (first RCA product or intermediate molecule) such that the 5' and 3' ends of probe are directly or indirectly ligatable, such that the probe may be ligated to form a circular nucleic acid molecule using the target nucleic acid(s) as a ligation template.

The binding domain at the 3' end of the first nucleic acid strand comprises a sequence that is recognised by a cleavage enzyme when bound to the target nucleic acid molecule, i.e. the domain comprises a cleavage recognition site. Preferably, the cleavage recognition site is functional, i.e. recognized and cleaved by a cleavage enzyme, when the domain is double stranded. Many enzyme cleavage recognition sites comprise symmetrical, i.e. palindromic, sequences and this can be problematic when multiple single stranded molecules comprising the same cleavage site are present in a sample, i.e. probes comprising palindromic cleavage recognition sequences are likely to form duplexes that are substrates for the cleavage enzyme. Accordingly, if the cleavage recognition site comprises a symmetrical, i.e. palindromic, sequence, it may be advantageous to block the cleavage recognition sites to avoid target independent cleavage of the probe, which may result in the generation of RCA products in the absence of target nucleic acid (first RCA product) in the sample.

Thus, in some embodiments the probe may comprise a third nucleic acid strand, a protective or blocking strand (FIG. 7), that is capable of hybridizing to the cleavage recognition site such that it does not form a site that is recognized or cleaved by the cleavage enzyme, i.e. the protective strand (an oligonucleotide) is complementary to the region of the binding domain comprising the cleavage recognition site but does not form a functional cleavage domain or cleavable site. Hence, the protective or blocking strand is partially complementary to the cleavage recognition site. The protective strand must interact with (hybridize to) the cleavage recognition site more strongly than the interaction between the palindromic sequences of two probes, e.g. the protective strand may comprise a region of complementarity to the probe that is longer than the cleavage recognition site.

In the presence of the target nucleic acid molecule (first RCA product or intermediate molecule), the target complementary binding domains of the probe hybridize to their cognate or target site. The binding domain comprising the cleavage recognition site forms a more stable interaction with the target nucleic acid molecule than it does with the protective strand, which is displaced (i.e. the probe is "unfolded"). The duplex between the binding domain and the target nucleic acid molecule forms a functional cleavage recognition site which may be cleaved by a cleavage enzyme, e.g. an endonuclease such as a nickase, or result in the cleavage of a sequence adjacent to the cleavage recognition site in the probe. In the presence of an enzyme that recognises the cleavage recognition site, the first strand of the probe is cleaved, which results in an extendable 3' end that is not hybridized to the target nucleic acid molecule (i.e. a single stranded domain). The single stranded part of the first strand of the probe may be degraded, e.g. by exonuclease digestion, and thereby results in the release of the primer domain. The primer domain is extended using the circular nucleic acid molecule (RCA template) as a template for polymerisation to generate the second RCA product which is attached to the first RCA product by hybridisation (more particularly to the first RCA product or intermediate nucleic acid molecule by the 5' target complementary binding domain of the probe).

In some embodiments, the RCA template (i.e. the circle strand) may act as a protective or blocking strand (FIG. 8). When the probe interacts with the target nucleic acid molecule to form the functional cleavage site, the RCA template is displaced to another region of the first nucleic acid strand (the primer strand), which is also complementary to the RCA template (the so-called displacement region or domain). This displacement may be viewed as an unfolding step. The RCA template interacts with the target complementary binding domain of the probe that comprises the cleavage recognition site more strongly than the displacement region of the probe, such that the RCA template is only displaced (the probe is only unfolded) when the probe interacts with the target nucleic acid sequence.

In some embodiments, the cleavage recognition site is not a symmetrical sequence. Accordingly, a blocking or protective strand may not be required.

Unwanted extension templated by the first RCA product may be inhibited or prevented by using blocks and/or blocking oligonucleotides, based on the principles and analogously to as described above. For example 3' binding domains may incorporate extension blocks. 5' binding domains may contain a displacement block and/or an extension block. The probe may contain an exonuclease block between the 3' primer end and the binding domain (5' binding domain) etc.

Still further embodiments of the circle RCA probes are shown in FIGS. 9 and 10 In these exemplary embodiments, both the primer strand and the circle strand are circular oligonucleotides. The primer strand comprises a target complementary binding domain, which forms a functional cleavage recognition site when it hybridizes to the target nucleic acid molecule. In some embodiments, a cleavage enzyme that recognises the cleavage recognition site is able to cleave the primer strand at a site adjacent to the cleavage recognition site, e.g. using a Type IIS restriction endonuclease. This is particularly useful to avoid cleavage of the target nucleic acid molecule (first RCA product or intermediate molecule). The site at which cleavage of the primer strand occurs (the cleavable domain) may be formed by a restriction oligonucleotide (defined below), which forms a third strand of the nucleic acid construct, i.e. a restriction strand or cleavage strand (FIG. 9). Alternatively, the primer strand may comprise a hairpin structure that forms a cleavable domain (FIG. 10). As described above, cleavage of the primer strand of the RCA probe, and subsequent exonuclease degradation, releases the primer which can be extended by RCA template dependent polymerisation to form the second RCA product. In some embodiments exonuclease degradation is not required and cleavage of the primer strand may release directly a portion of the primer strand that can function as a primer for the second RCA reaction.

Again blocks and/or blocking oligonucleotides may be used to prevent or inhibit unwanted extension using the first RCA product as template. For example an exonuclease block may be include in the region of the primer strand between the 3' end of the primer and the binding domain. The binding domain may include a displacement block and/or extension block etc.

A still further exemplary embodiment is shown in FIG. 11. The probe provides a first nucleic acid strand, the primer strand, which in some embodiments may be in the form of a hairpin structure. In other embodiments, the primer stand may be in the form of a circular oligonucleotide (FIG. 12). The probe also provides a second nucleic acid strand, the circle strand, which is in the form of a circular nucleic acid molecule that is hybridized to a region of the first nucleic acid strand, e.g. the single stranded loop of the hairpin structure (FIG. 11).

Before the probe interacts with, e.g. hybridizes to, the target nucleic acid molecule (first RCA product or intermediate molecule), the 3' end of the first nucleic acid molecule/strand (or a part of the nucleic acid molecule located towards the 3' end) may be hybridized to at least part of the 5' end of the first nucleic acid strand (i.e. to at least part of the binding domain) so as to form a hairpin structure, e.g. a stem loop. This may act to protect one or both ends of the primer strand from degradation, e.g. digestion by components in the sample with exonuclease activity. However, it is not essential that the first nucleic acid strand of the probe forms a hairpin structure, i.e. in some embodiments the primer strand may comprise no intramolecular complementarity.

In the presence of the first RCA product or intermediate molecule (i.e. the target nucleic acid molecule), the target complementary binding domain of the primer strand hybridizes to its cognate or target site. Where the primer strand of the probe is provided in the form of a hairpin structure, the interaction between the probe and the target nucleic acid is sufficient to destabilize the hairpin structure, i.e. the duplex between the target complementary binding domain of the primer strand and the target nucleic acid is more stable than the duplex between the 5' and 3' ends of the primer strand. For instance, the duplex between the binding domain of the primer strand and the target nucleic acid may be longer than the duplex between the 5' and 3' ends of the primer strand.

The primer strand comprises a cleavage site that forms part of, or is adjacent to, the site at which the RCA template is hybridized (i.e. 3' to the site at which the RCA template is hybridized). Cleavage of the cleavage site, e.g. by exonuclease degradation of the 3' of the primer strand, results in the release of the RCA primer, which can be extended using the RCA template strand as a polymerisation template to generate the second RCA product.

Again unwanted extension using the first RCA product as template can be avoided by using blocks and/or blocking oligonucleotides as discussed above. Thus the binding domain may contain an extension and/or displacement block. The primer strand may contain an exonuclease block between the 3' end of the primer and the binding domain etc.

A further circle RCA probe exemplary embodiment is shown in FIG. 13, wherein the probe comprises three nucleic acid strands: a primer strand, circle strand and an invasion strand (which may also be viewed as a blocking strand).

In a preferred embodiment the primer strand comprises a target complementary binding domain at the 5' end and a domain at the 3' end comprising a cleavage recognition site (a cleavage domain), which are joined by an internal region of complementarity to the RCA template (the RCA template complementary domain) which may also be viewed as the primer domain or a part thereof). The cleavage domain comprises a region of sequence that is similar or identical to a region of the target sequence (the region of the target sequence directly or indirectly adjacent to the region to which the target complementary region (binding domain) of the primer strand is able to hybridize).

At its 5' end the invasion strand comprises a region of complementarity to the cleavage domain and at its 3' end comprises a target complementary binding domain, wherein the region of complementarity to the cleavage domain is also complementary to a region of the target sequence (the region of the target sequence directly or indirectly adjacent to the region to which the target complementary binding domain of the primer strand is able to hybridize). The invasion strand prevents, i.e. blocks, the cleavage domain from cleavage by a cleavage enzyme, e.g. an exonuclease.

In the presence of the target nucleic acid molecule (first RCA product or intermediate molecule), the target complementary regions (binding domains) of the probe bind to the target molecule (the probe binding domains of the target molecule). This displaces the invasion strand from the cleavage domain, i.e. the probe unfolds and the invasion strand invades the target nucleic acid, which exposes the cleavage domain to the cleavage enzyme, wherein cleavage of the domain (e.g. degradation of the single stranded 3' end of the probe up to the primer domain, to which the RCA template is hybridized) releases the primer for RCA templated extension to form the second RCA product.

In some embodiments, the primer strand does not comprise a cleavage domain. Instead, the primer strand comprises a target complementary region (binding domain) at the 5' end, a first region of complementarity to the RCA template (the RCA template complementary domain) and a second region of complementarity to the RCA template; the second domain functions as the primer for the RCA reaction (the primer domain). The primer domain comprises a region of sequence that is similar or identical to a region of the target sequence (the region of the target sequence directly or indirectly adjacent to the region to which the target complementary binding domain of the primer strand is able to hybridize). The primer domain hybridizes more strongly to the invasion strand than it does to the RCA template.

In the presence of the target nucleic acid molecule, the target complementary regions (binding domains) of the probe bind to the target molecule. This displaces the invasion strand from the primer domain, i.e. the probe unfolds and the invasion strand invades the target nucleic acid, which releases the primer domain to bind to the RCA template for RCA templated extension. Hence, the primer may be released by target-dependent unfolding of the probe.

Unwanted extension templated by the first RCA product may be avoided by appropriate use of blocks and/or blocking oligonucleotides as discussed above. For example the domains may include displacement and/or extension blocks, an exonuclease block may be included between the 3' primer end and the binding domain, and/or blocking oligonucleotides may be used etc.

Thus, in a more particular aspect of the invention, an RCA reporter probe of the present invention may be defined as a probe which provides or is capable of providing nucleic acid components sufficient to initiate a rolling circle amplification (RCA) reaction, said probe being a nucleic acid construct comprising:

(a) a first strand (i.e. a primer strand) comprising:

(i) a first domain comprising a binding domain capable of binding to (more particularly comprising a region of complementarity to) a first RCA product or an intermediate molecule bound (e.g. hybridized), directly or indirectly, to the first RCA product (i.e. a target-complementary or target-binding, or more simply binding domain);

(ii) a second domain comprising a region of complementarity to a circular or circularisable RCA template, which domain may provide all or part of a primer for RCA of said RCA template (i.e. a RCA template complementary domain and/or primer domain); and (iii) a third domain comprising a cleavage recognition site (i.e. a cleavage domain) or comprising a region of complementarity to a circular or circularisable RCA template which may provide a primer for RCA of said RCA template (i.e. a primer domain), and (b) a second strand (i.e. a circle strand) that is capable of hybridizing to the second domain of the first strand, said second strand comprising:

(i) a circular RCA template comprising at least one region of complementarity to the first strand (i.e. at least the second domain of the first strand); or (ii) a circularisable RCA template comprising two regions of complementarity to the second domain of the first strand, wherein the first region of complementarity is at the 5' end of the circularisable RCA template and the second region of complementarity is at the 3' end of the circularisable RCA template, and wherein said regions of complementarity are capable of hybridizing to the second domain of the first strand such that the 5' and 3' ends are directly or indirectly ligatable, wherein cleavage and/or unfolding of at least part of the probe releases a domain to function as the primer for RCA of the RCA template.

In some embodiments of this aspect of the invention, the third domain of the primer strand comprises a region of complementarity to the first domain, such that the third domain and first domain hybridize to form a nucleic acid duplex when the first domain is not hybridized to the first RCA product or the intermediate molecule. Thus, contacting the probe with the target nucleic acid molecule may be viewed as unfolding the probe. This embodiment may be particularly advantageous to prevent the cleavage of the probe when it is not bound to the target nucleic acid molecule, e.g. wherein the cleavage agent is an exonuclease, particularly a 3' exonuclease.

In some embodiments, the nucleic acid construct comprises a protection strand or protection oligonucleotide. The protection strand or oligonucleotide may prevent or protect the cleavage recognition site or domain of the oligonucleotide from being recognized by the cleavage enzyme. In some embodiments, the protection strand or oligonucleotide may prevent the primer strand from forming a functional cleavage recognition site with another nucleic acid molecule in a sample, e.g. with another probe. In yet other embodiments, the protection strand or oligonucleotide may prevent the primer strand from priming RCA templated extension. In some embodiments, the RCA template functions as a protection strand or oligonucleotide. In some embodiments, the ends of the primer strand may be directly or indirectly ligated.

In some embodiments, the primer strand is a circular nucleic acid molecule. In yet further embodiments, the circular primer strand comprises a hairpin structure. In some embodiments, the nucleic acid construct comprises a restriction oligonucleotide (i.e. a restriction strand or cleavage strand).

A further exemplary embodiment of a "hairpin RCA probe" is shown in FIG. 14, which is a variant of the embodiment described above and shown in FIG. 5.

The probe is in the form of a first nucleic acid strand that comprises a hairpin structure and two further nucleic acid strands (second and third strand, i.e. oligonucleotides) that are hybridized to the first nucleic acid strand on either side of the hairpin structure. The double stranded portions of the probe created by the second and third strands act as cleavage recognition sites, e.g. sites or domains that are recognised by one or more cleavage enzymes. Hence, the second and third strands may be referred to as cleavage strands or cleavage oligonucleotides. In some embodiments, these may be known as restriction oligonucleotides or restriction strands as defined below.

The first strand comprises three regions of complementarity to its target (i.e. three binding domains), wherein each target complementary binding domain is directly adjacent to a cleavage recognition site, i.e. directly adjacent to a region of the probe that forms the hairpin structure or a region to which a cleavage strand hybridizes. Each binding domain functions to attach one of the RCA nucleic acid components, directly or indirectly, to the first RCA product.

Following contact with a sample under conditions that allow the probe to hybridize with its target nucleic acid molecule (i.e. first RCA product or intermediate molecule), one or more cleavage agents that recognize the cleavage recognition sites may be added to the sample which results in the cleavage of three sites in the probe, i.e. the loop of the hairpin structure and each double stranded portion of the probe or a region adjacent thereto. Upon cleavage of the probe the hairpin structure is able to unfold (by cleavage of part of the hairpin structure) to provide the RCA template that is attached to the target nucleic acid molecule via hybridization to a portion of the probe comprising a target complementary binding domain. The primer and ligation template are each provided by the portions of the probe that are attached to the target nucleic acid molecule via the other target complementary binding domains.

In the presence of the target nucleic acid molecule, the RCA nucleic acid components are directly or indirectly hybridized to the first RCA product (via the target complementary binding domains) thereby maintaining the RCA nucleic acid components in close proximity. The RCA template hybridizes to both the primer and ligation template. The ligation template part of the probe templates the circularisation of the RCA template in the presence of a ligase enzyme. The primer part of the probe can be extended using the circularised RCA template as a polymerisation template to generate the second RCA product. It will be evident that in the absence of a target nucleic acid molecule the cleaved parts of the probe that form the RCA nucleic acid components are not maintained in proximity, thereby preventing the production of a second RCA product in the absence of target nucleic acid.

Extension, exonuclease, and/or displacement blocks and/or blocking oligonucleotides may be used analogously to as described above to avoid unwanted extension templated by the first RCA product. Thus for example, the binding domains may include displacement and/or extension blocks. Other regions of the first strand may include an exonuclease block etc.

In yet further embodiments, one or both of the primer and ligation template domains may be provided as hairpin structures, see e.g. FIGS. 15 and 16. It will be evident that the primer and ligation domains may be provided by a combination of hairpin structures and cleavage oligonucleotides. However, it may be particularly advantageous for all of the RCA nucleic acid components to be provided as hairpin structures because this allows the probe nucleic acid construct of the invention to be provided as a single stranded nucleic acid molecule, i.e. a single continuous nucleic acid strand that comprises regions of intramolecular complementarity.

Thus, in one embodiment of the invention the RCA reporter probe may be provided as a "two-part" hairpin RCA probe (FIG. 15). The probe is in the form of a single nucleic acid strand that comprises two hairpin structures, each comprising a cleavable site and linked to a target complementary binding domain. In FIG. 15 the probe comprises a target complementary binding domain at each end. It will be evident that the ends of the probe may hybridize to its target nucleic acid molecule (first RCA product or intermediate molecule) such that the 5' and 3' ends of probe are directly or indirectly ligatable, so that the probe may be ligated to form a circular nucleic acid molecule using the target nucleic acid as a ligation template.

Following contact with a sample under conditions that allow the probe to hybridize with its target nucleic acid molecule, a cleavage agent may be added to cleave the cleavage sites in the hairpin structures. The hairpin structures unfold to yield the nucleic acid components needed for the second RCA reaction. In one embodiment the primer and ligation template are provided by a first hairpin structure (i.e. the primer also functions as the ligation template, or vice versa) and the RCA template is provided by a second hairpin structure. In another embodiment, the ligation template is provided by a first hairpin structure and the primer and RCA template are provided by a second hairpin structure.

In the presence of the target nucleic acid molecule, and after cleavage of the probe, the primer and ligation template domains form part of the probe that comprise the target complementary binding domains. Accordingly, the primer and ligation template domains are hybridized to the target nucleic acid molecule thereby maintaining the RCA nucleic acid components in close proximity. The RCA template hybridizes to both the primer and ligation template. In embodiments where the primer domain also functions as the ligation template, the RCA template is hybridized to a portion of the probe comprising a target complementary domain. As described above, the ligation template part of the probe templates the circularisation of the RCA template in the presence of a ligase enzyme. The primer part of the probe can be extended using the circularised RCA template as a polymerisation template to generate the second RCA product. It will be evident that in the absence of a target nucleic acid molecule the cleaved parts of the probe that form the RCA nucleic acid components are not maintained in proximity, thereby preventing the production of a second RCA product in the absence of target nucleic acid (first RCA product or intermediate molecule).

A "three-part" probe is shown in FIG. 16, which is form of a single nucleic acid strand that comprises three hairpin structures, each comprising a cleavable site and linked to a target complementary binding domain. It will be evident that this probe functions similarly to the embodiment shown in FIG. 14 and described above. The difference is that the cleavage oligonucleotides are replaced by hairpin structures.

An exemplary embodiment of a two-part "linear RCA probe" is depicted in FIG. 17E, which is a variant of the embodiment described above and shown in FIG. 5.

The probe is in the form of two nucleic acid strands and comprises a single cleavage domain. A first strand provides the RCA template and the second strand may be viewed as the cleavage strand. In FIG. 17E the probe comprises a first target complementary binding domain at the 5' end and a second target complementary binding domain near the 3' end. Following contact with a sample under conditions that allow the probe to hybridize with the target nucleic acid molecule (first RCA product or intermediate molecule, a cleavage agent may be added to cleave the cleavage site between the binding domains. The parts of the probe that are not complementary to the target nucleic acid molecule form the nucleic acid components needed for the second RCA reaction. For instance, part of the probe that is attached to the first binding domain forms the ligation template and RCA primer. The second binding domain forms the RCA template, i.e. the ends of domains on either side of the second binding domain may bind to the ligation template such that they are directly or indirectly ligatable.

In the presence of the target nucleic acid molecule, and after cleavage of the probe, the ligation template/RCA primer and RCA template domains form part of the probe that comprise the target complementary binding domains. Accordingly, the ligation template/RCA primer domain and RCA template domain are hybridized to the target nucleic acid molecule thereby maintaining the RCA nucleic acid components in close proximity. As described above, the ligation template/RCA primer part of the probe templates the circularisation of the RCA template in the presence of a ligase enzyme. The ligation template/RCA primer part of the probe can be extended using the circularised RCA template as a polymerisation template to generate the second RCA product. It will be evident that in the absence of a target nucleic acid molecule the cleaved parts of the probe that form the RCA nucleic acid components are not maintained in proximity, thereby preventing the production of a second RCA product in the absence of target nucleic acid.

The "two-part" and "three-part" aspects of the hairpin RCA probes and linear RCA probes described above refer to the number of target complementary binding domains, wherein cleavage of the probe acts to disconnect the RCA nucleic acid components that are directly or indirectly attached to each target complementary binding domain. Accordingly, it will be evident that the "three-part" probes cannot be involved in a target-templated ligation, whereas this is a preferred aspect of the "two-part" probes.

Further examples of "two-part" probe designs are shown in FIG. 17. As described above, each hairpin RCA probe provides the nucleic acid components sufficient to initiate a RCA reaction, i.e. a primer, ligation template and RCA template and from the embodiments exemplified in the Figures it can be determined that a domain that provides a RCA template is adjacent to a domain that provides a ligation template. However, a domain that provides a primer can be adjacent to a domain that provides a RCA template or a domain that provides a ligation template.

It will be apparent that the "two-part" and "three-part" probes described above are exemplary and it is possible to provide the RCA components in more parts, e.g. 4, 5 parts etc. Hence, the linear and hairpin RCA probes may be multiple part probes, wherein each RCA component is attached to a separate target complementary binding domain after probe cleavage. In this respect, the RCA template may be provided in more than one part, e.g. two or three parts etc, which may be ligated to form a circular oligonucleotide. In this respect, the number of parts in which the RCA template is provided will determine the number of ligation templates provided by the probe, i.e. if the RCA template is provided in two parts, e.g. two half-circles, the probe will provide two ligation templates, wherein one of the ligation templates may also function as the RCA primer (e.g. a four-part probe) or the RCA primer may be provided separately (e.g. a five-part probe). Four-part and five-part probes are shown in FIG. 18.

Thus, in another more particular aspect of the invention, the RCA reporter probe may be defined as a probe which provides or is capable of providing nucleic acid components sufficient to initiate a rolling circle amplification (RCA) reaction, said probe being a nucleic acid construct comprising:

(i) at least two domains each comprising a binding domain capable of binding to (more particularly comprising a region of complementarity to) the first RCA product or an intermediate molecule bound, (e.g. hybridized) directly or indirectly to the first RCA product (i.e. at least two (target complementary) binding domains);

(ii) one or more domains together capable of providing a RCA template; and (iii) at least one domain capable of providing a ligation template and/or primer, said domain comprising;

(a) a region of complementarity to a sequence within the probe, such that it forms part of a hairpin structure that comprises a cleavage recognition site; or (b) a region of double stranded nucleic acid that comprises a cleavage recognition site, wherein (1) each domain capable of providing a RCA nucleic acid component may be directly or indirectly attached to the first RCA product via a binding domain;

(2) the domain capable of providing the RCA template is adjacent to the domain capable of providing the ligation template; and (3) cleavage of the probe releases (or is sufficient to release) (i.e. the probe is cleavable to release) said RCA nucleic acid components to enable a RCA reaction when the binding domains are hybridized directly or indirectly to the first RCA product (i.e. hybridised to the first RCA product or intermediate nucleic acid molecule).

In the hairpin RCA probe embodiments, the probe comprises one or more domains together capable of providing a RCA template, wherein one or more said domains comprise a region of complementarity to a sequence within the probe, such that it forms part of a hairpin structure that comprises a cleavage recognition site.

In some embodiments the target complementary binding domains hybridize to the target or intermediate nucleic acid molecule such that the 5' and 3' ends of the probe are directly or indirectly ligatable.

In some embodiments, the domain capable of providing the RCA template also provides the primer for the RCA reaction, in which case the domain capable of providing the ligation template and/or primer only provides the ligation template. Accordingly, in some embodiments the ligation template and primer domains are provided as separate domains.

In an exemplary embodiment, each RCA nucleic acid component is provided by a separate domain, wherein the probe comprises a further domain capable of providing a ligation template or primer, said domain comprising;

(a) a region of complementarity to a sequence within the probe, such that it forms part of a hairpin structure that comprises a cleavage recognition site; or (b) a region of double stranded nucleic acid that comprises a cleavage recognition site.

A region of double stranded nucleic acid that comprises a cleavage recognition site is provided by a nucleic acid strand that is hybridized to a region of the first strand of the probe, wherein the first strand may be viewed as the strand comprising the domain capable of providing a RCA template. Hence, as discussed above, the probe may comprise one or more cleavage oligonucleotides or restriction oligonucleotides.

As discussed above, it is a feature of the present invention to prevent the probe from using the first RCA product or intermediate molecule as an extension template, or to limit the extension. If the probe comprises an extendable 3' end that can participate in a target templated extension reaction, the extension product may displace probes bound to the target nucleic acid molecule as it is extended. If this occurred the feature of localisation of the second RCA product to the first RCA product would be lost.

It can be seen from the Figures and the exemplary embodiments described above that the probe of the invention may comprise a 3' end that hybridizes to its target nucleic acid molecule (first RCA product or intermediate molecule), e.g. wherein the probe comprises a target complementary binding domain at its 3' end. Similarly, cleavage of the probe may result in one or more parts of the probe comprising an extendable 3' end that is hybridized to the target nucleic acid molecule. In the circle RCA probe embodiments it will be apparent that, if the RCA template strand is dissociated from the primer strand, the primer strand may initiate a target templated extension reaction, e.g. the probe may be degraded up to the target complementary binding domain at the 5' end of the probe such that the domain comprises an extendable 3' end that can be extended by a polymerase using the target as a template for extension. Accordingly, one or more blocking groups may be included in the probe to prevent unwanted target templated extensions. Additionally or alternatively, it may be useful to utilise non-displaceable blocking oligonucleotides (displacement resistant oligonucleotides) in the methods of the invention. The non-displaceable oligonucleotides ("blocking oligonucleotides") may bind to regions of the target nucleic acid molecule in between probe binding domains in the target. Accordingly, any target templated extension product/reaction would be blocked by the non-displaceable blocking oligonucleotides before the extension product displaces a probe of the invention.

The probes of the invention may include blocking groups or "blocks" in one or more positions, which may be dependent on the design of the probe. For instance, a portion of the target complementary binding domain at the 5' end and/or 3' end of the probe may be modified to include a displacement block so that it cannot be displaced by a strand displacement polymerase, or by an extending strand. Thus, one or more of the binding domains of the probe may comprise an exonuclease and/or extension block and/or a displacement block.

The 3' end of the probe may be modified so that it cannot function as a primer. For instance, the probe may be designed so that the 3' end is not complementary to the target nucleic acid molecule and therefore cannot participate in a target templated extension reaction. Such a non-complementary end may include an exonuclease block.

In some embodiments, particularly with regard to the circle RCA probes of the invention, an exonuclease block may be included in the portion of the primer strand between the 5' target complementary binding domain and the RCA template complementary domain/primer domain.

Thus, various means and procedures may be used, singly or in combination, depending on the precise nature of the method steps and probe design employed. For example, modifications (e.g. blocking groups or modified residues) can be incorporated into the probe, which inhibit polymerase and/or exonuclease action (i.e. which inhibit extension and/or degradation), or which inhibit strand displacement. To prevent unwanted exonuclease digestion of any hybridised probes or probe components (i.e. after cleavage of the probes) from creating a primer capable of priming on the target nucleic acid molecule, the presence of any reagents having exonucleolytic activity can be avoided, for example an exonuclease-deficient polymerase can be used. In certain embodiments of the method of the invention washing steps may be used. For example, in the case of a probe which is designed to have one or more ligatable ends which hybridise to the target nucleic acid molecule in juxtaposition for ligation, any probes which have hybridised but not ligated may be removed by stringent washing (according to principles well known in the art). This is particularly applicable in the case of heterogeneous, or solid phase-based methods. Any combination of such means may be employed.

In the case of probes or probe components (i.e. following cleavage of the probe) having a 3'end which hybridises to the target nucleic acid molecule, where this 3' end is not required for ligation, a modification or block may be included at or near the 3' end which acts to inhibit extension (e.g. a "polymerase-block" or "extension block"). Alternatively or additionally a blocking oligonucleotide may be used, to prevent any extension which may occur from the 3' end from extending into and displacing any downstream probes. As noted above, such a blocking oligonucleotide will itself be modified to incorporate an extension and/or degradation block (e.g. at the 3'end) and a displacement block (e.g. at the 5' end).

In certain embodiments a probe may comprise a 3'end which hybridises to the target nucleic acid molecule and is required for ligation (e.g. to the 5' end of the probe). In such a situation it would not be appropriate to include an extension and/or degradation block at the hybridised 3'end, in order to ensure that the 3' end is available for ligation. In this case, unwanted 3' extension of any unligated 3' ends may be inhibited by stringent washing to remove any unligated probes. Alternatively or additionally, in such a case the probe may be modified at or near the hybridised ligatable 5' end to include a displacement block. In such a case any extension which does take place from the 3'end will not be to displace the hybridised 5'end.

The RCA reporter probes of the invention that are ligated using the target nucleic acid molecule as a ligation template (i.e. target templated ligation dependent probes) are particularly advantageous over RCA probes of the prior art, e.g. conventional padlock probes which are circularised directly on their target nucleic acids. In this respect, target templated ligation of a padlock probe acts to lock the circularised nucleic acid molecule to the ligation template (i.e. target nucleic acid molecule), which may inhibit RCA templated by the circularised molecule due to topological inhibition. It can be necessary to resolve or release the topological inhibition, e.g. by partial digestion of the target nucleic acid molecule, to allow the RCA reaction to proceed. However, as the probe of the present invention provides the nucleic acid components to enable RCA and the probe is itself extended to generate the RCA product, there is no need to resolve or unlock the probe from the target nucleic acid molecule to generate the RCA product. In fact, target nucleic acid molecule templated ligation of probe may help to facilitate the localisation of the second RCA product, i.e. to ensure the RCA product is linked to the first RCA product.

Thus the RCA reporter probes of the invention are particularly advantageous for use in methods for detecting a target analyte molecule by sRCA. In this respect, although multiple conventional padlock probes may bind to a target nucleic acid molecule that comprises multiple binding sites, the target molecule must be cleaved to allow a RCA reaction to proceed for each probe. Accordingly, the RCA products are not linked to each other, i.e. each RCA product is an extension of a separate part of the target nucleic acid molecule. Alternatively, if the target nucleic acid molecule is not cleaved, only a single padlock probe may generate a RCA product (i.e. a single extension of the 3' end of the target nucleic acid molecule). In contrast, the RCA reporter probes of the present invention do not require the target nucleic acid molecule (first RCA product or intermediate molecule) to be cleaved in order to generate the second RCA product. Thus, all of the second RCA products generated may be attached to the first RCA product. This allows all of the RCA products to be localized in the position of the first RCA product, which may result in a stronger signal and/or to allow a detectable signal to be generated faster.

In some embodiments it may be useful to design the RCA reporter probe such that the RCA components generated by cleavage of the probe will only remain bound to (i.e. attached to or hybridized to) the target nucleic acid molecule if the ends of the probe have been directly or indirectly ligated by virtue of a target templated ligation. This may be achieved, for example, by designing the probe to ensure that at least one of the target complementary domains (i.e. binding domains) may hybridize stably only in the presence of another target complementary domain, e.g. one of the target complementary binding domains may comprise a short region of complementarity to its target molecule. Prior to cleavage of the probe, the combination of the interaction of the target complementary domains (which are joined by the intervening sequence) with the target nucleic acid molecule is sufficient to attach the probe to its target nucleic acid. However, if the target complementary domains are not ligated (directly or indirectly), upon cleavage of the cleavable sites in the probe, at least one of the nucleic acid components of the probe required to enable RCA will dissociate from the target nucleic acid. Accordingly, the RCA reaction will not be able to proceed unless a target templated ligation has occurred.

It will be apparent that a target templated ligation may be intramolecular or intermolecular. Intramolecular ligation is described above, wherein the 5' and 3' ends of the probe hybridize to its target nucleic acid molecule such that the ends may be directly ligated (indirect ligation involves a gap oligonucleotide, as described below). Intermolecular ligation requires an additional nucleic acid molecule, e.g. a stabilization or ligation or "gap" oligonucleotide, which hybridizes to a region of the target nucleic acid molecule adjacent to the 5' or 3' end of a probe. The target complementary region of the probe may be ligated to the gap oligonucleotide using a ligase enzyme, which may prevent the RCA nucleic acid components provided by the probe from dissociating from the target nucleic acid molecule after cleavage of the probe.

As described above, in some embodiments the probe comprises multiple hairpin structures and the methods of using the probes of the invention may advantageously include a step of unfolding the domains of the probe to release the nucleic acid components that are necessary and sufficient to enable RCA. This may be achieved, for example, by altering the conditions of the sample to promote unfolding, e.g. altering the temperature or salt concentrations in the sample. Unfolding may involve displacing one or more strands of the nucleic acid construct, which may be an intramolecular or intermolecular displacement.

As generally discussed above, the methods of the invention allow a localised further RCA amplification of a first RCA, wherein a second or further RCA amplification product is localised to a first RCA amplification product. This can have a number of applications, most notably in signal amplification, and hence in any detection method or assay based on detecting an RCA product. Accordingly, in such an embodiment the methods of the invention as defined above may include an additional or further step of detecting a said attached second RCA product, thereby to detect said first RCA product, wherein detection is localised to the first RCA product.

Alternatively viewed, such an embodiment may be seen to provide a further aspect of the invention, which may be defined as a method for detection of a first product of an RCA reaction, said method comprising performing a localised RCA reaction as defined herein and detecting said second RCA product as defined above. In certain embodiments a localised detection (e.g. a spatial detection) may be allowed, for example where the first RCA product is immobilised or fixed in situ.

Advantages of such a method, as noted above, include stronger and/or faster signal amplification. The method thus has particular utility in the detection of any desired assay target or analyte, which may be a target/analyte nucleic acid molecule which may itself by amplified by RCA to form a first RCA product or a target/analyte nucleic acid molecule or any other molecule which may be detected by an assay which uses or generates a circular nucleic acid molecule as an assay reporter or a marker for the assay target/analyte (see above). Such a circle may be the first RCA template used to generate the first RCA product.

Thus the methods and probes of the invention may find utility in the detection of a nucleic acid molecule in a sample. The nucleic acid molecule may be the target analyte for detection or may be indicative of the presence of the target analyte in a sample. For instance, the nucleic acid molecule may be attached to the target, e.g. a nucleic acid domain of an antibody:nucleic acid conjugate which is bound, directly or indirectly, to the target, e.g. a protein molecule. Similarly, the nucleic acid molecule to be detected may be a nucleic acid molecule generated from the interaction between proximity probes, which are bound to the target analyte, e.g. a protein.

Accordingly, the invention may be seen to provide a method for detecting an analyte in a sample, wherein a first circular RCA template is used or generated (e.g. generated from a nucleic acid analyte or used or generated as a marker for said analyte), a first RCA reaction is performed using said first RCA template to generate a first RCA product, a localised second RCA reaction is performed as described herein to generate a second RCA product localised to said first RCA product, and said second RCA product is detected.

Thus a probe as defined or described herein may be used, particularly an RCA reporter probe, wherein said probe hybridises directly or indirectly to a first RCA product. The first RCA product may be generated by a first RCA reaction using a first RCA template which may itself be or be derived or generated from:
  (i) the analyte;
  (ii) a nucleic acid molecule (e.g. probe) directly or indirectly attached to the analyte; or
  (iii) indicative of, or a proxy for, (i.e. a marker for) the analyte in the sample.

As described above, by using an RCA reporter probe in the localised second RCA, the second RCA reaction can be controlled by requiring that at least one of the RCA components is released by a cleavage reaction and/or by unfolding the probe after the probe is contacted with first RCA product/intermediate molecule.

RCA templates, i.e. circular or circularisable nucleic acid molecules, e.g. oligonucleotides, are well known in the art. A RCA template typically may comprise about 20-1000 nucleotides, e.g. 26-1000, 30-1000, 30-900, 60-900, 40-800, 50-700, 60-600, 70-500, 80-400, 90-300 or 100-200 nucleotides, such as at least 20, 25, 26, 27, 28, 29, 30, 35, 40, 50, 60, 70, 80, 90, 100, 120, 150, 200 or 250 nucleotides.

Circularisable nucleic acid molecules (commonly known as padlock probes and variants thereof) typically are linear nucleic acid molecules that comprise free ends which may hybridise to one or more nucleic acid domains (common template(s)) which act to template the ligation of the free ends to each other to generate a circular oligonucleotide. Such a ligation may be direct, i.e. where the free ends hybridise to the ligation template directly adjacent to each other. Alternatively, the ligation may be indirect, i.e. where the free ends hybridise to the ligation template with a space in between which is filled by a "gap" oligonucleotide such that each free end is ligated to one end of the gap oligonucleotide. In some embodiments, the space in between the free ends may be "filled-in" by extending the free 3' end, e.g. in a polymerase reaction, using the ligation template as an extension template. Once the free 3' end has been extended to be adjacent to the free 5' end, the two ends may be joined by a ligation reaction.

In embodiments in which the second RCA template is provided as a preformed circle or circularisable strand of the probe (where the probe is a circle RCA probe) or is separately provided (not as part of the probe) and cleavage and/or unfolding of the probe is not required to generate the RCA template, the second RCA template is preferably provided as a preformed circle (a circular oligonucleotide). However, this is not an essential feature of the method or probe and the second RCA template could be provided as a circularisable oligonucleotide, wherein the domain of the probe to which the second RCA template is hybridised may function as the ligation template and/or extension template (based on the gap-fill embodiment described above).

In embodiments in which the second RCA template is released by cleavage and optionally unfolding of the domains of the probe (e.g. where the probe is a hairpin or linear RCA reporter probe), the second RCA template will be in the form of a circularisable nucleic acid molecule, i.e. one or more of the nucleic acid domains of the cleaved probe may release a 5' and/or 3' end, allowing the ligation of the ends to form a circular molecule (the second RCA template). Two or more second RCA template parts may be ligated together to form the second circular RCA template. The release of the ligatable 5' and 3' ends of the domain(s) can thus be viewed as the generation of a second RCA template for circularisation by ligation. In one preferred embodiment of the invention, ligatable 5' and 3' ends of a single RCA template domain hybridise to the ligation template directly adjacent to each other to obviate the need to provide a separate "gap" oligonucleotide (a gap oligonucleotide cannot be provided by the hairpin RCA probe of the invention). In other embodiments, the ligatable 5' and 3' ends of the domain may hybridise to the ligation template with a space in between, wherein the space is "filled in" by extension of the 3' end using the ligation template as an extension template, followed by ligation of the domain to form the RCA template.

The first and/or second RCA template may comprise a reporter domain, which is a sequence that can be used to detect and/or identify the RCA product, i.e. the primer extension product templated by the RCA template. This is particularly advantageous in multiplex embodiments of the invention, where more than one different first RCA product is subjected to the method e.g. where more than one analyte, e.g. nucleic acid analyte, is detected in a single assay. The second RCA template (e.g. a RCA template provided by each RCA reporter probe (e.g. each probe specific for a first RCA product derived from or indicative of a target analyte), may comprise a unique "marker" or identification sequence (e.g. a bar-code sequence, such as a site comprising the sequence of a specific detection probe, i.e. the RCA product is complementary to the RCA template and as such detection probes that hybridize to the RCA product will comprise a sequence that is identical to part of the RCA template) to allow the separate detection and/or quantification of each analyte in the sample. Thus, in multiplex assays each probe (or second RCA template) may comprise a different reporter domain and the detection of the interaction of the probe and the target analyte, i.e. the detection of each analyte, may be detected in parallel (i.e. at the same time), e.g. using oligonucleotides tagged with distinct fluorophores that may hybridise to the complement of the reporter domain. Alternatively, each marker (and therefore each analyte) may be detected using sequential visualisation reactions, wherein each reaction is separated by, e.g. stripping or bleaching steps. Methods of sequential visualisation reactions suitable for using the methods of the invention are known in the art, e.g. Göransson et al., 2009 (A single molecule array for digital targeted molecular analyses. Nucleic Acids Res. 2009 January; 37(1):e7), Wählby et al., 2002 (Sequential immunofluorescence staining and image analysis for detection of large numbers of antigens in individual cell nuclei. Cytometry, 47(1):32-41, 2002), which are hereby incorporated by reference. In some representative embodiments of the invention, multiple analytes may be detected in parallel. In other representative embodiments of the invention, multiple analytes may be detected sequentially.

Combinatorial methods of labelling, e.g. ratio labelling, using different combinations and/or ratios of different labels are known in the art and may be used to increase the number of different molecules, and hence different analytes which may detected at one time, or in the same reaction. For example, combinations using different coloured and/or fluorescent labels and/or different ratios of different coloured and/or fluorescent labels may be used. For example, such "colour"-coding with different combinations of coloured and/or fluorescent labels may be used in multiplex assays based on detection by flow cytometry or microscopy. Alternatively, using lanthanide isotope labels cyToF detection may be used. By way of example, 7 different fluorophores may be grouped into 4 different types. There are 7 different combinations if labelled with only one colour, with 2 colours there are 21 different combinations, for 3 and 4 colours there are 35 different combinations and so on.

A primer or primer domain (a RCA primer) is a part or region of the probe that comprises a 3' end that can be extended, e.g. in a polymerization reaction, using the second RCA template as the template for extension. Accordingly, the primer or primer domain comprises a region of complementarity (defined further below) to a part of the second RCA template, which forms a duplex that is sufficiently stable under the conditions of the assay to facilitate RCA template dependent extension of the primer. The primer domain may also function as a ligation template, as described herein and defined below. The primer domain of a probe will generally be at least 5 bp in length, typically at least 6, 8 or 10 bp in length, usually at least 15 bp in length and more usually at least 16 bp in length and may be as long as 30 bp in length or longer, where the length of the primer will generally range from 5 to 50 bp in length, e.g. from 6, 8 or 10 to 50 bp, usually from about 10 to 35 bp in length. In some embodiments, the primer or primer domain may comprise a cleavage recognition site (which may simply be a free 3' end susceptible to exonuclease digestion).

A ligation template or ligation template domain may be present in the probe, but is not essential in all embodiments, e.g. where the RCA template is provided as a preformed circle oligonucleotide. When present, the domain is a part or region of the probe to which the 5' and 3' ends of a circularisable RCA template may bind to template the direct or indirect ligation of the RCA template to form a circular oligonucleotide. As mentioned above, in some embodiments, the ligation template may also function as an extension template (for a "gap-fill" extension reaction). Accordingly, the ligation template or ligation template domain comprises a region of complementarity (defined further below) to parts (the 5' and 3' ends) of the RCA template (or parts thereof), which forms a duplex that is sufficiently stable under the conditions of the assay to facilitate ligation template dependent ligation of the circularisable RCA template. The ligation template domain of a probe will generally be at least 2 bp in length, typically at least 5 bp and usually at least 10 bp in length, such as at least 15, 16, 17, 18, 19 or 20 bp in length and may be as long as 30 bp in length or longer, where the length of the ligation template will generally range from 2 to 50 bp in length, usually from about 15 to 35 bp in length, or about 10-20 bp in length.

Thus in some embodiments the probe of the invention may be viewed as comprising various domains, which each function to interact with its target nucleic acid molecule (first RCA product or intermediate molecule) or provide at least one of the nucleic acid components for RCA by releasing a domain upon cleavage of a cleavage site and/or unfolding of the probe.

Thus, the probe comprises at least one domain comprising a region of complementarity to its target nucleic acid molecule, namely the first RCA product or intermediate molecule; a target complementary domain or binding domain. It will be understood from the discussion herein that such an intermediate molecule will comprise a region of complementarity to the first RCA product and a second region, which is not complementary to the first RCA product and comprises a region of complementarity to, or binding site for, a probe. One or more intermediate molecules may be used, for example an intermediate molecule may comprise binding sites for a multiplicity of probes, or an intermediate molecule may comprise one binding site for a probe, and one intermediate molecule for each probe may be used (for example where the intermediate molecule binds to a site present in each monomer). For simplicity, the invention is defined primarily with respect to direct interactions between the probe and a first RCA product, but where reference is made to this in the context of probe binding, or to unwanted extension using the first RCA product as template it will be understood that this will apply analogously to binding to or extension on the intermediate molecule. Moreover, in the context of detection assay methods, the first RCA product or intermediate molecule with which the probe interacts may be viewed as the target nucleic acid molecule for the probe, even though the objective of the method may be the detection of a nucleic acid molecule or other analyte with which the probe does not interact directly.

A region of complementarity to its target nucleic acid molecule refers to a portion of the probe that is capable of forming an intermolecular duplex with at least a region of the target nucleic acid molecule. In some embodiments the region of complementarity to the target nucleic acid molecule will be sufficient to form a stable duplex in the assay conditions in which the probe finds utility, such that the probe (or domains thereof) and target nucleic acid molecule will not dissociate even after cleavage and/or unfolding of the probe. In other embodiments the region of complementarity to the target nucleic acid molecule may be designed such that it is capable of forming a stable duplex with the target nucleic acid molecule only when at least one other target complementary domain of the probe forms a duplex with the target nucleic acid molecule (in the assay conditions in which the probe finds utility). Thus, it may be necessary to stabilise the duplex formed between the probe and the target nucleic acid molecule (e.g. by an intramolecular ligation of the domains of the probe that interact with the probe binding sites/domains on the target nucleic acid molecule) to prevent the probe (or domains thereof) and target nucleic acid molecule from dissociating after cleavage and/or unfolding of the probe.

In embodiments where the probe comprises a hairpin structure that must be unfolded and/or cleaved to release a RCA nucleic acid component (e.g. a hairpin RCA probe), the hairpin structure may comprise any suitable number of nucleotide residues such that the hairpin can be unfolded. In certain embodiments (particularly in relation to RCA reporter probe embodiments) the hairpin structure will unfold only under suitable conditions, e.g. on the addition of a cleavage agent. It will be apparent that the structure of the hairpin will depend on the method used to promote its unfolding. In a representative example the portion of the nucleic domain forming the hairpin structure i.e. the portion that provides the duplex and the loop of the hairpin structure, will be between from about 14 to about 1000 nucleotides in length, where in certain embodiments they may range from about 14 to about 500 nucleotides in length including from about 14 to about 250 nucleotides in length, e.g., from about 14 to about 160 nucleotides in length, such as from about 14 to about 150 nucleotides in length, from about 14 to about 130 nucleotides in length, from about 14 to about 110 nucleotides in length, from about 14 to about 90 nucleotides in length, from about 14 to about 80 nucleotides in length, from about 14 to about 75 nucleotides in length, from about 14 to about 70 nucleotides in length, from about 14 to about 60 nucleotides in length and any length between the stated ranges. Thus, the duplex part of the at least one hairpin structure (i.e. the stem of the stem loop structure) may be at least 3 base pairs in length, preferably at least 4, 5, 6, 7, 8, 9, 10, 11, 12, 13, 14, 15, 20, 25, 30, 40 or 50 base pairs in length. In other embodiments, the duplex part of the at least one hairpin structure of the probe may be at least 100, 200, 300 or 400 base pairs in length.

The single-stranded loop of the at least one hairpin structure preferably comprises at least 8 nucleotides, preferably at least 9, 10, 11, 12, 13, 14, 15, 20, 25, 30, 40 or 50 nucleotides. In other embodiments, the single-stranded loop of the at least one hairpin structure may be at least 100, 200, 300 or 400 nucleotides in length.

In certain preferred aspects of the invention the hairpin structure of the probes comprises at least one uracil residue, preferably at least 2, 3, 4, 5, 6, 7, 8, 9 or 10 uracil residues (which may provide a cleavage site)

"Complementary" nucleotide sequences will combine with specificity to form a stable duplex under appropriate hybridization conditions. For instance, two sequences are complementary when a section of a first sequence can bind to a section of a second sequence in an anti-parallel sense wherein the 3'-end of each sequence binds to the 5'-end of the other sequence and each A, T(U), G and C of one sequence is then aligned with a T(U), A, C and G, respectively, of the other sequence. RNA sequences can also include complementary G=U or U=G base pairs. Thus, two sequences need not have perfect homology to be "complementary" under the invention. Usually two sequences are sufficiently complementary when at least about 85% (preferably at least about 90%, and most preferably at least about 95%) of the nucleotides share base pair organization over a defined length of the molecule.

In some of the embodiments described above it may be useful for one domain of the probe to share complementarity with more than one other nucleic acid molecule. It may be particularly advantageous for the domain to have a different complementarity for each nucleic acid molecule with which it interacts, i.e. to allow one interaction to occur preferentially over a different interaction. For instance, in some embodiments the target complementary binding domain may be complementary to the target nucleic acid molecule and to a second or further strand of the probe e.g. a protective strand (in this context the protective strand may be seen as a "blocking" strand), wherein the interaction between the probe and the target nucleic acid molecule is sufficient to displace the "blocking" (protective) strand (i.e. unfold the probe). In another exemplary embodiment, the primer domain may be complementary to the "blocking" strand (here an invasion strand) and the RCA template, and the invasion strand may be complementary to the target nucleic acid molecule. The interaction between the probe and the target nucleic acid molecule is sufficient to displace the invasion strand from its interaction with the primer domain, wherein the invasion strand binds to the target nucleic acid molecule and the primer strand binds to the RCA template, i.e. the probe is unfolded to release the primer for RCA. Thus, the sequences of complementary domains of probe may share at least about 85%, e.g. 90, 91, 92, 93, 94, 95, 96, 97, 98, 99 or 100% sequence identity with one or more nucleic acid molecules, e.g. domains of the probe or target nucleic acid molecules.

The regions of complementarity (i.e. hybridisation regions) between any domains of the probe and/or the target nucleic acid molecule may have a length in the range of 4-100 bp. In some embodiments it may be useful to use relatively short regions of complementarity e.g. 6-20, 6-18, 7-15 or 8-12 bp. However, other longer regions of complementarity may be useful, particularly for interactions between the probe and the target nucleic acid molecule, e.g. at least 20, 25, 35, 40, 50, 60, 70, 80, 90 or 100 bp such as 10-100, 20-90, 30-70 or 40-60 bp.

In many embodiments of the invention the probe comprises at least one domain comprising a cleavage recognition site, e.g. a cleavage or cleavable domain. A cleavage recognition site is a sequence that is recognised by a cleavage enzyme, i.e. the cleavage enzyme is capable of interacting specifically with the cleavage recognition site, wherein said interaction results in the cleavage of a nucleic acid molecule. In some embodiments the cleavage enzyme may cleave the nucleic acid molecule at the cleavage recognition site, i.e. the cleavage recognition site may be a cleavage or cleavable domain. In other embodiments the cleavage enzyme may cleave at a position directly or indirectly adjacent to the cleavage recognition site, i.e. the cleavage or cleavable domain may form a domain that is distinct from the cleavage recognition site. Hence, the probe of the invention may comprise cleavage recognition sites and cleavable domains as separate features. In other embodiments, all of the cleavage recognition sites may be cleavable sites/domains.

In some embodiments, the probe comprises more than one cleavable domain, wherein cleavage of the cleavable domain releases a primer domain, RCA template and ligation template domain. In some embodiments, cleavage results in the unfolding of hairpin structures within the probe, which releases the RCA nucleic acid components. Thus, cleavage of a cleavable domain may result in the separation of the domains of the probe into distinct nucleic acid molecules (e.g. hairpin RCA probes), wherein the domains are held in proximity to each other by their interaction with the target nucleic acid molecule. If the probe is cleaved into separate nucleic acid domains that are not attached to the target nucleic acid molecule, the interaction between the domains (the regions of complementarity between the domains) is not sufficient to hold the domains in proximity to enable a RCA reaction (namely the second RCA reaction) to proceed.

"Cleavage" is defined broadly herein to include any means of breaking a nucleotide chain (i.e. a nucleotide sequence). Cleavage may thus involve breaking a covalent bond. This may involve cleavage of nucleotide chain (i.e. strand cleavage or strand scission), for example by cleavage of a phosphodiester bond.

In some embodiments, cleavage of the cleavage site of the probe concerns breaking at least one covalent bond linking adjacent nucleotide residues of the probe nucleic acid molecule, e.g. hydrolysis of the phosphodiester bond. Cleavage preferably involves the hydrolysis of one or more phosphodiester bonds, particularly wherein the cleavage site forms part of a hairpin structure. Thus, in some embodiments the cleavage recognition site (or cleavable domain) is in a hairpin structure.

In its simplest form, the cleavage recognition site may be a part of the probe that is available for cleavage (and/or susceptible to cleavage), preferably when the probe is bound to its target nucleic acid molecule. For instance, the cleavage recognition site may be a region at the end of the probe that is single stranded, e.g. a single stranded 3' end. In other words, in some embodiments the single stranded 3' end of a probe may be viewed as a cleavage domain. An exonuclease enzyme that is capable of degrading only single stranded nucleic acid may be used to degrade the single stranded end of the probe, wherein degradation will stop at a region of the probe that is double stranded and/or comprises a blocking domain, e.g. an exonuclease block. For instance, FIG. 1 depicts an embodiment in which degradation of the 3' end of the probe releases the primer domain for RCA template directed extension. In a preferred embodiment, the unfolding and/or cleavage of the circle RCA probe releases a single stranded 3' end that may be degraded by an exonuclease enzyme.

In particular embodiments, the probe comprises regions of double stranded nucleic acid, which may be in the form of hairpin structures, that may comprise an endonuclease recognition sequence, i.e. the cleavage recognition site may be an endonuclease recognition site. In an exemplary embodiment, e.g. where the probe comprises an endonuclease recognition site, the endonuclease will cleave only a single strand of the duplex portion of the probe, e.g. one strand of the hairpin structure, thereby releasing a RCA nucleic acid component or a domain that may provide a RCA nucleic acid component.

The probe may comprise an endonuclease recognition sequence. For example, a nucleic acid strand of the probe may be a "cleavage oligonucleotide" or a "restriction oligonucleotide", which hybridizes to another nucleic acid strand of the probe to provide an endonuclease recognition site. In some embodiments, a cleavage or restriction oligonucleotide may be hybridized to a single-stranded part or region of the probe, e.g. a single-stranded loop of a hairpin structure, to comprise a duplex within the probe. However, in embodiments where the cleavage oligonucleotide is provided separately it does not provide a RCA nucleic acid component, e.g. a ligation template.

In particular embodiments of the methods of the invention, e.g. using hairpin and/or linear RCA probes that comprise at least one cleavage strand, it may be advantageous to include, i.e. add, an excess of cleavage strands in the reaction mix. This may help to ensure that all of the probes that bind to a target nucleic acid molecule can release the nucleic acid components sufficient to initiate the second RCA reaction. For example, in some reaction conditions a proportion of cleavage strands may be dissociated from the probes. Thus, providing an excess of cleavage strands in the reaction mix, i.e. cleavage oligonucleotides, may be sufficient to replace any cleavage strands that have been displaced from the probe, i.e. to reassemble the probe in situ.

In some embodiments, the endonuclease may be a restriction endonuclease (a restriction enzyme), i.e. the cleavage recognition site may be a restriction endonuclease recognition site. It will be understood that this will apply to embodiments in which the cleavage site is not created by target binding i.e. does not comprise a target nucleic acid molecule. Any suitable restriction endonuclease may be used to cleave the probe, i.e. the probe may comprise an suitable restriction endonuclease recognition site. As described above, in particular embodiments it may be useful to utilise a type II restriction endonuclease recognition sequence, and optionally a cleavage domain. Some type II restriction endonucleases, e.g. type IIS enzymes, may find particular utility in the methods of the invention. Type II restriction endonucleases either cleave within a specific cleavage recognition site or at an adjacent site (a cleavage domain), wherein the adjacent site may be a specific distance from the cleavage recognition site (e.g. a type IIS enzyme) and/or may comprise an additional cleavage recognition site (e.g. a type IIE enzyme).

In some embodiments the cleavage recognition site is achieved by providing a probe, e.g. a hairpin structure in the probe, that comprises one or more Uracil residues. The domain comprising the uracil residues, e.g. a hairpin structure, can be cleaved by treatment with a uracil-DNA glycosylase (UNG) enzyme in combination with an endonuclease enzyme capable of recognising apurinic/apyrimidinic (AP) sites of dsDNA, e.g. endonuclease IV, wherein cleavage releases one or more RCA nucleic acid components. Accordingly, the cleavage recognition site, e.g. the cleavable domain, may comprise one or more uracil residue, e.g. 2, 3, 4, 5, 6, 7, 8, 9, 10 or more uracil residues.

In some embodiments the cleavable domain, e.g. hairpin structure, may be cleaved, and thereby release one or more RCA nucleic acid components, using a nickase enzyme, which cleaves only one strand in the duplex of the cleavable domain, e.g. hairpin structure. Thus, the cleavage recognition site may be a site for a nickase enzyme. Nickases are endonucleases which cleave only a single strand of a DNA duplex. As described above, a cleavage recognition site may be provided in a single-stranded region of the probe, e.g. a loop of a hairpin structure, e.g. by annealing (hybridising) an oligonucleotide to said single-stranded region, e.g. loop, or when a target complementary domain comprising a cleavage recognition site binds to the target nucleic acid molecule. Alternatively viewed, the cleavage recognition site may become functional, i.e. may be in a form that is recognised and cleaved by a endonuclease (or enables the endonuclease to cleave the probe at a position adjacent to the cleavage recognition site, i.e. in a cleavable domain), when a cleavage oligonucleotide or target nucleic acid molecule interacts with the cleavage recognition site. In other embodiments, a blocking oligonucleotide may bind to the cleavage recognition site to prevent cleavage from occurring.

Some nickases introduce single-stranded nicks only at particular sites on a DNA molecule, by binding to and recognizing a particular nucleotide recognition sequence, i.e. a cleavage recognition sequence. Some nickases introduce single-stranded nicks at mis-match positions in a duplex. Hence, in some embodiments, the cleavage recognition site may be formed when the target complementary domain binds to the target nucleic acid molecule with a mis-match, i.e. the target complementary domain may not be 100% complementary to the target binding region in the target nucleic acid molecule, as defined above. A number of naturally-occurring nickases have been discovered, of which at present the sequence recognition properties have been determined for at least four. Nickases are described in U.S. Pat. No. 6,867,028, which is herein incorporated by reference in its entirety and any suitable nickase recognition site may be used in the probes and methods of the invention.

In some preferred embodiments of the methods of the invention that utilise a nickase enzyme, the nickase enzyme is removed from the assay or inactivated following cleavage, and optionally unfolding, of the probe to prevent unwanted cleavage of ligation products.

In further embodiments of the invention an exonuclease enzyme may be used to degrade a portion of one strand of the probe, e.g. a single-stranded domain at the 3' end of the probe or a hairpin structure, thereby releasing a RCA nucleic acid component provided by the probe. Hence, the cleavage recognition site, or more particularly the cleavage domain, may be a single stranded part of the probe or a hairpin structure that is susceptible to exonuclease cleavage, i.e. unblocked. The exonuclease enzyme may have 5' or 3' exonuclease activity depending on the orientation of the hairpin structure or the design of the probe. In some embodiments, the exonuclease activity may be provided by a polymerase enzyme.

In some embodiments, one or more of the RCA nucleic acid components may be released by unfolding the probe and this may be achieved in a number of ways. In particular embodiments, one RCA nucleic acid components may be unfolded by cleavage, i.e. one or more RCA nucleic acid components may be released by cleavage and unfolding of the probe. In some embodiments, only cleavage of the probe is required to release one or more RCA nucleic acid components, wherein said cleavage may comprise cleaving one or more cleavage domains, e.g. 2, 3, 4, 5 or more cleavage domains. In some embodiments, e.g. the hairpin RCA probes, cleavage occurs in a hairpin structure of the nucleic acid domain (i.e. the cleavage domain is located in, or forms part of, a hairpin structure). As discussed above, cleavage is preferably enzymatic cleavage.

As described above, some of the probes of the invention comprise at least one hairpin structure. A hairpin structure may also be known as a hairpin-loop or a stem-loop and these terms are used interchangeably herein. A hairpin is an intramolecular base-pairing pattern that can occur in a single-stranded DNA or RNA molecule. A hairpin occurs when two regions of the same strand, usually complementary in nucleotide sequence when read in opposite directions, base-pair to form a double helix (a duplex) that ends in an unpaired, i.e. single-stranded, loop.

In some aspects of the invention, a hairpin structure does not form the end of the probe, i.e. the duplex of at least one hairpin is flanked by a single-stranded region at the 5' and/or 3' ends of duplex. Thus, in some embodiments, a hairpin may be at one end of the probe, i.e. one end of the duplex (the 3' or 5' end) forms the end of the probe.

Unfolding of the probe may also be achieved by disrupting at least part of the double stranded element (portion or domain) of the probe, such as a hairpin structure, e.g. the hairpin structure in a circle RCA probe. This may be achieved by altering the conditions of the sample such that the hairpin structure is no longer a thermodynamically favourable structure, e.g. by altering the temperature or salt concentrations of the solution. In some embodiments, unfolding is achieved by contacting the probe with the target nucleic acid molecule, i.e. target dependent unfolding, wherein the interaction (the duplex formed) between the probe and the target is more stable than the intramolecular duplex formed by the domains of the probe, i.e. unfolding may include displacing a nucleic acid strand. Similarly, the hairpin structure may be destabilised by modification of one or more of the nucleotide bases in the duplex to disrupt the hydrogen bonds (so-called Watson-Crick base pairing) which anneal the two strands. For example, cleavage of the base from the nucleotide may be sufficient to disrupt the duplex enough to "unfold" the hairpin.

Thus cleavage and/or unfolding the probe results in the release of at least one of the nucleic acid components for an RCA reaction, particularly at least the primer. As described above, prior to cleavage and/or unfolding of the probe at least one of the RCA nucleic acid components, i.e. the primer and/or circular or circularisable RCA template, is unable to participate in, or initiate, the second RCA reaction. For instance, prior to unfolding and/or cleavage, at least one of the RCA nucleic acid components is inaccessible (e.g. unavailable or blocked) for a rolling circle amplification reaction, i.e. not in a form that will allow RCA. For example, the primer domain may not have a free 3' extendable end, e.g. the probe may comprise additional nucleotides downstream of, 3' to, the 3' end of the primer domain that do not have complementarity to the RCA template. Or the primer domain may be hybridised in the stem structure of a hairpin. Additionally or alternatively, the RCA template may not be circularised. Hence, release of one or more RCA nucleic acid components means that the probe is unfolded and/or cleaved to make said one or more components available, i.e. accessible, for a RCA reaction. In other words, the probe gives rise to, generates or allows to be generated one or more RCA nucleic acid components. Thus, release may involve unblocking said one or more components so that they are available to initiate, or participate in, a RCA reaction. Release may be converting or modifying said probe to generate or produce one or more components that will enable a RCA reaction to commence, i.e. in the presence of a suitable polymerase enzyme.

The domains of the probe may be made up of ribonucleotides and/or deoxyribonucleotides as well as synthetic nucleotide residues that are capable of participating in Watson-Crick type or analogous base pair interactions. Thus, the nucleic acid domains may be DNA and/or RNA or any modification thereof e.g. PNA or other derivatives containing non-nucleotide backbones. In some embodiments, the probe domain may comprise an exonuclease block, such that it cannot be used as a primer in a target templated nucleic acid extension reaction, i.e. cannot be recognised as a primer by a polymerase enzyme and/or cannot be degraded to produce a nucleic acid molecule capable of priming extension of the target nucleic acid molecule.

The possible lengths of the domains of the probe are defined above and it will be apparent that when the probe comprises multiple nucleic acid strands, each strand may be of a different length, which may vary widely. For instance, a protective strand and/or cleavage strand typically may comprise between 4-100 nucleotides, e.g. 5-90, 6-80, 7-70, 8-60, 9-50, 10-40 nucleotides, such as at least 12, 15, 18, 20, 25, 30 or 35 nucleotides, whereas a RCA template typically may comprise 20-1000 nucleotides, e.g. 26-1000, 30-900, 40-800, 50-700, 60-600, 70-500, 80-400, 90-300, 100-200 nucleotides, such as at least 20, 25, 26, 27, 28, 29, 30, 35, 40, 45, 50, 60, 70, 80, 90, 100, 120, 150, 200 or 250 nucleotides. Typically, the length of the primer strand of a circle RCA probe is similar to the range of lengths that are typical for an RCA template. The length of a hairpin RCA probe (i.e. the strand that provides the RCA template) typically may comprise 40-1500 nucleotides, e.g. 50-1400, 60-1300, 70-1200, 80-1100, 90-1000 nucleotides, such as at least 40, 45, 50, 55, 60, 65, 70, 75, 80, 85, 90, 95, 100, 125, 150, 175, 200, 250 or 300 nucleotides. Where the RCA probe comprises more than one nucleic acid strand, the length of the probe may be defined according to the longest strand, e.g. the primer strand, circle strand, RCA template strand.

As mentioned above, to allow probe binding the target nucleic acid molecule is at least partially single stranded and generally will be fully single stranded. To allow binding of probes or intermediate molecules, the first RCA product will, as mentioned above, generally have low secondary structure, and conditions favouring hybridisation may be employed. In embodiments where the probe comprises more than one target complementary domain, the target nucleic acid molecule may be viewed as comprising a probe binding site for each complementary binding domain. Alternatively, each target complementary binding domain may be viewed as binding to a different portion (region or part) of the probe binding domain. In preferred embodiments, the target complementary binding domain(s) of the probe and the probe binding site(s) of its target share at least 85% sequence identity, preferably 90%, e.g. 95, 96, 97, 98, 99 or 100%. In some embodiments, it may be useful to have at least one mis-match in the duplex to create a functional cleavage recognition site (a cleavable domain), e.g. which may be cleaved by a nickase enzyme. The length of the probe binding site may be the same as the length of the target complementary binding domain of the probe, as defined above, or may be longer, e.g. if multiple target complementary binding domains bind to the probe binding site.

As described above, the methods and probes of the invention may be useful for the detection of any target analyte, wherein if the target analyte is not a nucleic acid molecule, a first RCA template (or indeed a first RCA product) may be viewed as a marker for the analyte.

The "analyte", or ultimate detection assay target or objective, may be any substance (e.g. molecule) or entity it is desired to detect. The analyte is thus the "target" of a detection method or use of the invention. The analyte may accordingly be any biomolecule or chemical compound it may be desired to detect, for example a peptide or protein, or nucleic acid molecule or a small molecule, including organic and inorganic molecules. The analyte may be a cell or a microorganism, including a virus, or a fragment or product thereof. An analyte can be any substance or entity for which a specific binding partner (e.g. an affinity binding partner) can be developed. Such a specific binding partner may be a nucleic acid probe (for an nucleic acid analyte) and may lead directly to the generation of a first RCA template (e.g. a padlock probe). Alternatively, as discussed above, the specific binding partner may be coupled to a nucleic acid, which may be detected using an RCA strategy, e.g. in an assay which uses or generates a circular nucleic acid molecule which can be the first RCA template. Analytes of particular interest may thus include nucleic acid molecules, such as DNA (e.g. genomic DNA, mitochondrial DNA, plastid DNA, viral DNA etc) and RNA (e.g. mRNA, microRNA, rRNA, snRNA, viral RNA etc), and synthetic and/or modified nucleic acid molecules, (e.g. including nucleic acid domains comprising or consisting of synthetic or modified nucleotides such as LNA, PNA, morpholino etc), proteinaceous molecules such as peptides, polypeptides, proteins or prions or any molecule which includes a protein or polypeptide component, etc., or fragments thereof. The analyte may be a single molecule or a complex that contains two or more molecular subunits, e.g. including but not limited to protein-DNA complexes, which may or may not be covalently bound to one another, and which may be the same or different. Thus in addition to cells or microrganisms, such a complex analyte may also be a protein complex or protein interaction. Such a complex or interaction may thus be a homo- or hetero-multimer. Aggregates of molecules, e.g. proteins may also be target analytes, for example aggregates of the same protein or different proteins. The analyte may also be a complex between proteins or peptides and nucleic acid molecules such as DNA or RNA, e.g. interactions between proteins and nucleic acids, e.g. regulatory factors, such as transcription factors, and DNA or RNA. Advantageously, where the analyte is a nucleic acid molecule, the nucleic acid may be detected in situ, i.e. without removing or extracting the nucleic acid from the cell. However, isolated and amplified nucleic acid molecules also represent appropriate target analytes.

All biological and clinical samples are included, e.g. any cell or tissue sample of an organism, or any body fluid or preparation derived therefrom, as well as samples such as cell cultures, cell preparations, cell lysates etc. Environmental samples, e.g. soil and water samples or food samples are also included. The samples may be freshly prepared or they may be prior-treated in any convenient way e.g. for storage.

Representative samples thus include any material which may contain a biomolecule, or any other desired or target analyte, including for example foods and allied products, clinical and environmental samples. The sample may be a biological sample, which may contain any viral or cellular material, including all prokaryotic or eukaryotic cells, viruses, bacteriophages, mycoplasmas, protoplasts and organelles. Such biological material may thus comprise all types of mammalian and non-mammalian animal cells, plant cells, algae including blue-green algae, fungi, bacteria, protozoa etc. Representative samples thus include whole blood and blood-derived products such as plasma, serum and buffy coat, blood cells, urine, faeces, cerebrospinal fluid or any other body fluids (e.g. respiratory secretions, saliva, milk, etc), tissues, biopsies, cell cultures, cell suspensions, conditioned media or other samples of cell culture constituents, etc. The sample may be pre-treated in any convenient or desired way to prepare for use in the methods and uses of the invention, for example by cell lysis or purification, isolation of the analyte, etc.

The detection of the target analyte depends upon the presence of an analyte in a sample, which leads to the generation of the first RCA product. A second RCA product is then generated according to the invention, and can be detected in order to detect the analyte. As discussed above, the second RCA product can lead to a much stronger and/or faster signal. In some embodiments it can be advantageous to detect both the first and second RCA products, e.g. using separate labelled detection probes for each. Thus detecting the second product, which has a stronger signal can allow detection at low magnification for example. A more precise localisation at higher magnification can further be obtained by detecting the first product.

Thus, upon the addition of an appropriate polymerase (and if necessary other enzymes, e.g. cleavage and/or ligase enzymes), the presence of analyte in the sample may be detected by rolling circle amplification (RCA) of the second RCA template, i.e. by detecting the second RCA product, and optionally the first RCA product. The concatemeric RCA products provide the "signal" for detection of the analyte. Said signal may be detected by any appropriate means known in the art (see below for further examples) and as taught in U.S. Pat. No. 7,320,860, e.g. by hybridisation of labelled probes to a reporter domain sequence, which is repeated throughout the concatemeric RCA products.

As mentioned above, in certain embodiments at least one of the RCA nucleic acid components of the probes must be released by cleavage and/or unfolding to enable a RCA product to be generated. Accordingly, in representative embodiments, reagents that are required to detect the RCA products e.g. amplify the RCA product, may be added to the reaction at the same time as the probe, thereby avoiding the need for the addition of specific detection reagents in a separate step. Minimising the number of steps in the assay may facilitate the reduction in the overall time needed to carry out the assay, i.e. increase the efficiency of the assay, and contribute to the enhanced signal to noise ratio, i.e. help to reduce non-specific background.

In some embodiments, the second RCA template (and indeed the first RCA template) may be circularised by a ligation reaction, i.e. on addition of an appropriate ligase. In certain RCA reporter probe embodiments all of the nucleic acid components for the RCA are provided by the RCA reporter probe. However, ligation of the RCA template may encompass the use of a gap oligonucleotide. Hence, in embodiments that utilise a circle RCA probe, the probe may comprise a gap oligonucleotide or gap strand. A gap strand may be defined as an oligonucleotide that hybridizes to the primer strand of the RCA probe in between the 5' and 3' end of the circularisable RCA template. Each end of the RCA template is ligated to an end of the gap oligonucleotide to generate the circularised RCA template. It will be evident that a gap oligonucleotide may be provided separately to the probes of the invention, i.e. in some embodiments a gap oligonucleotide is not part of the probe. Hence, in the methods of the invention, a gap oligonucleotide may be added to the sample before, after, or contemporaneously with the probe. In some embodiments, several different gap oligonucleotides may be added, wherein each type of gap oligonucleotide is added at a different concentration. Each type of gap oligonucleotide may comprise common sequences at the 5' and 3' ends that are complementary to the ligation template domain (in between the ends of the circularisable RCA template) and a different intervening sequence, which may act as a reporter domain as defined above. The resultant RCA products will comprise different reporter domain sequences depending on which gap oligonucleotide was ligated into the RCA template and can be detected separately. This may be utilised to extend the dynamic range of the assay methods described herein, as described in WO2012/049316.

The term "detecting" is used broadly herein to include any means of determining the presence of the analyte (i.e. if it is present or not) or any form of measurement of the analyte. Thus "detecting" may include determining, measuring, assessing or assaying the presence or absence or amount or location of analyte in any way. Quantitative and qualitative determinations, measurements or assessments are included, including semi-quantitative. Such determinations, measurements or assessments may be relative, for example when two or more different analytes in a sample are being detected, or absolute. As such, the term "quantifying" when used in the context of quantifying a target analyte(s) in a sample can refer to absolute or to relative quantification. Absolute quantification may be accomplished by inclusion of known concentration(s) of one or more control analytes and/or referencing the detected level of the target analyte with known control analytes (e.g. through generation of a standard curve). Alternatively, relative quantification can be accomplished by comparison of detected levels or amounts between two or more different target analytes to provide a relative quantification of each of the two or more different analytes, i.e., relative to each other.

The sequences of the various domains of the probes (i.e. primer domain, ligation template domain, RCA template, binding domains etc and the intervening (i.e. connecting) sequences) may be chosen or selected with respect to the sequence of each domain in the probe and its target nucleic acid molecule. Thus, the sequence of the various domains is not critical as long as the domains that are required to interact to enable the production of a second RCA product can hybridise to each other under the appropriate conditions, e.g. in the presence of the target nucleic acid molecule (first RCA product or intermediate molecule). However, with the exception of the sequences required for the hairpin structures of the probes, the sequences of the domains should be chosen to avoid the occurrence of intramolecular hybridization (i.e. hybridization events between domains of the same strand). For example, the primer domain should not be capable of hybridising to the ligation template domain. Once the sequence of the domains is selected or identified, the probe may be synthesized using any convenient method.

The term "hybridisation" or "hybridises" as used herein refers to the formation of a duplex between nucleotide sequences which are sufficiently complementary to form duplexes via Watson-Crick base pairing. Two nucleotide sequences are "complementary" to one another when those molecules share base pair organization homology. Hence, a region of complementarity in a domain of a probe refers to a portion of that domain that is capable of forming an intra- or intermolecular duplex, i.e. either a duplex within the same molecule (a hairpin structure) or a duplex with a different molecule or a different strand of the probe construct. These terms are also used to refer to base pair interactions which are analogous to Watson-Crick base pairing, including Hoogsteen base pairing which is a rarely observed variation of base pairing which also allows for a third strand to wind around a double-helix assembled in a Watson-Crick pattern to form a triplex.

The amount of probe that is added to a sample may be selected to provide a sufficiently low concentration of probe in the reaction mixture to minimise non-target specific interactions, i.e. to ensure that the probe will not randomly bind to non-target molecules in the sample to any great or substantial degree. For example, in certain embodiments it is intended that only when the probe binds its target nucleic acid molecule (i.e. only in the presence of the first RCA product) are the RCA primer, and optionally other RCA nucleic acid components released and allowed to generate a second RCA product. In representative embodiments, the concentration of each probe in the reaction mixture following combination with the sample containing the first RCA product ranges from about 1 fM to 1 μM, such as from about 1 pM to about 1 nM, including from about 1 pM to about 100 nM, e.g. 1, 2, 5, 10, 20, 50 nM.

A number of different probes may be added to a sample for a multiplex assay (for example in a situation where multiple different first RCA products or first RCA templates have been generated or added, in order to detect multiple analytes in parallel. Multiplex assays may involve the detection of tens, hundreds, thousands or even tens of thousands of analytes in a sample. Accordingly, multiplex assays may comprise at least 2 distinct probes, i.e. probes capable of hybridising (directly or indirectly) to different first RCA products and hence, for example, detecting different analytes. For instance, multiplex assays may utilise at least 3, 4, 5, 10, 20, 30, 40 or 50 probes, such as 100, 200, 500, 1000, 10000 or more probes.

Following combination of the sample (or reaction mixture) containing the first RCA product and the probe(s), the reaction mixture may be incubated for a period of time sufficient for the probe(s) to bind to its target (first RCA product, or intermediate molecule), if present, in the sample. As described above, in certain embodiments once the probe has bound (directly or indirectly) to the first RCA product, the probe may be unfolded and/or cleaved to release at least the RCA primer and optionally other RCA nucleic acid components, and if necessary the domains of the probe may be allowed to interact, i.e. for the primer to interact with the second RCA template so as to form a primer/RCA template complex for the second RCA. In other embodiments, a primer and second RCA template may simply be added. Once a primer/RCA template complex has formed, the primer may be extended using the second RCA template as a template for polymerisation. Where more than one type of probe is used in the assay, each different type of RCA probe may be cleaved and/or unfolded separately, e.g. the first probe may be unfolded by cleavage and the second probe may be unfolded by target binding. In some representative embodiments, e.g. in situ assays or other assays in which the first RCA product is immobilised, wash steps may be included between the addition of probe and the detection of the RCA product, e.g. the first RCA product may be captured or immobilised on a solid support or substrate, which may be washed to remove unbound or non-specifically bound probe or RCA products that are not attached to the first RCA product. In some embodiments, wash steps may be included between cleaving the probe and the detection of second RCA product, e.g. to remove cleaved domains of the probe that are not directly or indirectly to the first RCA product. Alternatively, or additionally, a washing step may be included after the probe has been added to the sample and allowed to bind, but before the unfolding and/or cleavage step.

In representative embodiments, the probe and sample may be pre-incubated for a period of time ranging from 5 minutes to about 24 hours prior to the addition of the additional probes. Preferably said pre-incubation is from about 20 minutes to 12 hours at a temperature ranging from 4 to about 50° C. e.g. 10-40° C. or 20-37° C. Conditions under which the reaction mixture is maintained should be optimized to promote specific binding of the probe to its target nucleic acid molecule, while suppressing unspecific interaction.

Following pre-incubation, if such a step is included, the probe may be cleaved and/or unfolded and the resulting mixture may be incubated for a period of time ranging from about 5 minutes to about 48 hours, including from about 30 minutes to about 12 hours, at a temperature ranging from about 4 to about 105° C., including from about 4 to about 80° C., such as about 10 to about 70° C., about 15 to about 60° C., typically about 20 to about 37° C. Incubation at high temperatures, e.g. above about 40-50° C., may utilise thermophilic or hyperthermophilic enzymes, e.g. ligases and/or polymerases. Conditions should allow for efficient and specific hybridization between the RCA nucleic acid components, as described above.

Following the combination of the sample with the probe, the gap oligonucleotide(s) may be added, if used, and allowed to hybridise. Alternatively or additionally, one or more gap oligonucleotides may be added with the probe. In some embodiments, the gap oligonucleotides may be pre-hybridized to the probe.

In general, any convenient protocol that is capable of detecting the presence of an RCA product may be employed to detect the second RCA product, and optionally the first RCA product. The detection protocol may or may not require a separation step.

In some embodiments, a ligation template domain stabilises the ends of a circularisable second RCA template, which are ligated by contacting the reaction mixture with a nucleic acid ligating activity, e.g. provided by a suitable nucleic acid ligase, and maintaining the mixture under conditions sufficient for ligation of the nucleic acid domains to occur. In other embodiments the 3' and 5' ends of the probe may be ligated together upon hybridisation to the first RCA product. In still other embodiments, the probe may be ligated to a second probe, when both are hybridised to the first RCA product.

As is known in the art, in template-directed ligation ligases catalyze the formation of a phosphodiester bond between juxtaposed 3'-hydroxyl and 5'-phosphate termini of two immediately adjacent nucleic acids when they are annealed or hybridized to a third nucleic acid sequence to which they are complementary (i.e. a ligation template). Any convenient ligase may be employed, where representative ligases of interest include, but are not limited to: Temperature sensitive and thermostable ligases. Temperature sensitive ligases include, but are not limited to, bacteriophage T4 DNA ligase, bacteriophage T7 ligase, and E. coli ligase. Thermostable ligases include, but are not limited to, Taq ligase, Tth ligase, Ampligase® and Pfu ligase. Thermostable ligase may be obtained from thermophilic or hyperthermophilic organisms, including but not limited to, prokaryotic, eukaryotic, or archael organisms. Certain RNA ligases may also be employed in the methods of the invention.

A suitable ligase and any reagents that are necessary and/or desirable may be combined with the reaction mixture and maintained under conditions sufficient for ligation of the hybridized oligonucleotides to occur, e.g. ligation of the second RCA template via the probe ligation template, ligation of one or more of the target complementary binding domains templated by the target nucleic acid molecule (first RCA product or intermediate molecule). Ligation reaction conditions are well known to those of skill in the art. During ligation, the reaction mixture in certain embodiments may be maintained at a temperature ranging from about 4° C. to about 105° C., about 4 to about 80° C., such as about 10 to about 70° C., about 15 to about 60° C., typically such as from about 20° C. to about 37° C. for a period of time ranging from about 5 seconds to about 16 hours, such as from about 1 minute to about 1 hour. In yet other embodiments, the reaction mixture may be maintained at a temperature ranging from about 35° C. to about 45° C., such as from about 37° C. to about 42° C., e.g., at or about 38° C., 39° C., 40° C. or 41° C., for a period of time ranging from about 5 seconds to about 16 hours, such as from about 1 minute to about 1 hour, including from about 2 minutes to about 8 hours. In a representative embodiment, the ligation reaction mixture includes 50 mM Tris pH7.5, 10 mM $MgCl_2$, 10 mM DTT, 1 mM ATP, 25 mg/ml BSA, 0.25 units/ml RNase inhibitor, and T4 DNA ligase at 0.125 units/ml. In yet another representative embodiment, 2.125 mM magnesium ion, 0.2 units/ml RNase inhibitor; and 0.125 units/ml DNA ligase are employed.

It will be evident that the ligation conditions may depend on the ligase enzyme used in the methods of the invention. Hence, the above-described ligation conditions are merely a representative example and the parameters may be varied according to well known protocols. For example, a ligase that may be utilized in the methods of the invention, namely Ampligase®, may be used at temperatures of greater than 50° C. However, it will be further understood that the alteration of one parameter, e.g. temperature, may require the modification of other conditions to ensure that other steps of the assay are not inhibited or disrupted, e.g. binding of the probe to the target nucleic acid molecule. Such manipulation of RCA assay methods is routine in the art.

Following ligation (if ligation is required, e.g. if the probe comprises or provides a circularisable second RCA template or the probe must be ligated to stabilize its interaction with its target nucleic acid molecule) the second RCA template (which may be the ligation product) may be detected, for example as an indication of the presence, or as a measure of the amount and optionally the location, of an analyte in the sample.

The next step of the method following a ligation step (if required) is to generate the second RCA product, i.e. to extend the RCA primer using the second RCA template in a polymerisation reaction. Rolling-circle amplification (RCA) is well known in the art, being described in Dean et al., 2001 (Rapid Amplification of Plasmid and Phage DNA Using Phi29 DNA Polymerase and Multiply-Primed Rolling Circle Amplification, *Genome Research*, 11, pp. 1095-1099), the disclosures of which are herein incorporated by reference. In representative second RCA reactions, the circular or circularised second RCA template is able to interact with the RCA primer, which is provided by the probe. The RCA primer is employed in a primer extension reaction, e.g. the RCA primer is extended on the second RCA template to generate the second RCA product, being a single concatemeric product. The RCA primer will be of sufficient length, as described above, to provide for hybridization to the RCA template under annealing conditions (described in greater detail below).

In addition to the above nucleic acid components, the reaction mixture produced in the subject methods typically includes a polymerase, e.g. phi29 DNA polymerase and other components required for a DNA polymerase reaction as described below. The desired polymerase activity may be provided by one or more distinct polymerase enzymes. In some embodiment the polymerase has exonuclease activity, e.g. 5' and/or 3' exonuclease activity.

In preparing the reaction mixture of this step of the subject methods, the various constituent components may be combined in any convenient order. For example, all of the various constituent components may be combined at the same time to produce the reaction mixture.

The amplified products of the RCA reaction (namely the second RCA reaction, but also optionally the first RCA product) may be detected using any convenient protocol, where the particular protocol employed may detect the RCA products non-specifically or specifically, as described in greater detail below. For instance, the RCA product may be detected directly, e.g. the concatemer may be cleaved to generate monomer which may be detect using gel electrophoresis, or more preferably by hybridizing labelled detection oligonucleotides that hybridize to the reporter domain in the RCA product. Alternatively, the RCA product may be detected indirectly, e.g. the product may be amplified by PCR and the amplification products may be detected.

Representative non-specific detection protocols of interest include protocols that employ signal producing systems that selectively detect single or double stranded DNA products, e.g., via intercalation. Representative detectable molecules that find use in such embodiments include fluorescent nucleic acid stains, such as phenanthridinium dyes, including monomers or homo- or heterodimers thereof, that give an enhanced fluorescence when complexed with nucleic acids. Examples of phenanthridinium dyes include ethidium homodimer, ethidium bromide, propidium iodide, and other alkyl-substituted phenanthridinium dyes. In another embodiment of the invention, the nucleic acid stain is or incorporates an acridine dye, or a homo- or heterodimer thereof, such as acridine orange, acridine homodimer, ethidium-acridine heterodimer, or 9-amino-6-chloro-2-methoxyacridine. In yet another embodiment of the invention, the nucleic acid stain is an indole or imidazole dye, such as Hoechst 33258, Hoechst 33342, Hoechst 34580 (BIOPROBES 34, Molecular Probes, Inc. Eugene, Oreg., (May 2000)) DAPI (4',6-diamidino-2-phenylindole) or DIPI (4',6-(diimidazolin-2-yl)-2-phenylindole). Other permitted nucleic acid stains include, but are not limited to, 7-aminoactinomycin D, hydroxystilbamidine, LDS 751, selected psoralens (furocoumarins), styryl dyes, metal complexes such as ruthenium complexes, and transition metal complexes (incorporating $Tb^{3+}$ and $Eu^{3+}$, for example). In certain embodiments of the invention, the nucleic acid stain is a cyanine dye or a homo- or heterodimer of a cyanine dye that gives an enhanced fluorescence when associated with nucleic acids. Any of the dyes described in U.S. Pat. No. 4,883,867 to Lee (1989), U.S. Pat. No. 5,582,977 to Yue et al. (1996), U.S. Pat. No. 5,321,130 to Yue et al. (1994), and U.S. Pat. No. 5,410,030 to Yue et al. (1995) (all four patents incorporated by reference) may be used, including nucleic acid stains commercially available under the trademarks TOTO, BOBO, POPO, YOYO, TO-PRO, BO-PRO, PO-PRO and YO-PRO from Molecular Probes, Inc., Eugene, Oreg. Any of the dyes described in U.S. Pat. No. 5,436,134 to Haugland et al. (1995), U.S. Pat. No. 5,658,751 to Yue et al. (1997), and U.S. Pat. No. 5,863,753 to Haugland et al. (1999) (all three patents incorporated by reference) may be used, including nucleic acid stains commercially available under the trademarks SYBR Green, EvaGreen, SYTO, SYTOX, PICOGREEN, OLIGREEN, and RIBOGREEN from Molecular Probes, Inc., Eugene, Oreg. In yet other embodiments of the invention, the nucleic acid stain is a monomeric, homodimeric or heterodimeric cyanine dye that incorporates an aza- or polyazabenzazolium heterocycle, such as an azabenzoxazole, azabenzimidazole, or azabenzothiazole, that gives an enhanced fluorescence when associated with nucleic acids, including nucleic acid stains commercially available under the trademarks SYTO, SYTOX, JOJO, JO-PRO, LOLO, LO-PRO from Molecular Probes, Inc., Eugene, Oreg.

In yet other embodiments, a signal producing system that is specific for the RCA product, as opposed to nucleic acid molecules in general, may be employed to detect the amplification. In these embodiments, the signal producing system may include a probe nucleic acid or oligonucleotide that specifically binds to a sequence found in the RCA product (i.e. a reporter domain sequence), where the probe nucleic acid/oligonucleotide may be labelled with a directly or indirectly detectable label. A directly detectable label is one that can be directly detected without the use of additional reagents, while an indirectly detectable label is one that is detectable by employing one or more additional reagents, e.g., where the label is a member of a signal producing system made up of two or more components. In many embodiments, the label is a directly detectable label, where directly detectable labels of interest include, but are not limited to: fluorescent labels, radioisotopic labels, chemiluminescent labels, and the like. In many embodiments, the label is a fluorescent label, where the labelling reagent employed in such embodiments is a fluorescently tagged nucleotide(s), e.g. fluorescently tagged CTP (such as Cy3-CTP, Cy5-CTP) etc. Fluorescent moieties which may be used to tag nucleotides for producing labelled probe nucleic acids (i.e. detection probes) include, but are not limited to: fluorescein, the cyanine dyes, such as Cy3, Cy5, Alexa 555, Bodipy 630/650, and the like. Other labels, such as those described above, may also be employed as are known in the art.

In certain embodiments, the specifically labelled probe nucleic acids (detection probes) are labelled with "energy transfer" labels. As used herein, "energy transfer" refers to the process by which the fluorescence emission of a fluorescent group is altered by a fluorescence-modifying group. Energy transfer labels are well known in the art, and such labelled oligonucleotide probes include the TaqMan® type probes, as described in U.S. Pat. No. 6,248,526, the disclosure of which is herein incorporated by reference (as well as Held et al., Genome Res. (1996) 6:986-994; Holland et al., Proc. Natl Acad. Sci. USA (1991) 88:7276-7280; and Lee et al., Nuc. Acids Res. (1993) 21:3761-3766). Further examples of detection probes include: Scorpion probes (as described in Whitcombe et al., Nature Biotechnology (1999) 17:804-807; U.S. Pat. No. 6,326,145, the disclosure of which is herein incorporated by reference), Sunrise probes (as described in Nazarenko et al., Nuc. Acids Res. (1997) 25:2516-2521; U.S. Pat. No. 6,117,635, the disclosure of which is herein incorporated by reference), Molecular Beacons (Tyagi et al., Nature Biotechnology (1996) 14:303-308; U.S. Pat. No. 5,989,823, the disclosure of which is incorporated herein by reference), and conformationally assisted probes (as described in provisional application Ser. No. 60/138,376, the disclosure of which is herein incorporated by reference).

Thus, determining the presence of the second, and optionally first, RCA product may be achieved using any convenient protocol. The reaction mixture may be screened etc. (i.e., assayed, assessed, evaluated, tested, etc.) for the presence of any resultant second, and optionally first, RCA products in order to detect the presence of the target analyte in the sample being assayed. The particular detection protocol may vary depending on the sensitivity desired and the application in which the method is being practiced.

The RCA product may be detected in a number of different ways. For example, the nucleotides incorporated in the RCA product may be directly labelled, e.g., fluorescently, or otherwise spectrophotometrically, or radioisotopically labelled or with any signal-giving label, such that the RCA product is directly labelled. In some embodiments detection probes as discussed above, e.g., fluorescently labelled probes, molecular beacons (as described above) etc. may be employed to detect to the presence of the RCA product, where these probes are directed to a sequence (reporter domain sequence, i.e. a sequence that is identical to the reporter domain sequence in the RCA template) that is repeated in the RCA concatemer and therefore only exists in its entirety in the RCA product.

The reaction mixture prepared in this detection step of the subject methods may further include an aqueous buffer medium that includes a source of monovalent ions, a source of divalent cations and a buffering agent. Any convenient source of monovalent ions, such as KCl, K-acetate, $NH_4$-acetate, K-glutamate, $NH_4Cl$, ammonium sulphate, and the like may be employed. The divalent cation may be magnesium, manganese, zinc and the like, where the cation will typically be magnesium. Any convenient source of magnesium cation may be employed, including $MgCl_2$, Mg-acetate, and the like. The amount of $Mg^{2+}$ present in the buffer may range from 0.5 to 10 mM, although higher or lower amounts may be used and may depend on the type of reaction. For instance, for PCR the amount of $Mg^{2+}$ present in the buffer may be about 1.5 mM, whereas for RCA, the amount of $Mg^{2+}$ present in the buffer may about 10 mM. Representative buffering agents or salts that may be present in the buffer include Tris, Tricine, HEPES, MOPS and the like, where the amount of buffering agent will typically range from about 5 to 150 mM, usually from about 10 to 100 mM, and more usually from about 20 to 50 mM, where in certain preferred embodiments the buffering agent will be present in an amount sufficient to provide a pH ranging from about 6.0 to 9.5, where most preferred is pH 7.3 at 72° C. Other agents which may be present in the buffer medium include chelating agents, such as EDTA, EGTA and the like.

The next step in the subject methods is signal detection from the labelled RCA products of interest, where signal detection may vary depending on the particular signal producing system employed. In certain embodiments, merely the presence or absence of detectable signal, e.g., fluorescence, is determined and used in the subject assays, e.g., to determine or identify the presence or absence of the second (and optionally first) RCA product (and hence the target analyte). Depending on the particular label employed, detection of a signal may indicate the presence or absence of the second (or first) RCA product.

In those embodiments where the signal producing system is a fluorescent signal producing system, signal detection typically includes detecting a change in a fluorescent signal from the reaction mixture to obtain an assay result. In other words, any modulation in the fluorescent signal generated by the reaction mixture is assessed. The change may be an increase or decrease in fluorescence, depending on the nature of the label employed, but in certain embodiments is an increase in fluorescence. The sample may be screened for an increase in fluorescence using any convenient means, e.g., a suitable fluorimeter, such as a thermostable-cuvette or plate-reader fluorimeter, or, for example where the sample is a tissue sample on a microscope slide, fluorescence may be detected using a fluorescence microscope. Fluorescence is suitably monitored using a known fluorimeter. The signals from these devices, for instance in the form of photomultiplier voltages, are sent to a data processor board and converted into a spectrum associated with each sample tube. Multiple tubes, for example 96 tubes, can be assessed at the same time. Thus, in some embodiments multiple analytes may be detected in parallel, whereas in other embodiments multiple analytes may be detected sequentially, e.g. one analyte at a time or one group of analytes at a time.

Where the detection protocol is a real time protocol, e.g., as employed in real time PCR reaction protocols, data may be collected in this way at frequent intervals, for example once every 3 minutes, throughout the reaction. By monitoring the fluorescence of the reactive molecule from the sample during each cycle, the progress of the amplification reaction can be monitored in various ways. For example, the data provided by melting peaks can be analyzed, for example by calculating the area under the melting peaks and these data plotted against the number of cycles.

The spectra generated in this way can be resolved, for example, using "fits" of pre-selected fluorescent moieties such as dyes, to form peaks representative of each signalling moiety (i.e. fluorophore). The areas under the peaks can be determined which represents the intensity value for each signal, and if required, expressed as quotients of each other. The differential of signal intensities and/or ratios will allow changes in labelled probes to be recorded through the reaction or at different reaction conditions, such as temperatures. The changes are related to the binding phenomenon between the oligonucleotide probe and the target sequence or degradation of the oligonucleotide probe bound to the target sequence. The integral of the area under the differential peaks will allow intensity values for the label effects to be calculated.

Screening the mixture for a change in fluorescence provides one or more assay results, depending on whether the sample is screened once at the end of the primer extension reaction, or multiple times, e.g., after each cycle, of an amplification reaction (e.g., as is done in real time PCR monitoring).

The data generated as described above can be interpreted in various ways. In its simplest form, an increase or decrease in fluorescence from the sample in the course of or at the end of the amplification reaction is indicative of an increase in the amount of the target analyte present in the sample, e.g. as correlated to the amount of RCA product detected in the reaction mixture, suggestive of the fact that the amplification reaction has proceeded and therefore the target analyte was in fact present in the initial sample. Quantification is also possible by monitoring the amplification reaction throughout the amplification process. Quantification may also include assaying for one or more nucleic acid controls in the reaction mixture, as described above.

In this manner, a reaction mixture may readily be screened (or assessed or assayed etc.) for the presence of RCA product, and hence of target analyte(s), e.g. nucleic acid analytes. The methods are suitable for detection of a single target analyte as well as multiplex analyses, in which two or more different target analytes are assayed in the sample. In these latter multiplex situations, the number of different sets of probes that may be employed typically ranges from about 2 to about 20 or higher, e.g., as up to 100 or higher, 1000 or higher, etc. wherein the multiple analytes in a sample may be detected in parallel or sequentially.

The analysis of many analytes simultaneously and in a single reaction using several different probes (multiplexing) may enhanced by the increased sensitivity, and in certain embodiments also increased specificity, which may be obtained using the methods and probes of the invention. Each probe set can be designed to produce a RCA product that can be used to determine the presence or absence, quantity and/or location of the analytes ultimately being interrogated by the probe. The RCA product may be detected using any of the well established methods for analysis of nucleic acid molecules known from the literature including liquid chromatography, electrophoresis, mass spectrometry, microscopy, real-time PCR, fluorescent probes, microarray, colorimetric analysis such as ELISA, flow cytometry, mass spectrometry (CyTOF) etc.

The probes and methods of the present invention may be employed homogeneously (i.e. in solution) as described above, or alternatively heterogeneously, using a solid phase, for example, in which the first RCA product becomes immobilised on a solid phase, permitting the use of washing steps. This may result from immobilisation of the target analyte, for example in in situ detection procedures. The use of solid phase assays offers advantages, particularly for the detection of difficult samples: washing steps can assist in the removal of unbound and/or unligated probes etc, inhibiting components, and analytes can be enriched from an undesirably large sample volume. Higher concentrations and greater amounts of probes can be used, as unbound analytes, probes and RCA products can be removed by washing.

Immobilisation of the first RCA product and/or analyte on a solid phase may be achieved in various ways. Accordingly, several embodiments of solid phase assays are contemplated. In one such embodiment, the analyte can first be captured by an immobilised (or immobilisable) capture probes, the first RCA product can generated such that it is attached to the analyte, for example by virtue of the primer for the first RCA product being attached to the analyte, e.g. by being coupled to a binding partner for the analyte, and the first RCA product may then be bound by subsequently added probe(s) comprising or providing the primer for the second RCA. Alternatively, the first RCA product may simply be immobilised to a solid support. For example the primer for the first RCA product may be provided with an immobilisable group or moiety or means for immobilisation, or may be immobilised, prior to the first RCA.

The immobilised capture probe or first RCA primer, or first RCA product, may be immobilised, i.e. bound to the support, in any convenient way. Thus the manner or means of immobilisation and the solid support may be selected, according to choice, from any number of immobilisation means and solid supports as are widely known in the art and described in the literature. Thus, the capture probe, or first RCA primer or first RCA product may be directly bound to the support (e.g. chemically crosslinked), it may be bound indirectly by means of a linker group, or by an intermediary binding group(s) (e.g. by means of a biotin-streptavidin interaction). Thus, a capture probe or first RCA primer or first RCA product may be provided with means for immobilisation (e.g. an affinity binding partner, e.g. biotin or a hapten or a nucleic acid molecule, capable of binding to its binding partner, i.e. a cognate binding partner, e.g. streptavidin or an antibody or a nucleic acid molecule) provided on the support. A capture probe may be immobilised before or after binding to the analyte. Further, such an "immobilisable" capture probe may be contacted with the sample together with the support. Analogously, a first RCA primer may be immobilised before or after the first RCA etc.

The capture probe may be, for example, an antibody or nucleic acid molecule that is capable of binding to the target analyte specifically. In other words the capture probe may be an immobilised (or immobilisable) analyte-specific probe comprising an analyte binding domain (i.e. an analyte capture probe). Thus in such an embodiment the analyte is first captured by the immobilised or immobilisable capture probe which serves only to immobilise the analyte on the solid phase, and subsequently the immobilised analyte is subjected to a detection protocol which uses, or leads to the generation of, a first RCA template, wherein the primer for the first RCA is attached to the analyte. In such an embodiment, the capture probe may be any binding partner capable of binding the analyte, directly or indirectly. More particularly, such a capture probe binds specifically to the analyte.

The solid support may be any of the well known supports or matrices which are currently widely used or proposed for immobilisation, separation etc. These may take the form of particles (e.g. beads which may be magnetic or non-magnetic), sheets, gels, filters, membranes, fibres, capillaries, or microtitre strips, tubes, plates or wells etc.

The support may be made of glass, silica, latex or a polymeric material. Suitable are materials presenting a high surface area for binding of the analyte. Such supports may have an irregular surface and may be for example porous or particulate e.g. particles, fibres, webs, sinters or sieves. Particulate materials e.g. beads are useful due to their greater binding capacity, particularly polymeric beads.

Conveniently, a particulate solid support used according to the invention will comprise spherical beads. The size of the beads is not critical, but they may for example be of the order of diameter of at least 1 and preferably at least 2 μm, and have a maximum diameter of preferably not more than 10, and e.g. not more than 6 μm.

Monodisperse particles, that is those which are substantially uniform in size (e.g. size having a diameter standard deviation of less than 5%) have the advantage that they provide very uniform reproducibility of reaction. Representative monodisperse polymer particles may be produced by the technique described in U.S. Pat. No. 4,336,173.

However, to aid manipulation and separation, magnetic beads are advantageous. The term "magnetic" as used herein means that the support is capable of having a magnetic moment imparted to it when placed in a magnetic field, i.e. paramagnetic, and thus is displaceable under the action of that field. In other words, a support comprising magnetic particles may readily be removed by magnetic aggregation, which provides a quick, simple and efficient way of separating the particles following the analyte binding steps.

In a further embodiment, the analyte itself may be immobilised (or immobilisable) on the solid phase e.g. by non-specific absorption. In a particular such embodiment, the analyte may be present within cells, being optionally fixed and/or permeabilised, which are (capable of being) attached to a solid support, e.g. a tissue sample comprising analyte may be immobilised on a microscope slide.

The above-described methods typically result in detection of target dependent first RCA products (i.e. first RCA products that are only produced in the presence of the target analyte) that are present in the reaction mixture. This leads to the generation of second RCA products which in turn provides a measure of the amount of target analyte in the sample being assayed. The measure may be qualitative or quantitative.

Accordingly, the above described probes and methods for detecting the presence of one or more target analytes in a complex sample find use in a variety of different applications.

The subject probes and methods may be used to screen a sample for the presence or absence of one or more target analytes in a sample. As indicated above, the invention provides probes and methods for detecting the presence or quantifying the amount of one or more target analytes in a sample.

The subject probes and methods can be employed to detect the presence of one or more target analytes in a variety of different types of samples, including complex samples having large amounts of non-target entities. The subject methods are highly sensitive for detecting one or more target analytes in a simple or complex sample.

It will be evident from the description above and the representative examples described below that the methods and probes of the invention have advantages over existing methods. Notably, the methods allow for signal amplification of the signal from the first RCA product, thereby increasing the sensitivity of the method, and, as also noted above, faster signal generation. Increased sensitivity may permit analytes to be detected which are present only in low amounts. Essentially, the method permits an enhanced signal to be developed from an RCA reaction. A larger, more conspicuous reaction product is formed, which may more readily and easily be detected. The amplified signal from the second RCA product is localised to the first RCA product. This may permit highly sensitive localised detection of an analyte, for example in situ detection.

Thus in a method according to the present invention, a first RCA product may be generated in a highly specific manner, that is production of the first RCA product, or indeed first RCA template, may be strictly dependent upon the presence of an analyte (e.g. in the case of a padlock probe, or an assay using proximity probes which must both bind and interact to generate a circular RCA template). It is advantageous for the second RCA to be dependent upon the presence of the first RCA product (as discussed above), but the requirement for specificity in this second RCA step is less strict (indeed it can be much less strict) and some background generation of second RCA product can be tolerated, as in the absence of first RCA product this will be far less than in its presence (both in terms of signal strength and size). In the presence of first RCA product, i.e. when a sRCA reaction takes place, a very strong signal amplification takes place. This is demonstrated in the Examples below.

Whilst not wishing to be bound by theory, it is believed that two or more generations of RCA product, when attached together, and labelled (e.g. with detection probes, for example for the second RCA product) will travel together as a single particle in a fluid. This may open up the possibility to use other detection modalities to detect the second RCA product (or the sRCA product of the method), for example flow cytometry or CyTOF, thereby broadening up the instrument base available for detection in RCA-based assays.

The strong signal amplification afforded by the second RCA reaction may allow ready and easy visualisation of signals, for example microscopically at low magnification or on a digitally scanned image and hence may permit rapid and easy visual inspection of assay results in a clinical scenario, e.g. inspection of pathology results in routine use. Thus the methods of the invention are particularly suited to clinical analysis procedures.

As noted above both first and second RCA products can be detected, allowing the second products to be easily detected e.g. at low magnification, whilst preserving the more precise location of the first RCA products using detection probes specific for the first RCA products.

This can for instance be helpful to identify rare integrated copies of viral genomes in human tissues or for otherwise detecting rare RCA products such as upon inefficient mutation detection in tissues. Another example when easy identification of a rare event may be helpful is when screening for the presence of circulating tumour cells (CTC) among a vast majority of non-CTC cells. The strong signal of the sRCA reaction allows fast and easy identification of events (detection of CTCs) at low magnification and the more precise localisation of the first RCA product visualised at higher magnification allows verification that the signal originated in a CTC and not in adjacent non-CTC cell.

The faster signal amplification which may be achieved by initiating the second RCA whilst the first is ongoing is also discussed above. Thus the methods allow RCA-dependent detection assays to be speeded up, which may be of value in at point of care locations such as doctor's offices etc. Further increases of speed and/or signal strength are possible by carrying out further RCA rounds or generations in the sRCA method.

The increases in signal strength/speed may allow other means of detection beyond the conventional fluorescence based methods, for example using turbidometric, magnetic, particle counting, electric, surface sensing, and weight-based detection techniques. For example one individual sRCA product from a second generation RCA after a 1 hour amplification has the potential weight of several femtograms. Such a weight increase may be detected by methods and means known in the art such as cantilevers, surface plasmon methods, and microbalances e.g. quartz crystal microbalances etc.

Since the method of present invention generates an enhanced signal which is localised to the product of the first RCA, it also confers the ability to count individual reaction products (second RCA products), triggered by individual nucleic acid circles (first RCA templates), using standard flow cytometers or distributed on a planar surface, etc. for highly precise digital detection. Thus, the method may permit an equivalent reaction to digital PCR, but with no need for emulsions or microfabricated structures, or finding conditions where exactly one template is present per compartment.

The prominent amplification products derived from the method of the present invention will further permit cloning of individual DNA circles, since the product obtained from an individual circle (e.g. first RCA template) may be visualised. An individual sRCA product may therefore be identified and isolated. For example, with the aid of the amplification method of the present invention visualization can be achieved in low melt agarose for isolation with no need for magnification, and the product may then be isolated e.g. scoped out with a toothpick, analogously to the isolation of bacterial colonies.

The sRCA methods of the present invention offer the potential to identify and count even very rare mutations, including when relatively error-prone mutation detection methods are used. Thus a first RCA product may be generated using a mutation-containing analyte target nucleic acid circle as first RCA template and the repeated occurrence of a mutant sequence in the first RCA product may be detected, by using an allele-specific (e.g. mutation-specific) probe for the second RCA i.e. a probe which recognises the mutant sequence present in the monomer repeats of the first RCA product.

The detection of rare mutations can be very important clinically for diagnosis. For example mutations in certain genes (e.g. KRAS mutations) can be diagnostically important and may serve to identify the emergence of acquired resistance to particular therapies (e.g. anti-EGFR therapy). Much effort has focused in recent years on developing methods for detecting such mutations. The method of the present invention could provide a useful addition to such methods.

An example of a method to detect rare mutations utilising the sRCA reaction of the present invention may involve isolating DNA from target cells, fragmenting the DNA, isolating a fragment which may contain a target sequence (e.g. mutation) of interest using a "selector" probe which is designed to have two target-specific ends which bind specifically to a target region of interest and allow the target fragment to be circularised, and performing a first RCA reaction using the circularised target fragment as first RCA template. The first RCA product thus generated may be subjected to the sRCA method of the present invention. Advantageously, an RCA reporter probe may be used to generate the second RCA product, particularly a target-templated ligation dependent RCA reporter probe, whose ligation is templated by the first RCA product. The probe for the second RCA can be designed to recognise (e.g. bind to, and/or be ligated by) a mutant sequence it is desired to detect. Thus, by isolating target sequences to generate a first RCA template, the opportunity is afforded to generate a first RCA product comprising multiple (complementary) copies of the target sequence. Thus, an increased number of "targets" can be created in the concatemeric first RCA product. Each of these may be bound by a probe, which may be designed to be specific for the mutation it is desired to detect, to initiate a second RCA reaction, and the second RCA product can be detected to detect the mutation.

The invention will be further described with reference to the following non-limiting Examples with reference to the following drawings in which:

FIG. 1 depicts a solid phase sRCA reaction according to the invention, as exemplified in Example 1. A second generation RCA product is sequentially developed as follows: a first RCA product is generated from an first RCA template circle using an immobilised primer. A probe comprising a primer for a second RCA is allowed to hybridise to the first RCA product, together with a second circular RCA template, which may be pre-hybridised to the probe. A second RCA reaction is then initiated, primed by the hybridised primer, to generate a second RCA product which is hybridised to the first RCA product.

FIG. 2 depicts a homogenous sRCA reaction according to the invention, in which a second RCA product is simultaneously developed as follows: a probe comprising a primer for the second RCA reaction and a second RCA circular template are contacted with a first RCA product generated from a first RCA template. The probe is in the form of a hairpin, the duplex of which comprises a binding domain for the first RCA product and a primer domain comprising a domain of complementarity to the second RCA template. Upon binding of the probe to the first RCA product the hairpin is opened and the RCA template binds to the primer domain, allowing a second RCA reaction to be initiated.

FIG. 3 depicts a solid phase sRCA reaction in which a second RCA product is sequentially developed using two separately provided probes which hybridise to the first RCA product and template the ligation of two added oligonucleotides to form a circular second RCA template. One of the probes comprises a primer domain which is able to prime the second RCA reaction once the second RCA template has been formed by ligation. Ligation of the two probes stabilises their hybridisation to the first RCA product, and hence the attachment of the first RCA product.

FIG. 4 shows a circle RCA probe, wherein binding of the probe to the target nucleic acid molecule forms a cleavage recognition site (A), which is cleaved (B) to release the primer for extension (C).

FIG. 5 shows a two-part hairpin RCA probe bound to a nucleic acid molecule (e.g. first RCA product). A and A', and B and B', represent complementary sequences, wherein the domain comprising A and B functions as the ligation template for circularisation of the RCA template by hybridizing to A' and B' after cleavage of the probe. C represents a cleavage domain.

FIG. 6 shows three variants of two-part hairpin RCA probes. Probes 1 and 2 require a target templated ligation to allow the RCA components to be maintained in proximity after their release by cleavage. Probe 3 may be involved in a target templated ligation, but this is not essential. A and A', and B and B', represent complementary sequences, wherein the domain comprising A and B functions as the ligation template for circularisation of the RCA template by hybridizing to A' and B' after cleavage of the probe. C represents a cleavage domain.

Figure 9:
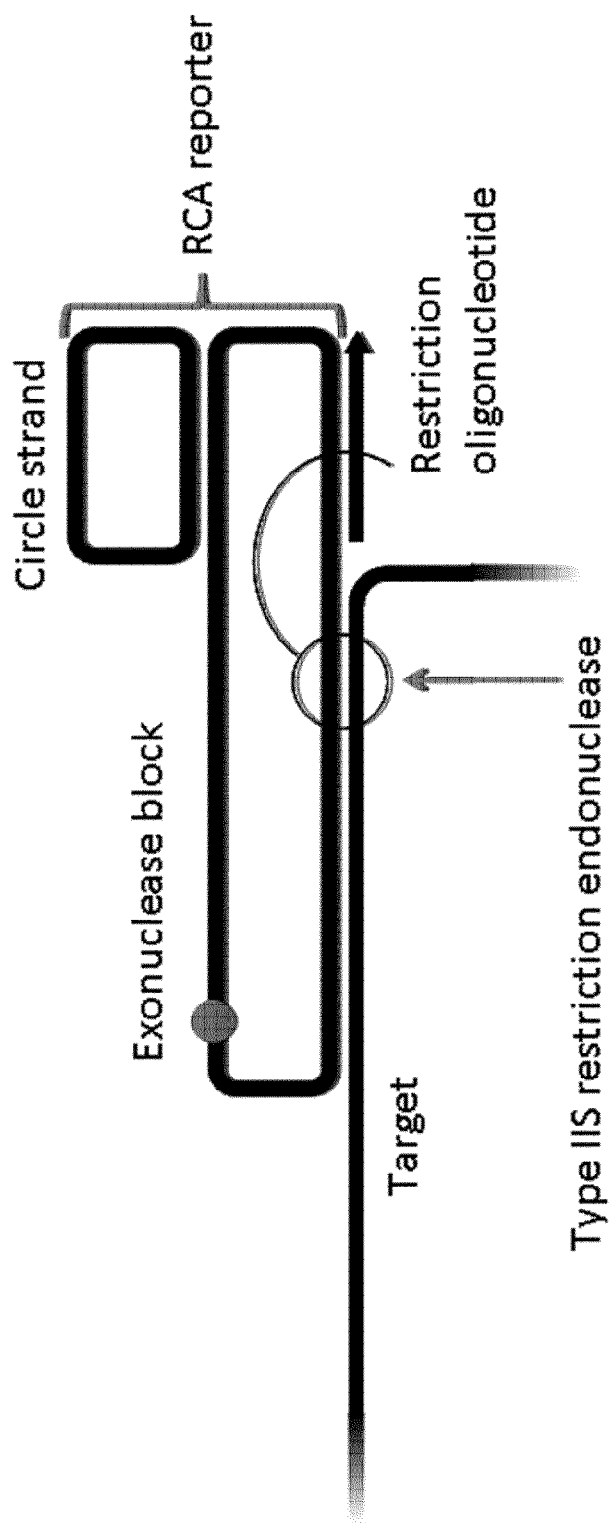

FIG. 9 shows a circle RCA probe comprising a cleavage strand. A cleavage recognition site is formed when the probe binds to the target nucleic acid molecule, which allows the cleavage domain formed by the cleavage strand to be cleaved. Cleavage releases the RCA primer.

Figure 10:
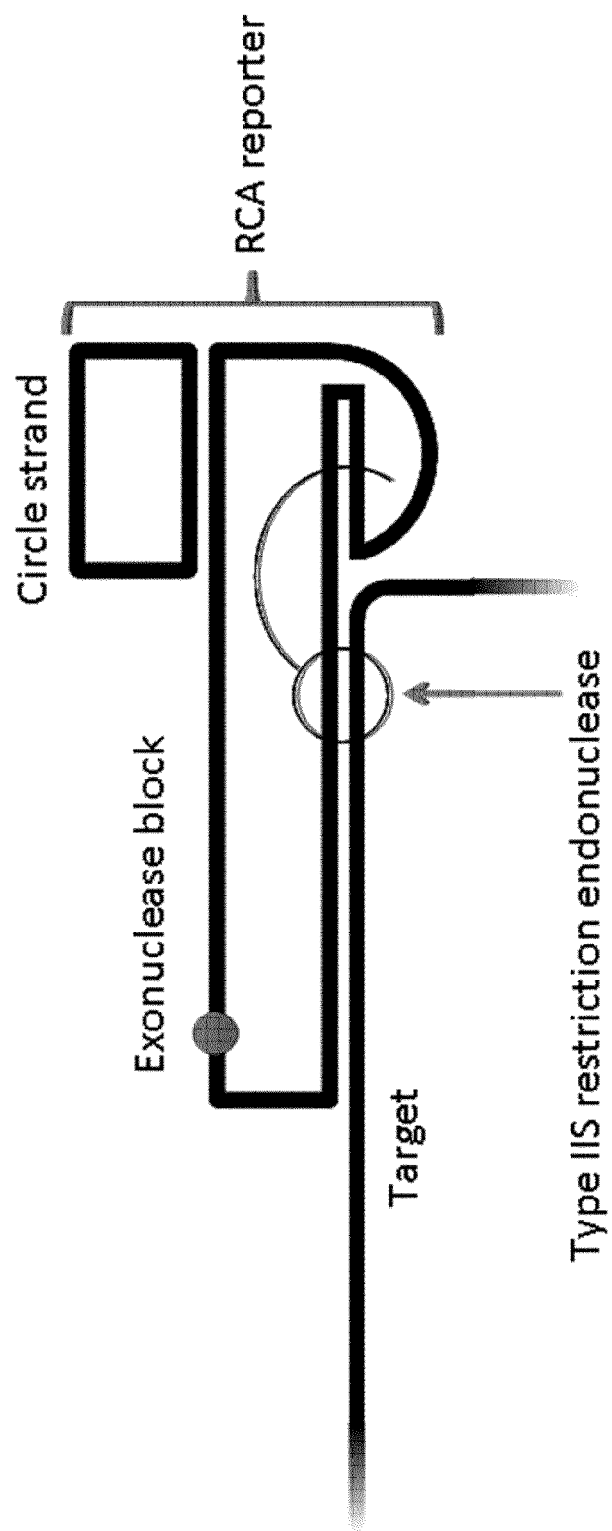

FIG. 10 shows a circle RCA probe as described in FIG. 9, wherein the cleavage domain is formed by a hairpin structure.

Figure 11:
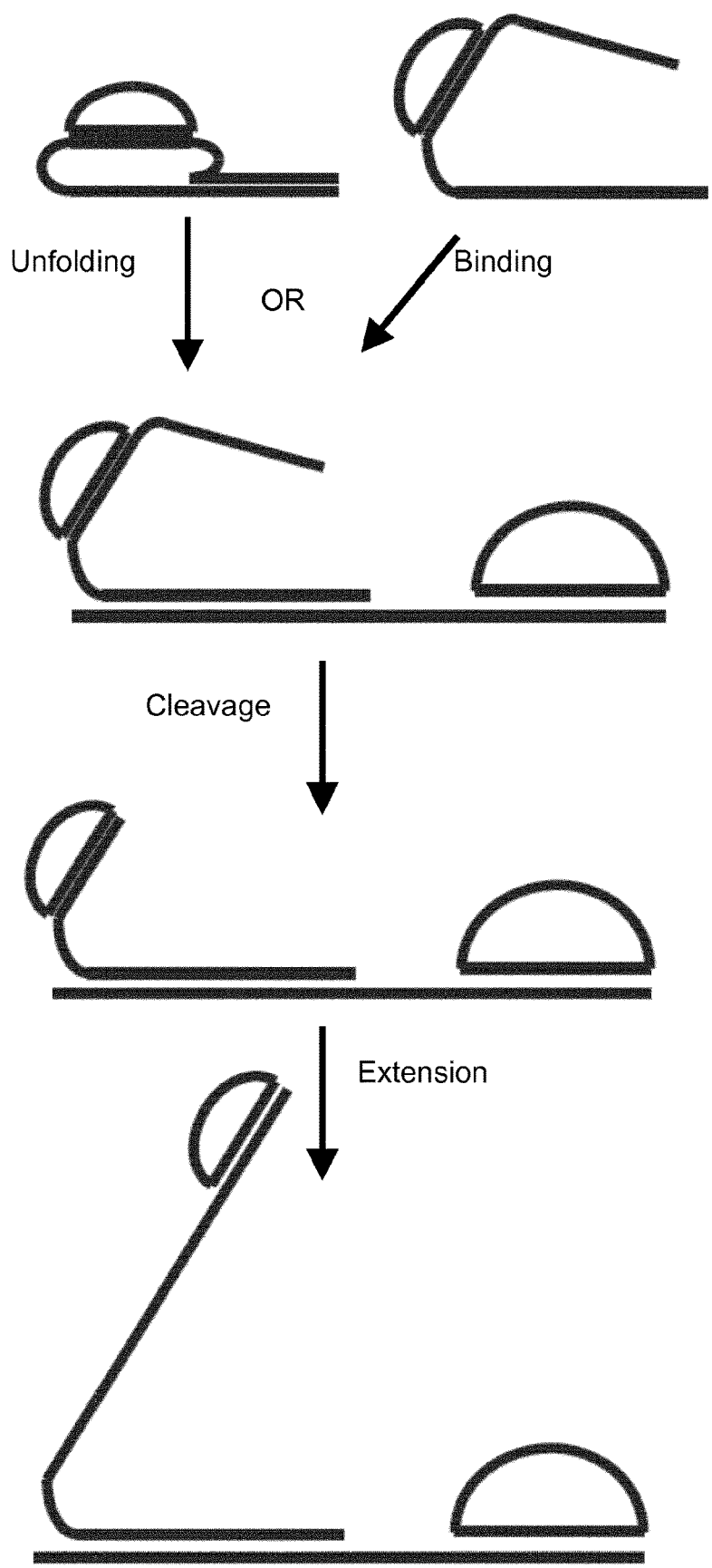

FIG. 11 shows two variants of a circle RCA probe. The probe on the left is unfolded by binding to the target nucleic acid molecule and subsequently cleaved. The probe on the right does not require a target interaction for cleavage to occur. The probe is depicted as hybridising to a first RCA product.

Figure 12:
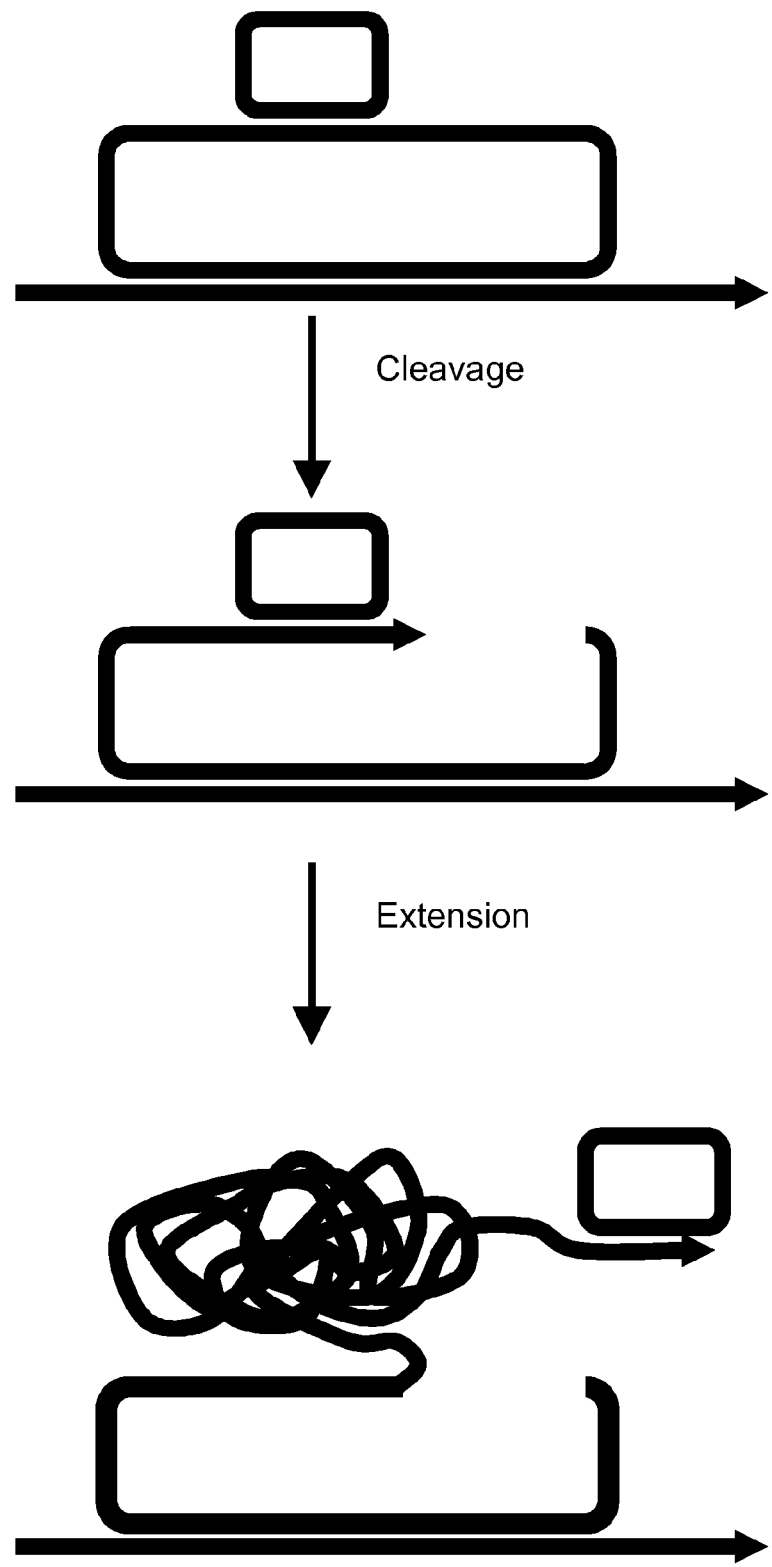

FIG. 12 shows a circle RCA probe, wherein the primer strand is also a circular oligonucleotide.

Figure 13:
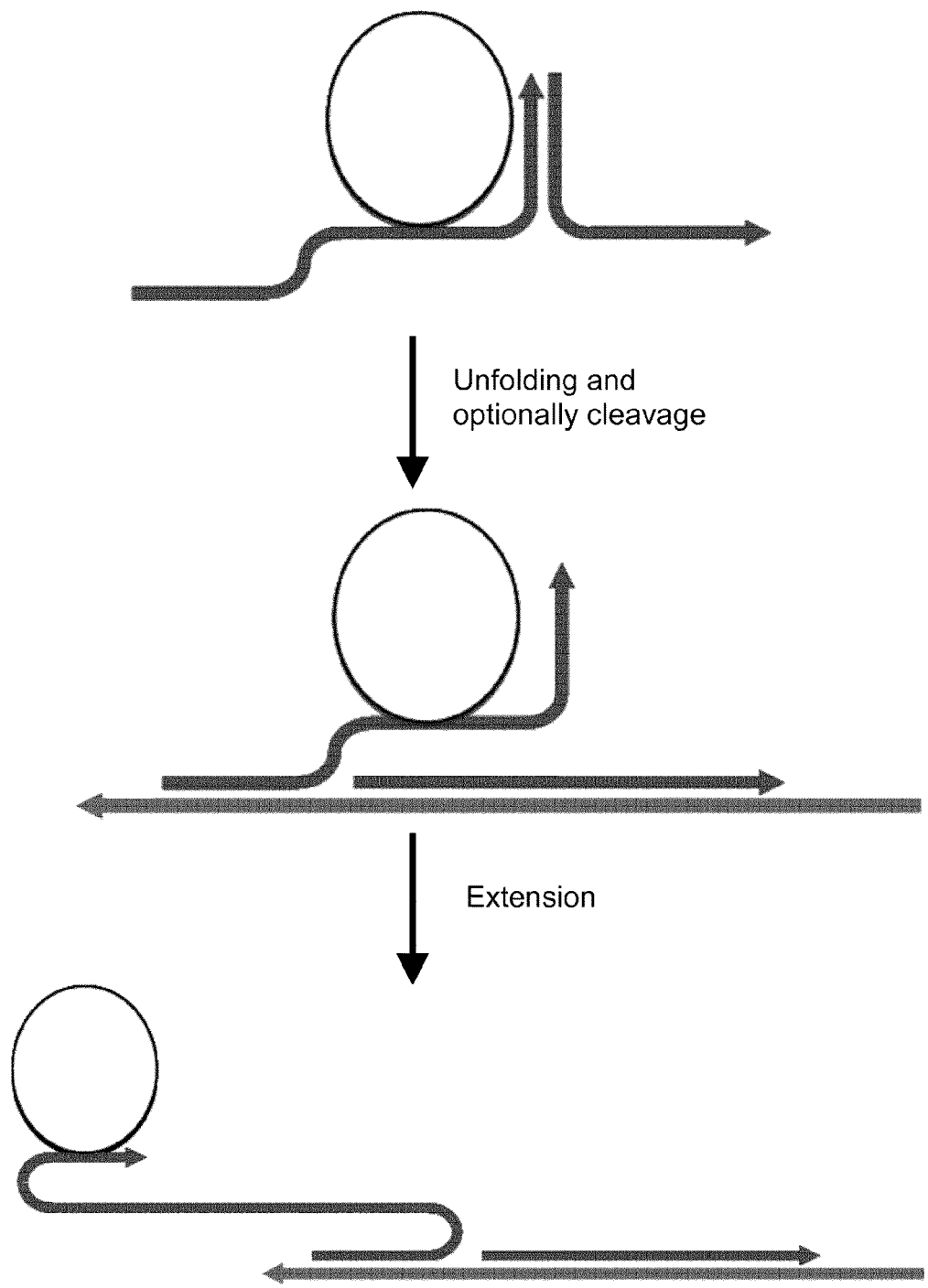

FIG. 13 shows a circle RCA probe comprising an invasion strand. When the probe binds to its target nucleic acid molecule, the invasion strand is displaced from the probe to release the RCA primer.

Figure 14:
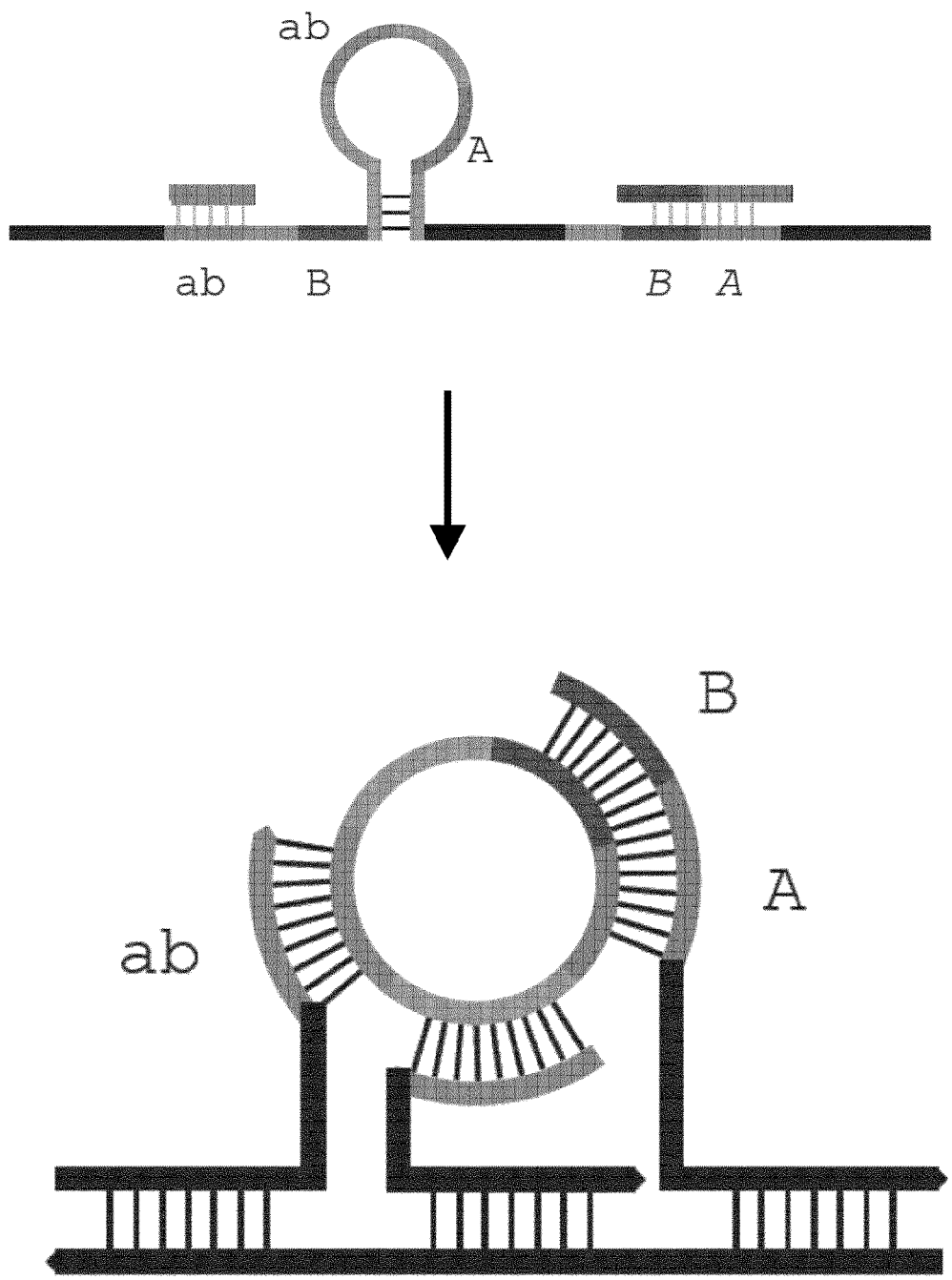

FIG. 14 shows a three-part RCA hairpin probe comprising two cleavage strands, wherein ab is the primer domain, the domain labelled A in the hairpin is complementary to the domain labelled A in the duplex and the domain labelled B directly adjacent to the stem-loop structure is complementary to the domain labelled B in the duplex. The domains in between ab and B, and to the right of the AB duplex, are cleavage domains.

Figure 15:
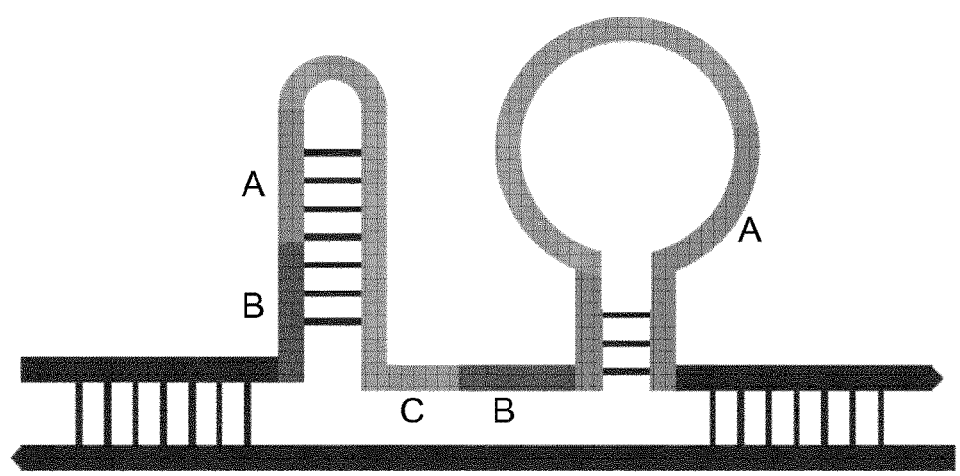

FIG. 15 shows a two-part hairpin RCA probe bound to a nucleic acid molecule (a first RCA product), wherein domains labelled A and B are complementary and C represents a cleavage domain.

Figure 16:
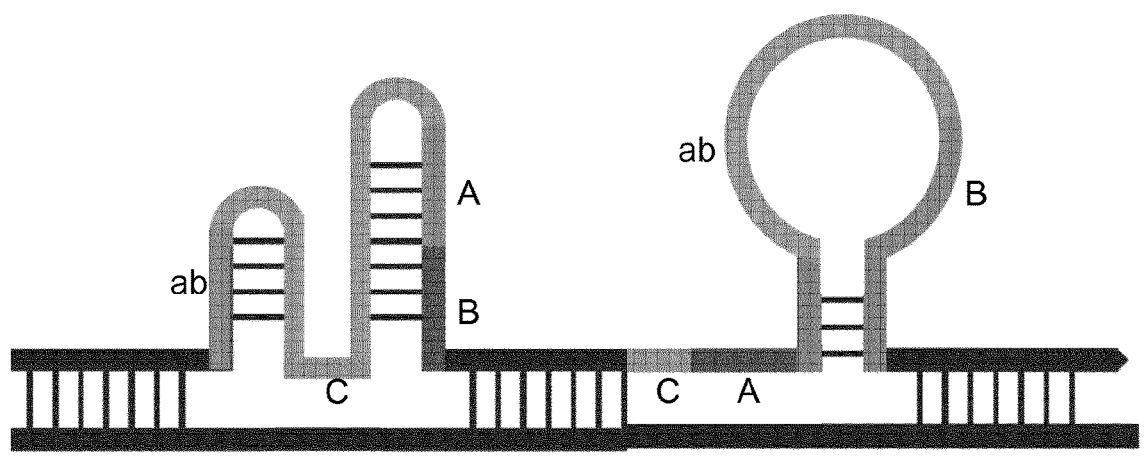

FIG. 16 shows a three-part hairpin RCA probe bound to a nucleic acid molecule (a first RCA product) wherein domains labelled A, B and ab are complementary and C represents a cleavage domain.

Figure 17:
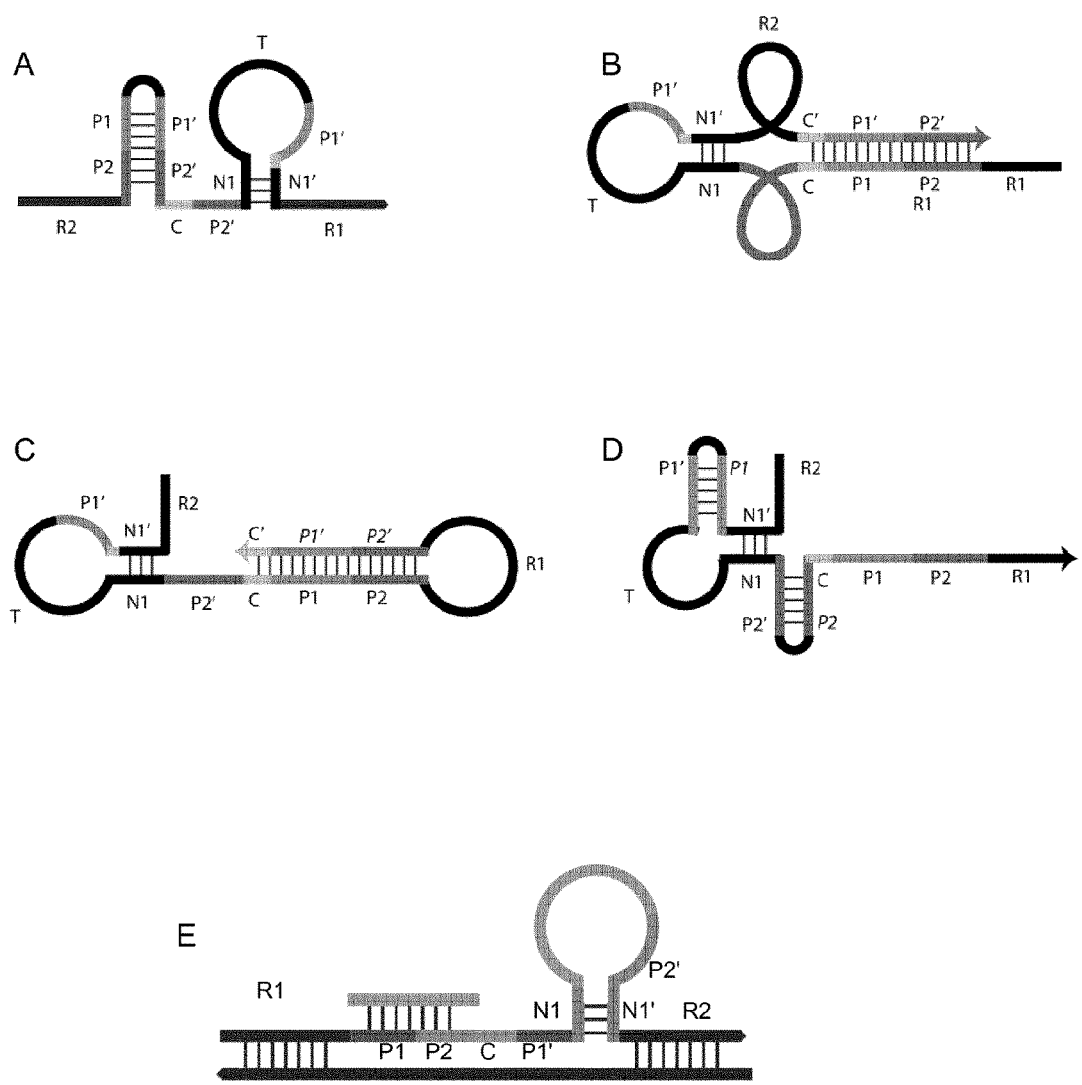

FIG. 17 shows a variety of two-part probes in (A)-(E), wherein the following domains are complementary: P1 and P1'; P2 and P2'; N1 and N1'; and C and C'. R1 and R2 are used to label target binding domains. C represents a cleavage domain.

Figure 18:
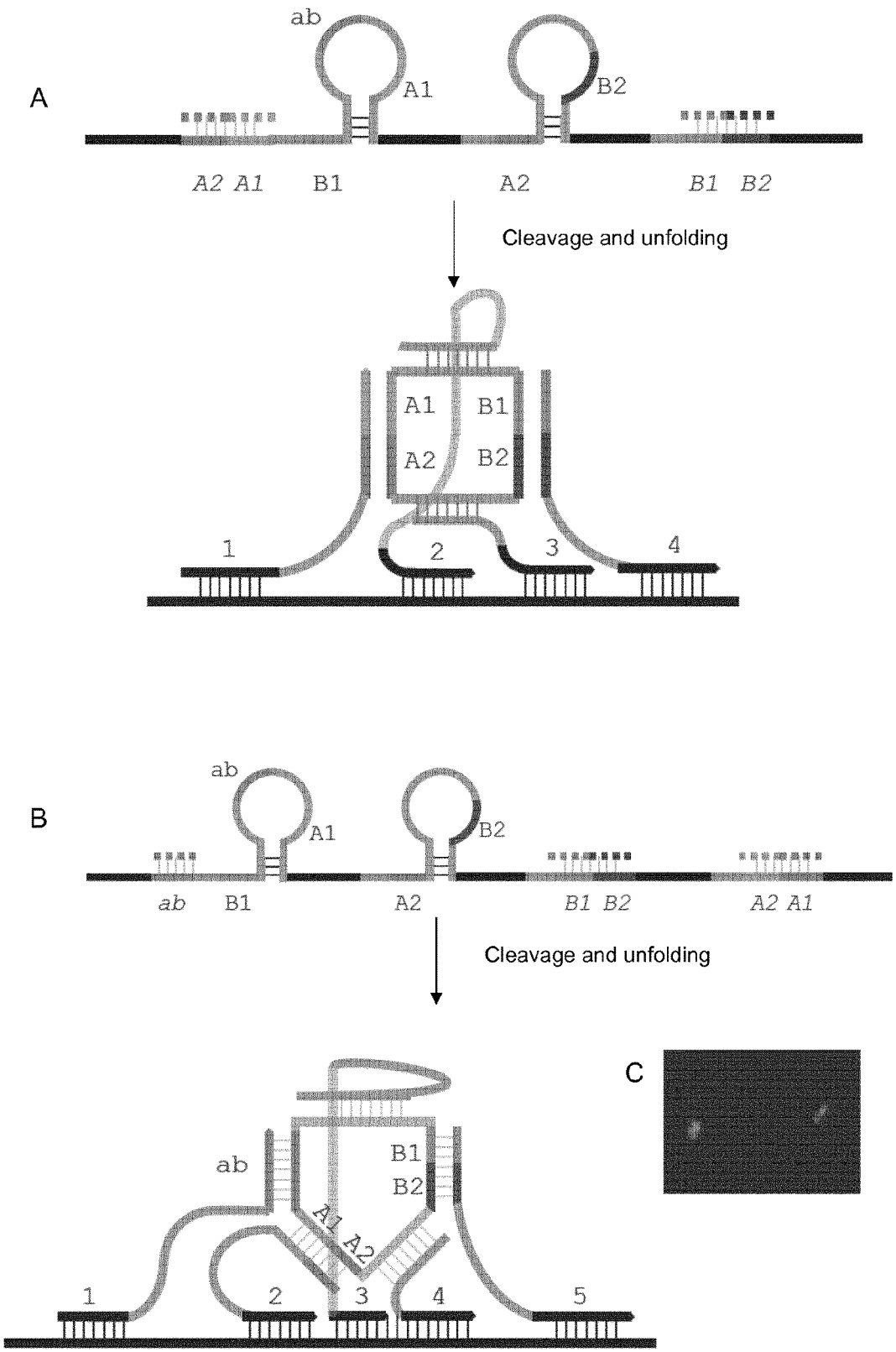

FIG. 18 shows four-part (A) and five-part (B) hairpin RCA probes bound to nucleic acid molecules, wherein domains labelled A1, A2, B1, B2 and ab are complementary. (C) shows dual labelled blobs resulting from the detection of an immobilized target nucleic acid molecule.

Figure 19:
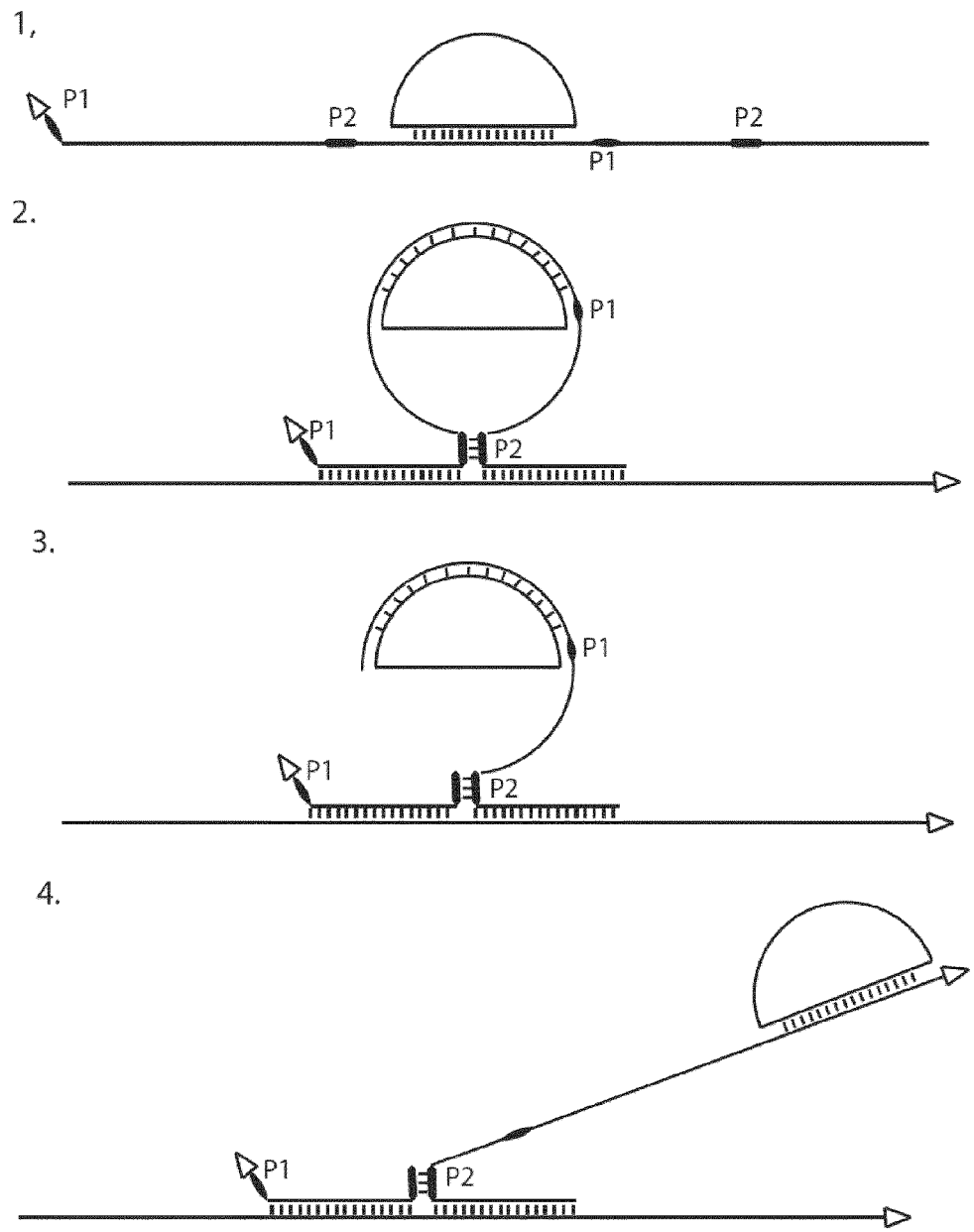

FIG. 19 shows a circle RCA probe wherein a cleavage domain is formed when the probe binds to the target nucleic acid molecule to form a stem loop structure. Domains labelled P2 represent complementary sequences.

Figure 1:
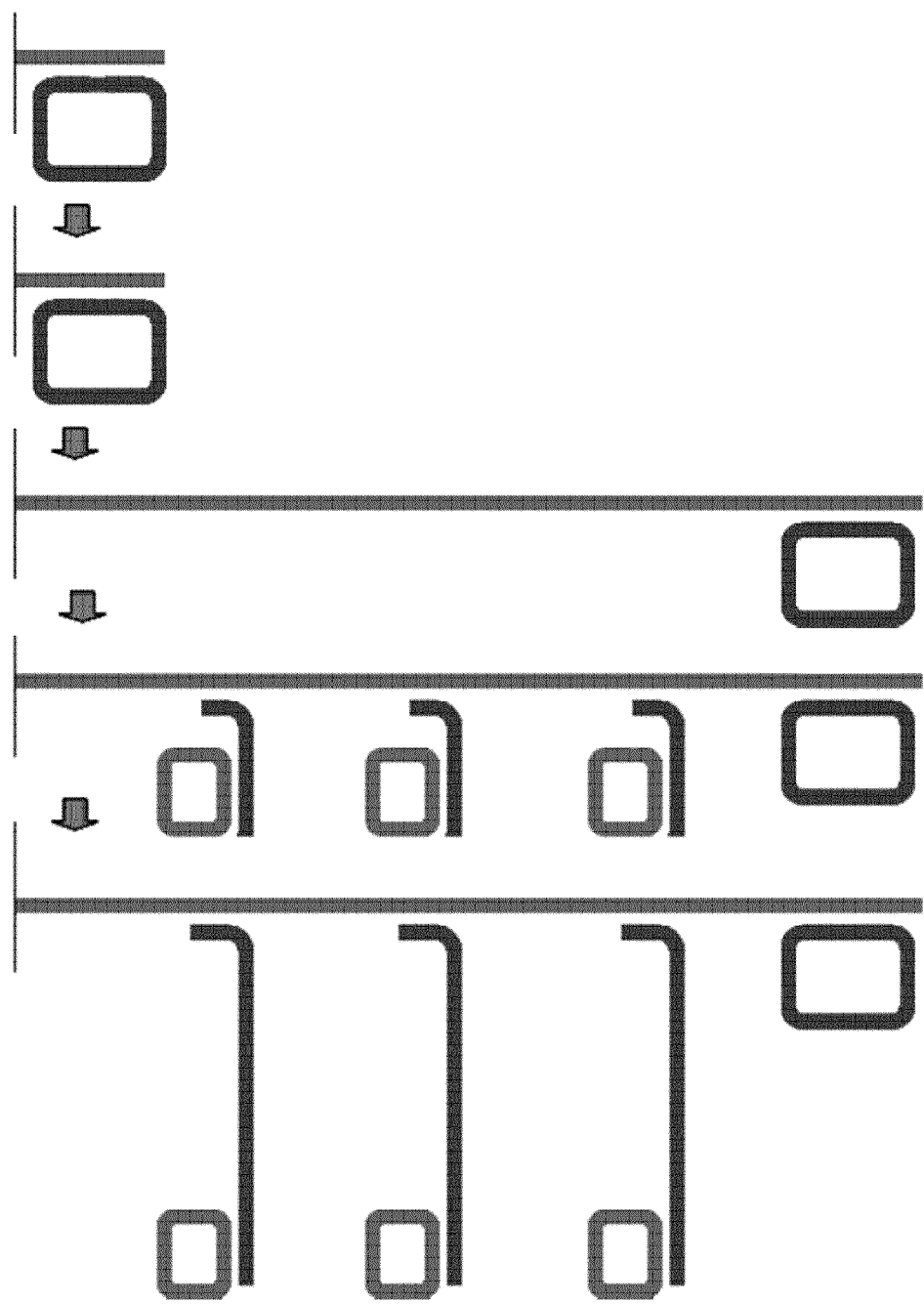
Figure 2:
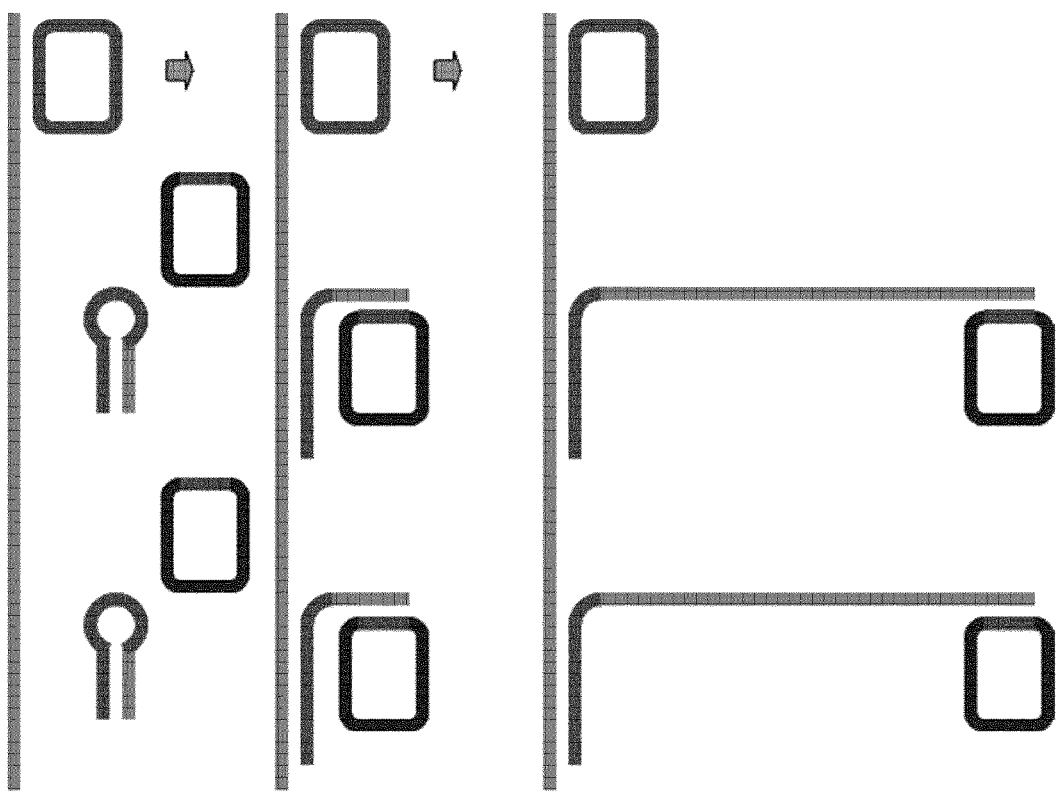
Figure 3:
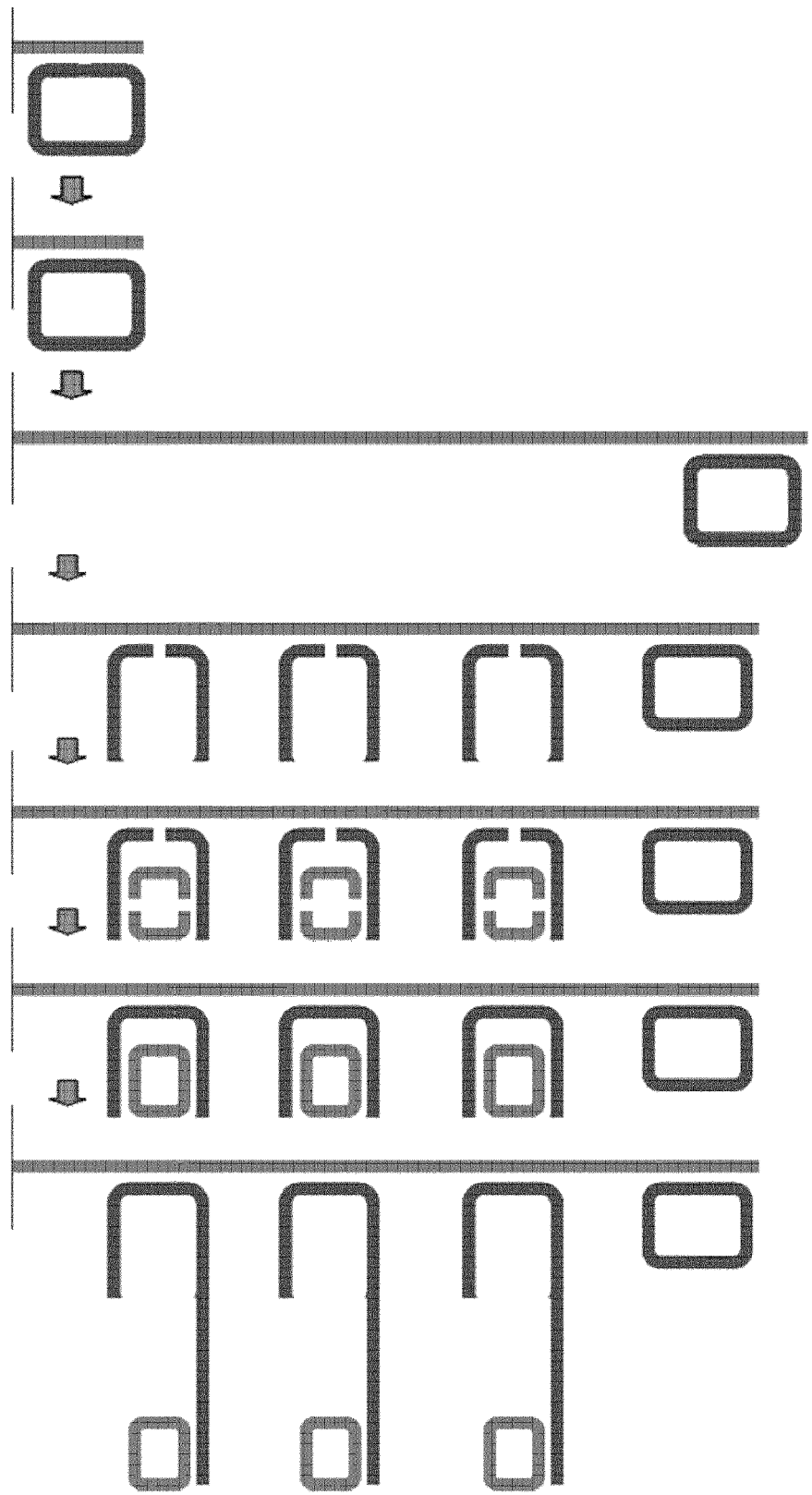
Figure 4:
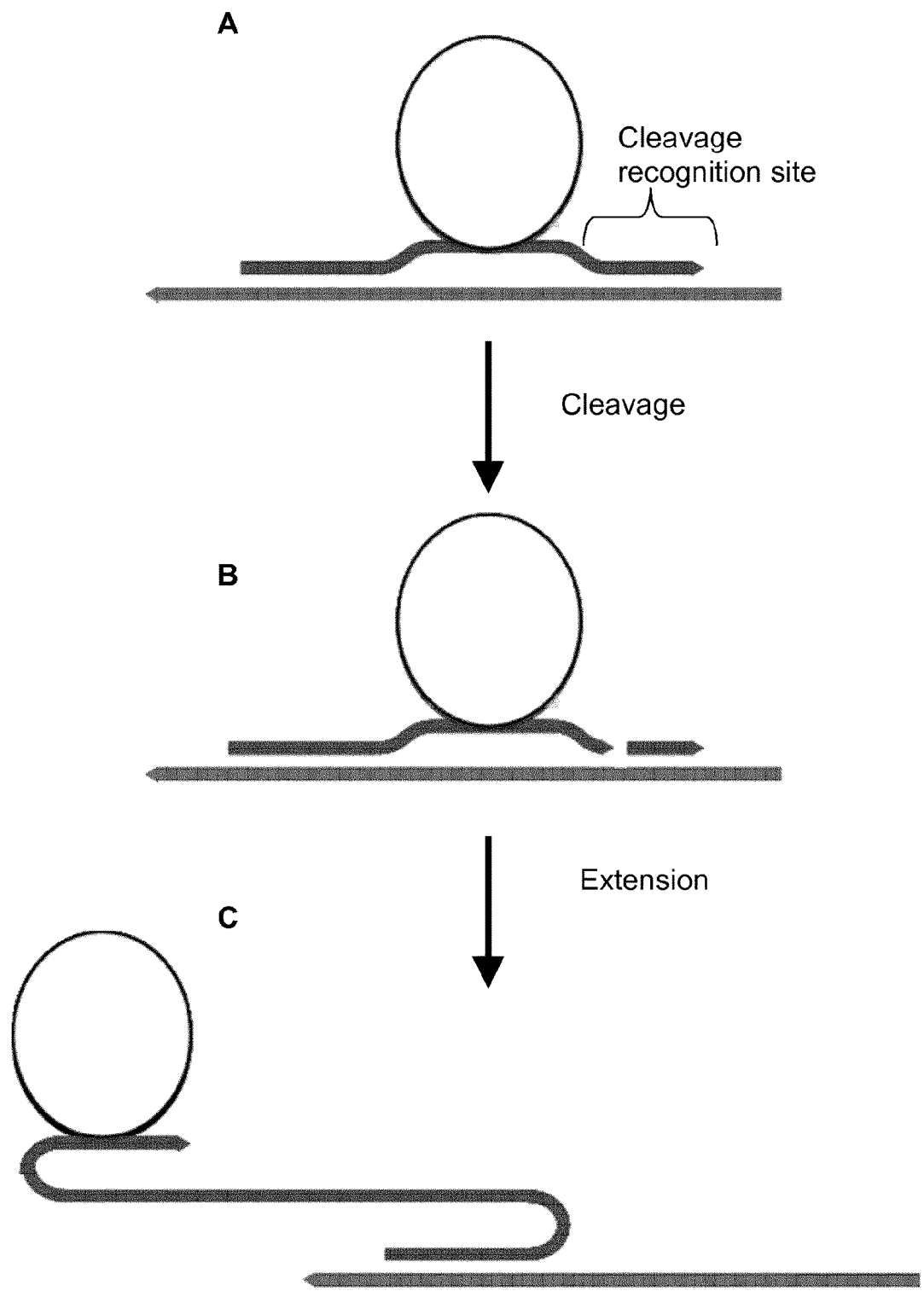
Figure 5:
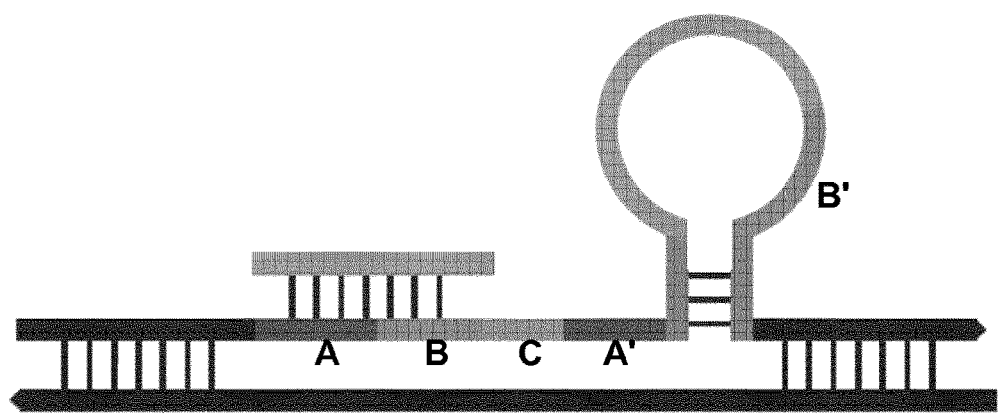
Figure 20:
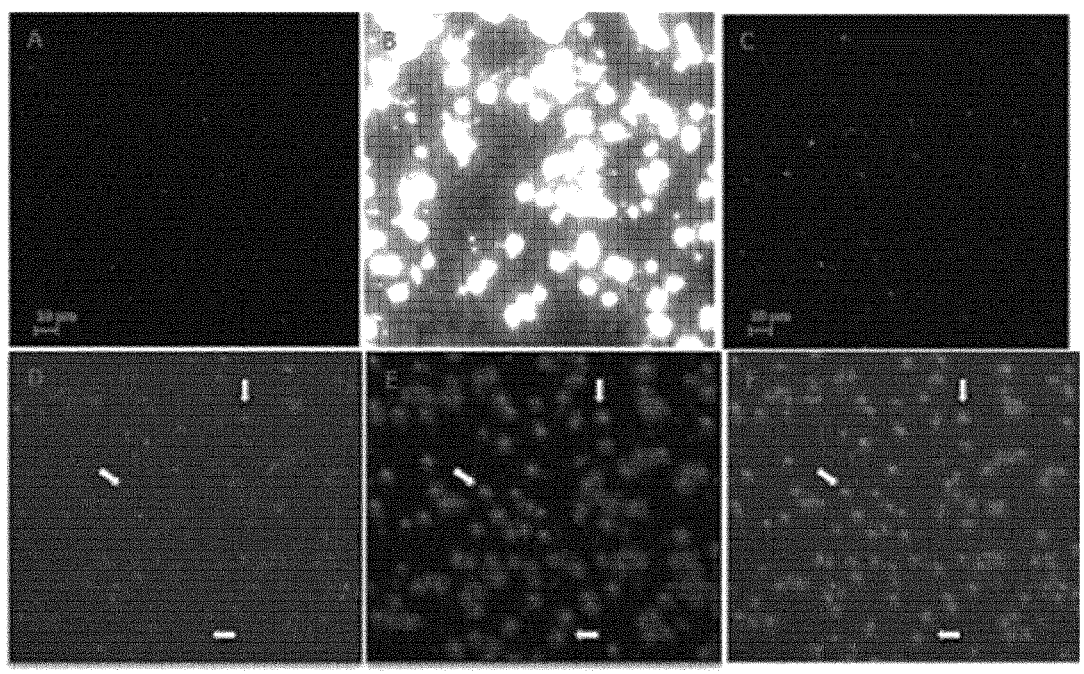

FIG. 20 shows the results of the experiment described in Example 1 using a sRCA reaction protocol as shown in FIG. 1. The super RCA product was generated by initiating the second RCA when the second RCA initiating probes bound to the first RCA product. (A) Only the first round of RCA was generated on the solid support. (B) Based on the first round of RCA generation, a second round of RCA was generated upon the hybridisation of the second RCA initiating probes to the first RCA product. (C) Without the first RCA product, a small amount of the second RCA product may be seen, indicating the initiating probe for the second RCA may generate a small amount of second RCA product by itself. The RCA products in pictures (A), (B) and (C) were labeled with the same fluorophore and the pictures were taken with the same exposure time (150 ms). (D) Only presented is the signal generated from the first round of RCA. (Exposure time: 1000 ms) (E) Only presented is the signal generated from the second round of RCA. (Exposure time: 33 ms) (F) represents the merged picture of (D) and (E). Picture (F) shown the co-localization between the first RCA products and second RCA products.

Figure 21:
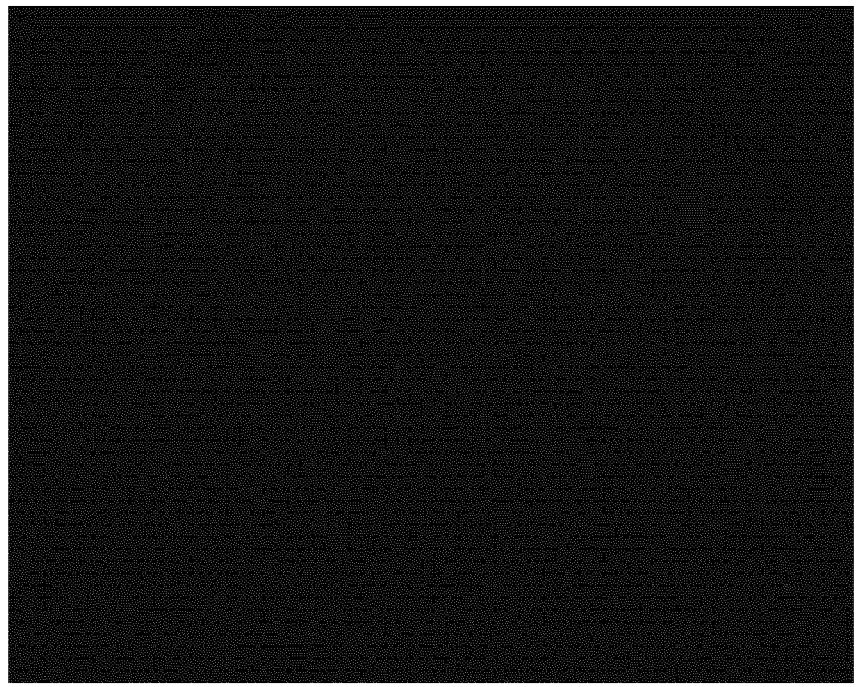
Figure 21:
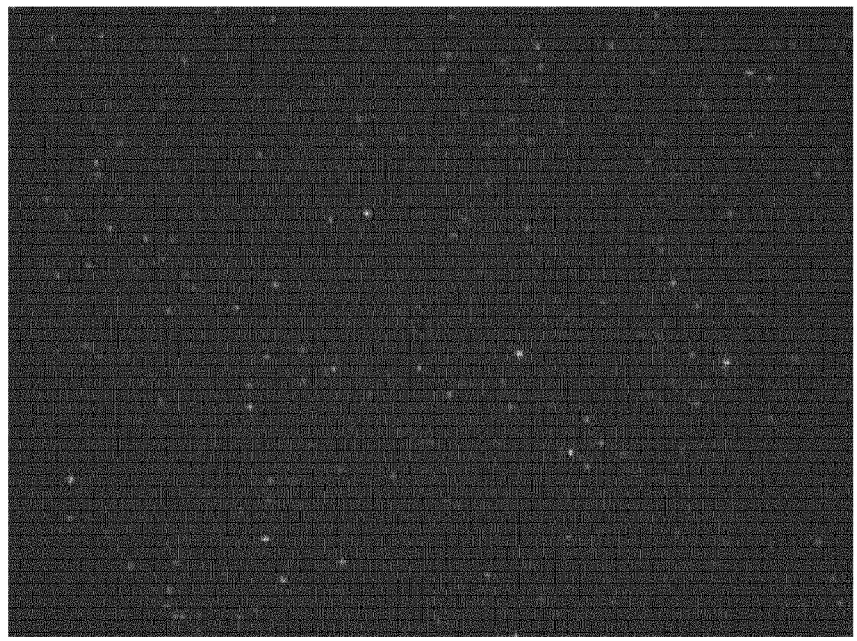

FIG. 21 shows the detection of a primary RCA product using a circle RCA probe, wherein (A) shows no secondary RCA products are generated in the absence of primary RCA product and (B) shows that the primary and secondary RCA products co-localise.

Figure 22:
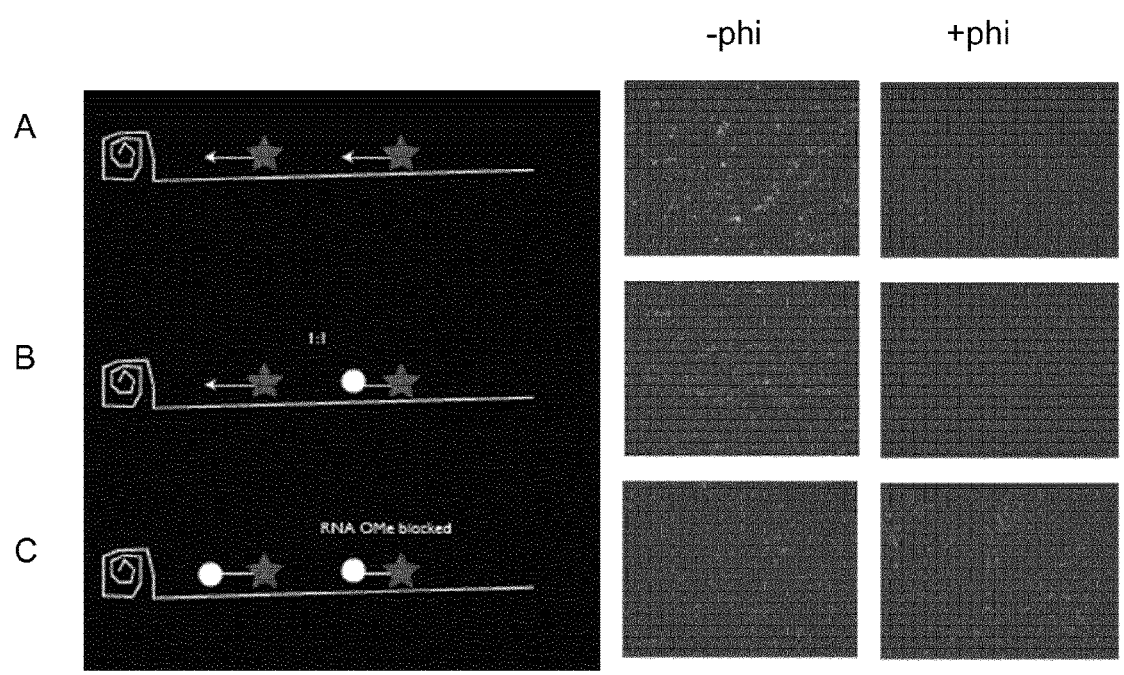

FIG. 22 shows the signal generated from the hybridisation of detection oligonucleotides to RCA products in the presence or absence of a polymerase with strand displacement activity. Detection oligonucleotides hybridised to a RCA product are depicted, wherein the label is illustrated as a star, oligonucleotides with a free 3' end are illustrated as an arrow and oligonucleotides blocked with three 2'-O-methylated RNA bases are illustrated as a dot.

Figure 23:
Figure 23:
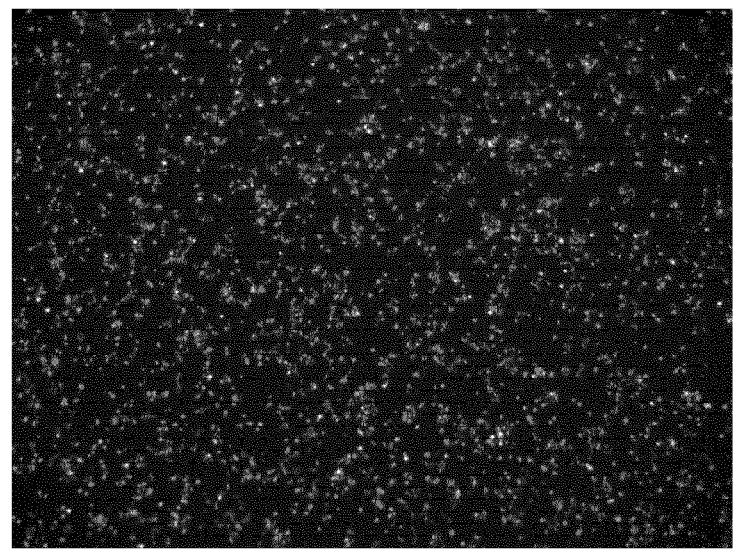
Figure 23:
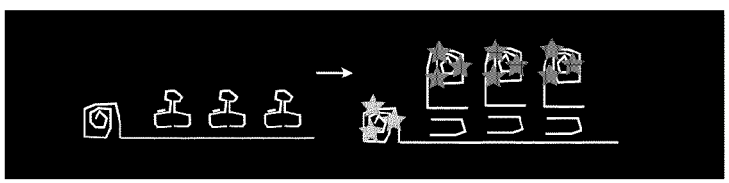
Figure 23:
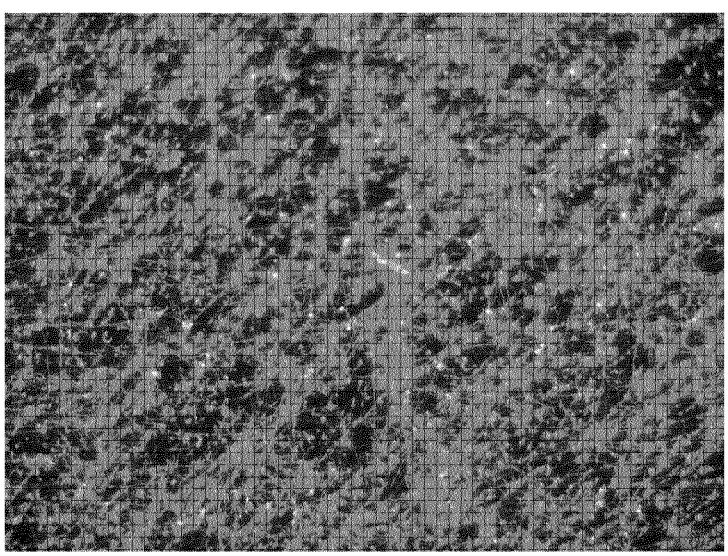

FIG. 23 shows a secondary RCA reaction using a padlock probe (A) or two-part hairpin RCA probe (B).

Figure 24:
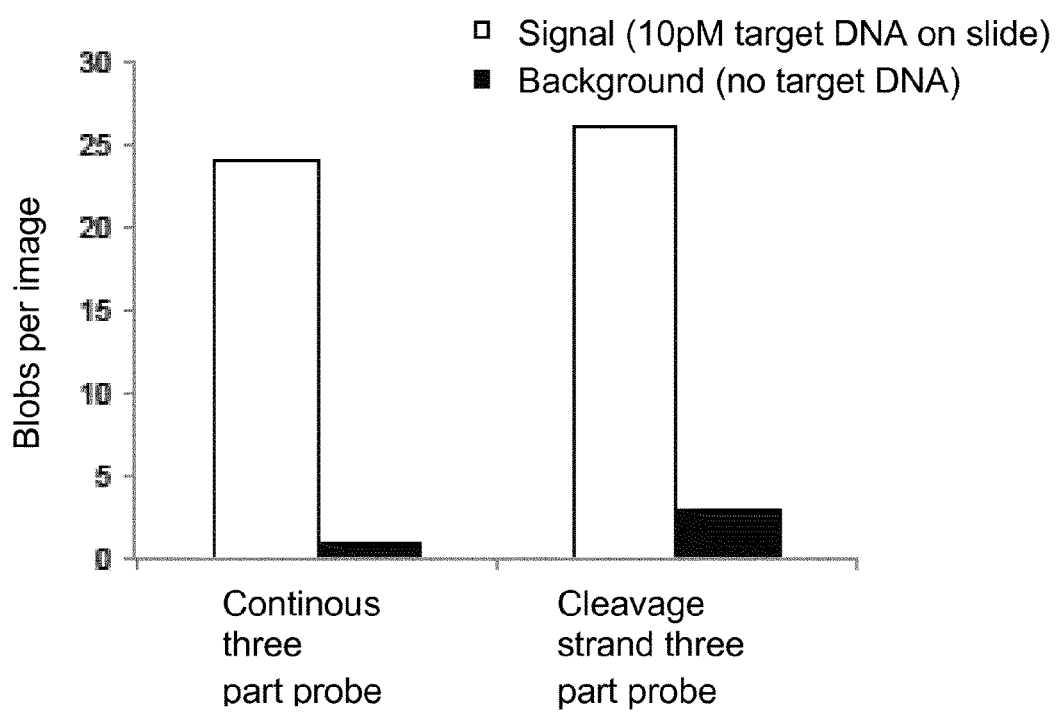

FIG. 24 shows a bar chart of the comparative results of a nucleic acid detection assay using a continuous three-part probe or a three-part probe comprising cleavage strands.

Figure 25:
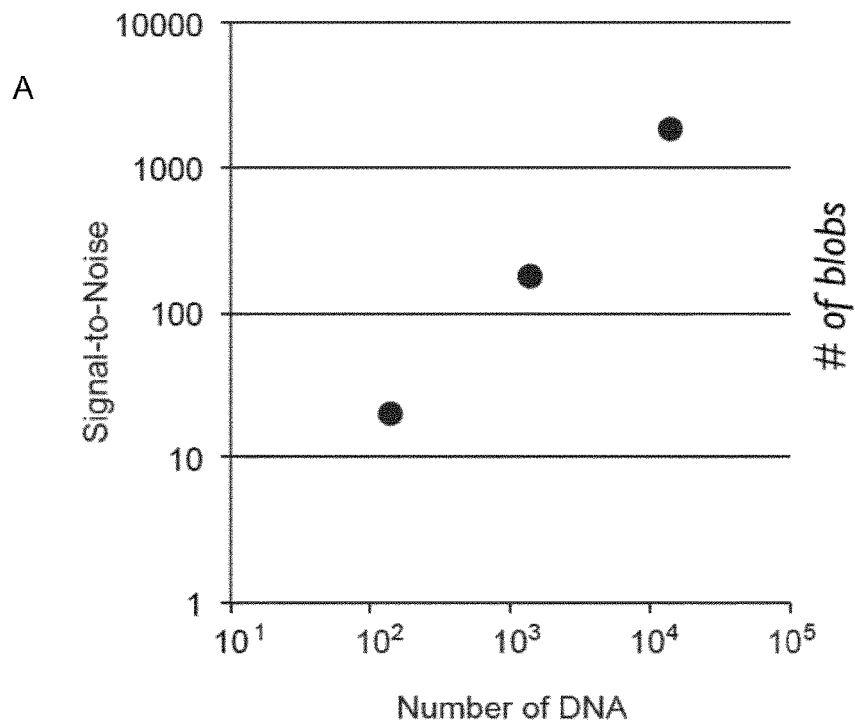
Figure 25:
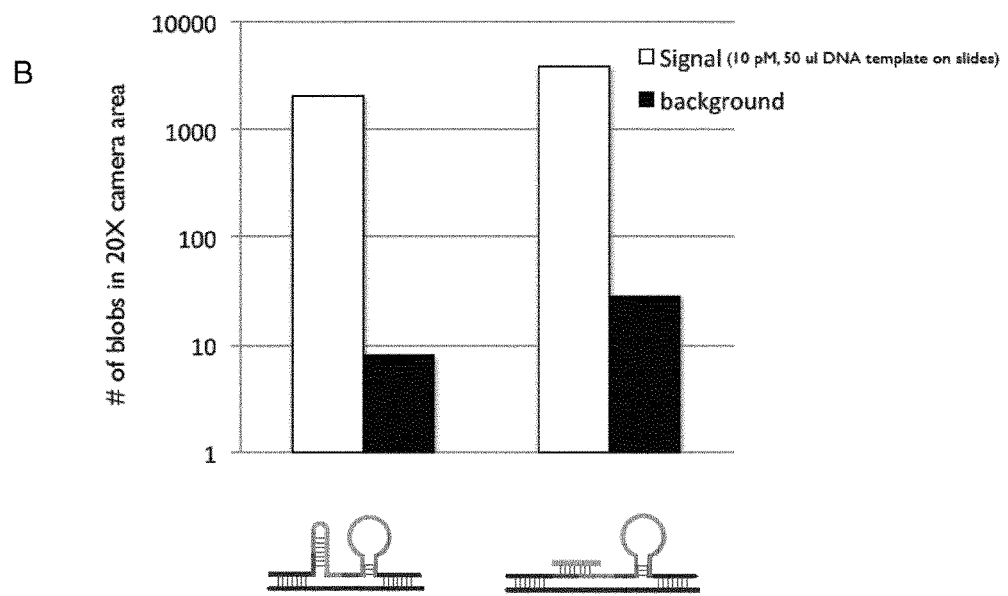

FIG. 25 shows (A) a graph of the signal:noise ratio of a two-part hairpin cleavage strand probe in the detection of a nucleic acid molecule immobilized to a substrate via a biotin/streptavidin interaction and (B) a bar chart of the comparative results of a nucleic acid detection assay using a continuous two-part probe or a two-part probe comprising a cleavage strand.

EXAMPLES

Example 1

Solid Phase sRCA Reaction

The sRCA principle was demonstrated using the probe depicted in FIG. 1. Probe generation The 1st and 2nd RCA templates were pre-ligated in solution separately to form RCA "probes" (primer/template complexes). 300 nM RCA template, 100 nM RCA primer were mixed with ligation buffer (1×T4 ligase buffer, 1 mM ATP and 0.05 U/µL T4 ligase) for 30 minutes at 37° C.

Immobilization of the 1st RCA Probe 100 fM dilution of the 1st RCA probe was prepared in 1×PBS. 50 µL of the 100 fM dilution was applied to the streptavidin coated slides (Codelink) for 30 minutes at room temperature. After the incubation, the slide was washed twice with washing buffer (1×PBS, 0.05% Tween 20).

Generation of the 1st RCA Product

After the removal of the washing buffer, RCA mix (1×phi29 buffer (Fermentas), 250 µM dNTP, 0.02 U/µL phi29 polymerase (Fermentas)) was added to the slides and incubated for 30 minutes at 37° C. After the incubation, the slide was washed twice with washing buffer (1×PBS, 0.05% Tween 20).

2nd RCA Probe Hybridization

The 2nd RCA probe was diluted to 1 nM in 1× hybridization buffer (Olink). 50 µL of the 1 nM 2nd RCA probe was applied to the slide for 30 minutes at 37° C. Afterthe incubation, the slide was washed twice with washing buffer (1×PBS, 0.05% Tween 20).

Generation of the 2nd RCA Product

After the removal of the washing buffer, RCA mix (1×phi29 buffer (Fermentas), 250 µM dNTP, 0.02 U/µL phi29 polymerase (Fermentas)) was added to the slide and incubated for 30 minutes at 37° C. After the incubation, the slide was washed twice with washing buffer (1×PBS, 0.05% Tween 20).

Detection Oligo Hybridization

Oligos with specific sequence complementary to the first RCA product and second RCA product were labelled with FITC and Cy3, respectively. The two detection oligos were diluted to 100 nM in hybridization buffer (2×SSC, 20% Formamide). The diluted oligos were applied to the slide and incubated for 30 minutes at 37° C. After the incubation, the slide was washed twice with washing buffer (1×PBS, 0.05% Tween 20). The images of the RCA probes are show in FIG. 20.

Example 2

Circle RCA Probe for the Detection of a RCA Product

The Example demonstrates the utility of a circle RCA probe in a super RCA (sRCA) reaction, as depicted in the unfolding RCA reporter probe embodiment of FIG. 11.

A pre-ligated padlock was amplified via RCA using phi29 polymerase for 1 h at 37° C. The circle RCA probe was then spiked-in and the reaction was allowed to proceed for 1 h at 37° C. followed by 10 min at 65° C. to inactivate the phi29 polymerase. Cy-3 or FITC-labeled oligos targeting the primary and secondary RCA products, respectively were subsequently added to the sRCA reaction and allowed to hybridize for 20 min at 55° C. The sRCA products were allowed to adhere to poly-L-lysine coated slides and then visualized via epifluorescent microscopy with a 20× objective, exposure time 1500 ms.

FIG. 21A shows that no secondary RCA products were generated in the absence of a primary RCA product. FIG. 21B shows that the primary and secondary RCA products co-localise.

Example 3

Importance of Blocking 3' End of Probes to Avoid Target Templated Extension and Subsequent Displacement of Probes from First (Primary) RCA Products Prior to experiment, the streptavidin coated glass slide (SurModics) was compartmentalized with secure-Seal 8 (Grace Bio-labs). Fifty μl of 1 pM synthetic biotinylated DNA template was incubated in 1×PBS in each reaction chamber at 37° C. for 60 min. After incubation, the slides were blocked with blocking buffer (0.1% BSA (Sigma), 100 nM goat IgG (Sigma), 1 mM biotin (Sigma), 10 ng/μl salmon sperm DNA (Sigma), 5 mM EDTA, 1×PBS and 0.05% Tween 20) at 37° C. for 60 min. A washing step, with two repetitions of 50 μl 1×PBS 0.05% Tween20, was performed before every addition of a new mix, to remove of previous incubation reagents.

Fifty μl ligation mix (1×NEB4 buffer (NEB), 0.5 μg/μl BSA (NEB), 15 units of T4 DNA ligase (Fermentas) and 0.5 mM ATP (Fermentas)) and 100 nM of padlock probe was added to the reaction chambers. The ligation reaction was incubated at 37° C. for 30 min, followed by washes and the addition of 50 μl rolling circle amplification (RCA) mix (1×phi29 buffer (Fermentas), 0.2 μg/μl purified BSA (NEB), 0.25 mM dNTPs (Fermentas), 25 units of phi29 (Fermentas)). The RCA reactions were carried out at 37° C. for 60 min.

Fifty μl detection mix containing 100 nM detection oligonucleotides in 20% Formamide (Sigma) and 2×SSC (300 mM NaCl, 30 mM Na-citrate) was added in each chamber. Incubation was carried out at 37° C. for 30 min. Detection oligonucleotides labelled with Alex555 (illustrated as a star in FIG. 22) used in this experiment were identical in their binding sequence to the RCA products but different in their 3' ends, which were either free (illustrated as an arrow in FIG. 22) or blocked with three 2'-O-methylated RNA bases (illustrated as a dot in FIG. 22). RCA products were labelled with one of the two detection oligonucleotides (FIGS. 22A and C) or both detection oligonucleotides with 1:1 ratio (FIG. 22B). The labelling reactions were done in duplicates.

After hybridization of detection oligonucleotides, chambers were washed. Fifty μl of 1×PBS, 0.05% Tween20 was added in one of the replicated chambers (FIG. 24 column labelled-phi), whereas 50 μl of phi29 mix (1×phi29 buffer (Fermentas), 0.2 μg/μl purified BSA (NEB), 0.25 mM dNTPs (Fermentas), 25 units of phi29 (Fermentas)) was added in the other replicated chamber (FIG. 22 column labelled phi+). Incubation was carried out at 37° C. for 60 min. Thereafter slides were washed, dried, mounted with VectaShield (Immunkemi) and a cover slip and imaged.

FIG. 22 demonstrates that the nucleic acid molecules hybridized to a RCA product are displaced when target templated extension is allowed to occur. In this example detection oligonucleotides were displaced, but the principle is applicable to detection probes, e.g. RCA reporters, that are required to remain attached to the target nucleic acid molecule.

Example 4

A Comparison of Secondary RCA Using a Padlock Probe and a RCA Reporter (sRCA)

Figure 6:
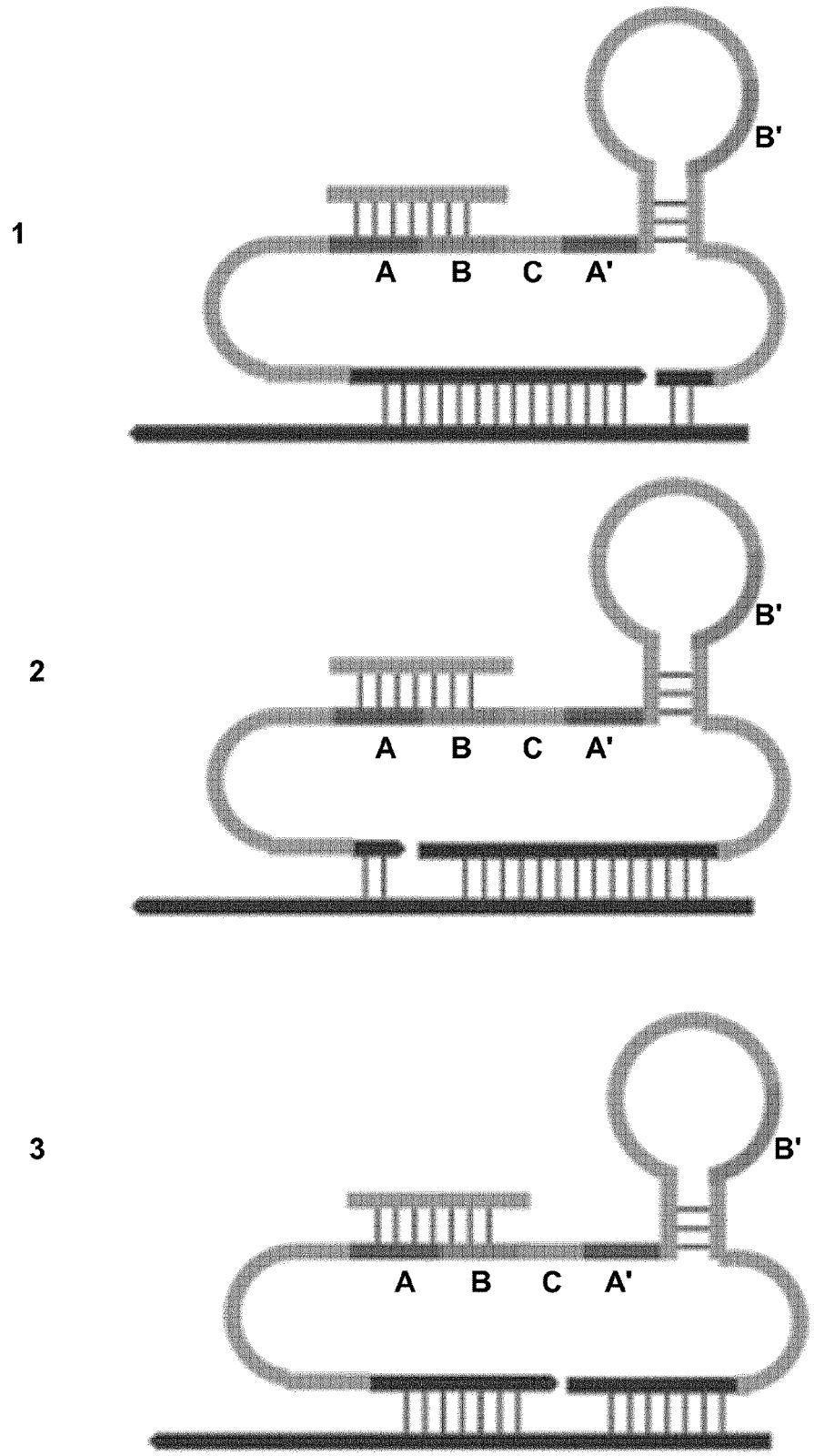
Figure 7:
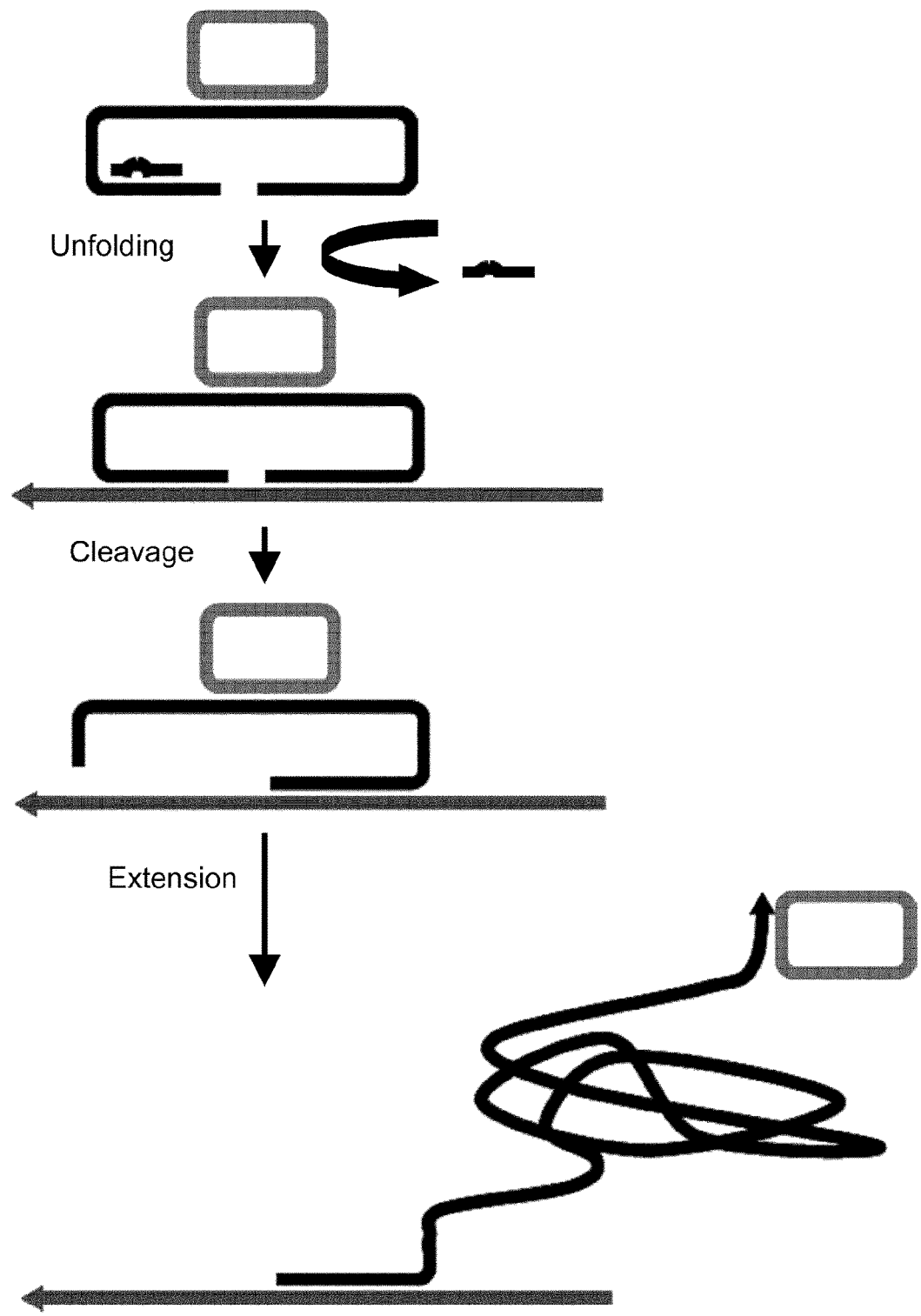
FIG. 7 shows a circle RCA probe comprising a protection strand. The protection strand is displaced when the probe binds to its target nucleic acid molecule.
Figure 8:
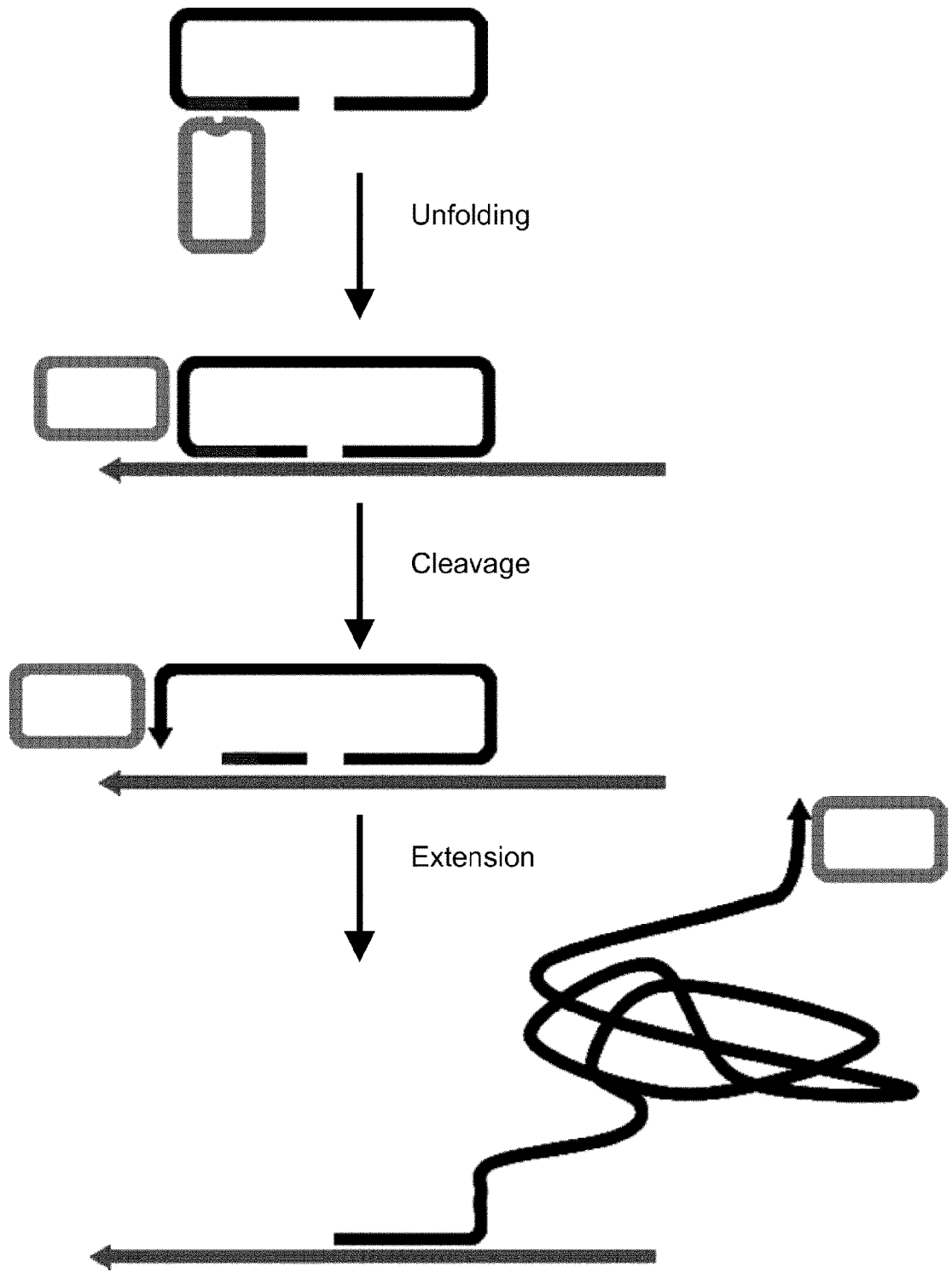
FIG. 8 shows a circle RCA probe, wherein the RCA template functions as a protection strand. The RCA template protection strand is displaced to a second RCA template complementary domain when the probe binds to its target nucleic acid molecule.

Primary RCA products were generated on a slide by the protocol described in Example 3. Fifty μl of ligation mix (1×NEB4 buffer (NEB), 0.5 μg/μl BSA (NEB), 15 units of T4 DNA ligase (Fermentas) and 0.5 mM ATP (Fermentas)) and 100 nM of padlock probes or 20 nM of target ligation dependent two-part hairpin probes (comprising cleavage strands, e.g. as shown in FIG. 6) were added to the reaction chambers. The ligation reaction was incubated at 37° C. for 60 min. After washes, 50 μl of 3' end termination mix (1× terminal transferase buffer (NEB), 0.25 mM CoCl2 100 nM dUTP, 10 units terminal transferase) was added and incubated in each reaction chamber at 37° C. for 30 min. After washes, 50 μl UNG mix (1×NEB4 buffer, 0.5 μg/μl BSA, 5 units of UNG) was added to the chamber, which was incubated at 37° C. for 30 min. Thereafter 50 μl 1×PBS, 0.05% Tween20 was added to the chamber applied with padlock probes (FIG. 23A), whereas unfolding and cleavage reactions were carried out in the chamber applied with two-part probes (FIG. 23B): Firstly, 50 μl of unfolding and cleavage mix (1×NEB4 buffer (New England Biolabs (NEB), 0.5 μg/μl BSA (NEB), 50 units of Nb BtsI (NEB), 50 units of MlyI (NEB)) and 500 pmol of additional cleavage strands were added to each well. After incubation at 37° C. for 60 min followed by washes, 50 μl of additional cleavage mix (1×NEB4 buffer (NEB), 0.5 μg/μl BSA (NEB) and 5 unit of UNG (Fermentas) was added to remove the cleavage strands. The reaction was incubated at 37° C. for 30 min. After washes, 50 μl of ligation mix (1×NEB4 buffer (NEB), 0.5 μg/μl BSA (NEB), 15 units of T4 DNA ligase (Fermentas) and 0.5 mM ATP (Fermentas)) was added to the reaction chambers. The ligation reaction was incubated at 37° C. for 30 min. Finally, secondary RCA reactions in both chambers were initiated by the addition of 50 μl of rolling circle amplification (RCA) mix (1×phi29 buffer (Fermentas), 0.2 μg/μl purified BSA (NEB), 0.25 mM dNTPs (Fermentas), 25 units of phi29 (Fermentas)). The RCA reactions were carried out at 37° C. for 60 min. The primary and secondary RCA products were visualized by hybridization of 10 nM detection oligonucleotides labelled with different fluorophores, by incubation at 37° C. for 30 min. Thereafter slides were washed, dried, mounted with VectaShield (Immunkemi) and a cover slip and imaged.

FIG. 23 shows that the signal generated using two-part RCA reporter probes is significantly enhanced in comparison to a secondary RCA performed using padlock probes.

The following Examples 5 to 7 demonstrate the functionality of various RCA reporters using synthetic DNA targets as a substitute for a primary RCA product.

Example 5

Three Part Hairpin RCA Probe

The utility of the "three-part" RCA probe was shown using a nucleic acid molecule. Two variants of the "three-part" probe were tested, i.e. a single stranded probe comprising three hairpin structures and a partially double stranded probe comprising a hairpin structure and two cleavage strands.

Fifty µl of 10 pM synthetic biotinylated DNA template was incubated in 1×PBS on a streptavidin coated glass slide (SurModics) at 37° C. for 60 min, with no DNA spiked in 1×PBS as negative control. After incubation, the slides were blocked with blocking buffer (0.1% BSA (Sigma), 100 nM goat IgG (Sigma), 1 mM biotin (Sigma), 10 ng/µl salmon sperm DNA (Sigma), 5 mM EDTA, 1×PBS and 0.05% Tween 20) at 37° C. for 60 min.

Prior to the experiment, the streptavidin coated slide was compartmentalized with secure-Seal 8 (Grace Bio-labs). A washing step, with two repetitions of 50 µl 1×PBS, 0.05% Tween20, was added before every new addition of reagent mixes, for removal of previous incubation reagents.

The three-part probe comprising cleavage strands was prepared by incubation of the cleavage strands with the RCA template strand in 100:1 molar ratio in Mg hybridization buffer (50 mM KAc, 20 mM TrisAc, 10 mM MgAc and 1 mM DTT) at 37° C. for 60 min. The single stranded (continuous) probe was incubated in 1 M NaCl at 95° C. for 5 min and cooled to 20° C. with temperature decrease rate at 1° C./sec to allow the formation of the hairpin structures. The probes were then diluted in blocking buffer to 20 nM and 50 µl of each probe was applied to the reaction chamber comprising the immobilized target nucleic acid molecules. After incubation at 37° C. for 60 min, the unbound probes were removed by washes. A series reactions were carried out to release/generate the RCA nucleic acid components and amplification of RCA template.

First 50 µl unfolding and cleavage mix (i.e. primer and RCA template release mix) (1×NEB4 buffer (New England Biolabs (NEB), 0.5 µg/µl BSA (NEB), 50 units of Nb BtsI (NEB), 50 units of MlyI (NEB)) and 500 pmol cleavage strands were added to each well. The unfolding mix did not contain cleavage strands in the reaction comprising the continuous (single stranded) three-part RCA reporter.

After incubation at 37° C. for 60 min followed by washes, 50 µl of additional cleavage mix (e.g. to remove the cleavage strands or to release RCA components) was added. The cleavage mix for the three-part probe comprising cleavage strands contained: 1×NEB4 buffer (NEB), 0.5 µg/µl BSA (NEB) and 5 units of UNG (Fermentas), 1 µg/µl BSA (NEB), 5 units of UNG (Fermentas) and 5 units of EndoIV (Fermentas). The additional cleavage mix for the continuous three-part probe contained: 1× unfolding buffer (20 mM Tris-HCl, 30 mM NaCl, 1 mM EDTA, 100 mM KCl and 1 mM DTT), 1 µg/µl BSA (NEB), 5 units of UNG (Fermentas) and 5 units of EndoIV (Fermentas). The reaction was incubated at 37° C. for 30 min to release the RCA nucleic acid components. After washes, 50 µl of ligation mix (1×NEB4 buffer (NEB), 0.5 µg/µl BSA (NEB), 15 units of T4 DNA ligase (Fermentas) and 0.5 mM ATP (Fermentas)) was added to the reaction chambers. The ligation reaction was incubated at 37° C. for 30 min, followed by washes and the addition of 50 µl of rolling circle amplification (RCA) mix (1×phi29 buffer (Fermentas), 0.2 µg/µl purified BSA (NEB), 0.25 mM dNTPs (Fermentas), 25 units of phi29 (Fermentas)). The RCA reactions were carried out at 37° C. for 60 min. The RCA products were visualized by hybridization of 10 nM fluorescently labelled probes (detection probes), by incubating at 37° C. for 30 min, followed by washes and ethanol series. Thereafter slides were mounted with VectaShield (Immunkemi) and a cover slip and imaged. The microscopic images were analyzed with ImageJ and the blobs were enumerated.

FIG. 24 shows that the continuous three-part probe generates a similar signal to the three-part probe comprising cleavage strands in the presence of the target analyte. Both probes shows a very low signal in the absence of target analyte. The continuous the three-part probe shows a better signal to noise ratio than the cleavage strand three-part probe.

Example 6

Continuous and Cleavage Strand Two-part Probes in the Detection of a Nucleic Acid Molecule The utility of the "two-part" RCA probes was shown using a nucleic acid molecule. The target nucleic acid was immobilized on a glass slide using two different techniques. Two variants of the "two-part" probe were tested, i.e. a continuous probe comprising two hairpin structures and a partially double stranded probe comprising a hairpin structure and a cleavage strand.

Synthetic DNA Template Immobilization Synthetic biotinylated DNA template in 10 µl 1×PBS was contacted with a streptavidin coated glass slide (SurModics) at 55° C. for 10 min. Alternatively, DNA template was hybridized to slides in 50 µl 1×PBS at 37° C. for 60 min with 1×PBS as a negative control. After incubation, the slides were blocked with blocking buffer (0.1% BSA (Sigma), 100 nM goat IgG (Sigma), 1 mM biotin (Sigma), 10 ng/µl salmon sperm DNA (Sigma), 5 mM EDTA, 1×PBS and 0.05% Tween 20) at 37° C. for 60 min. Prior to the experiment, the streptavidin coated slide was compartmentalized with secure-Seal 8 (Grace Bio-labs). A washing step, with two repetitions of 50 µl 1×PBS 0.05% Tween20, was performed before every addition of new reagent mixes, for removal of previous incubation reagents.

Assembly of Continuous Probes

Limited by the available DNA synthesis service (single stranded DNA are delivered up to 200 bp), two part (and three part) continuous probes were ordered in their constituent parts. Probes were assembled by incubation of all parts with equal molar ratio in ligation mix (1× NEB4 buffer (NEB), 0.5 mM ATP (Fermantas), 0.6 unit/µl T4 DNA ligase) at 37° C. for 30 min. The reaction mix was applied in 6% TBE-Urea gel (Life Technologies) according to manufacture's manual. The probes were then recovered by purifying DNA fragments at the correct sizes from the gel.

Preparation and Hybridization of Two-Part Probes

Two-part probes with hybridized cleavage strands were prepared by incubation of cleavage strands with the RCA template strand in 100:1 molar ratio in Mg hybridization buffer (50 mM KAc, 20 mM TrisAc, 10 mM MgAc and 1 mM DTT) at 37° C. for 60 min. Two-part continuous probes were prepared by incubating the probes in 1 M NaCl at 95° C. for 5 min and cooling down to 20° C. with temperature decrease rate at 1° C./sec. The probes were then diluted in blocking buffer to 20 nM of which 50 µl were applied to the reaction chamber and immobilized with synthetic templates.

Unfolding and Cleavage Reactions

After incubation at 37° C. for 60 min, the unbound probes were removed by washes. The cleavage and unfolding reactions were carried out as described in Example 5, wherein additional cleavage strands were not included in the assay using the continuous two part probe.

FIG. 25A shows the signal obtained from the two-part cleavage strand probe using target DNA immobilized via a biotin/streptavidin interaction. FIG. 25B shows the signal obtained from target DNA hybridised to a glass slide and demonstrates that the continuous two-part probe generates a similar signal to the two-part probe comprising cleavage strands in the presence of the target analyte. Both probes shows a low signal in the absence of target DNA. The continuous the two-part probe shows a better signal to noise ratio than the cleavage strand two-part probe.

Example 7

Five-part Hairpin Probe

A five-part hairpin probe (as shown in FIG. 18B) was used to detect DNA immobilized to a glass slide.

Steps for the immobilization of a synthetic DNA target, preparation and hybridization of the probes, and the cleavage and detection steps were performed following the protocols described in Examples 5 and 6.

Similarly to Example 6, the probes were ordered in parts: the RCA primer domain, first part of the RCA template (padlock 1), second part of the RCA template (padlock 2) and two ligation template domains (ligation 1 and 2) along with their connection templates. The RCA primer part was biotinylated at its 5' end. The five part probes were assembled by first immobilizing the RCA primer part oligonucleotides on streptavidin coated beads (MyOne T1 beads, Invitrogen). Approximately ⅛ coating positions per bead were occupied by the RCA primer part oligonucleotides. The other four parts (padlock 1, padlock 2, ligation 1 and ligation 2) were sequentially added to the RCA primer part oligonucleotides by an iterating protocol with addition of ligation mix containing a two fold molar excess of probe parts and a 20 fold molar excess of connection templates in 1×ligation buffer (400 mM Tris-HCl, 100 mM $MgCl_2$), 0.1 u/µl T4 DNA ligase (Fermantas) and 0.5 mM ATP, incubating at 37° C. for 30 min. Before every addition of a new mix, a washing step was applied to the beads, comprising incubation in 1×PBS 0.05% Tween-20 at room temperature and 0.1×SSC at 46° C. for 30 min. After the last ligation reaction, the DNA ligation products were released from the beads by incubating the beads with 95% formamide at 90° C. for 5 min. Supernatants were applied to a 6% TBE-Urea gel (Life Technologies) according to manufacture's manual. The five-part probes were then recovered by purifying DNA fragments at an approximate size of 500 bp from the gel.

FIG. 18C shows that RCA products could be detected using a five part probe. Two "blobs" are seen for each RCA product as each ligation domain acts as a reporter domain, meaning that the RCA product was dual labelled.

TABLE 1

| Oligonucleotide name | 5' modification | 3' modification | Purification | Sequence (5'-3') |
|---|---|---|---|---|
| Example 1 | | | | |
| 1 RCA primer | Biotin | — | PAGE | AAA AAA AAA ATA TGA CAG AAC TAG ACA CTC TT (SEQ ID NO: 1) |
| 1 RCA padlock | Phosphate | - | Standard | GTT CTG TCA TAC AGT GAA TGC GAG TCC GTC TAA GAG AGT AGT ACA GCA GCC GTC AAG AGT GTC TA (SEQ ID NO: 2) |
| 1 Detection oligo | FITC | — | HPLC | AAA AAA CAG TGA ATG CGA GTC CGT CT (SEQ ID NO: 3) |
| 2 RCA primer (probe) | — | — | HPLC | AAG AGA GTA GTA CAG CAG CCG TCA AGA GTG TCT AmAmA mAAA TCG GGC GAC ATA AGC AGA TAC GC (SEQ ID NO: 4) |
| 2 RCA padlock | Phosphate | — | Standard | ATG TCG CCC GAT ATC ACT GCC CCG ACA GGC TCA GA CAT CAT AAT AGC GCG TAT CTG CTT (SEQ ID NO: 5) |
| 2 Detection oligo | Cy3 | — | HPLC | GTA TCT GCT TAT GTC GCC CG (SEQ ID NO: 6) |
| Example 7 | | | — | |
| Target | 5' Biotin | 3' RNA Ome | Standard | TCTCTCTCTCTGCTGCTTCGTTGTGGAAGTCTCGGTTTTCCGCG AAGCTTTCGTTGGTGGCGAACTCGTTTGCGGTTCTGAATTCCTT GTTTCCCCTGAAUUU (SEQ ID NO: 7) |
| RCA primer part | 5' Biotin | — | Standard | AGTGAGCTAGACAGGGGAAACAAGGAAGAACGACGAACGTGATA CGAGTCAAAAA (SEQ ID NO: 8) |
| Connection template 1 | — | — | Standard | GGCAAAGCGGUUUUUGACUC (SEQ ID NO: 9) |

TABLE 1-continued

| Oligonucleotide name | 5' modification | 3' modification | Purification | Sequence (5'-3') |
|---|---|---|---|---|
| Padlock 1 | — | — | Standard | CCGCTTTGCCTGTCTGAACGTGCTTGTTTCCGTGCAGTGGCCAGTATCACGTTCGTCGTGTGCGACTTTCTCATGTTGTGCGTTTGGCCACTGCACGGAAACAAGCACGGAAAGAACCGCAAACGAGGAGTCAAAAA (SEQ ID NO: 10) |
| Connection template 2 | — | — | Standard | CAAGCGGACCUUUUUGACUC (SEQ ID NO: 11) |
| Padlock 2 | — | — | Standard | GGTCCGCTTGTCTTGGAAGCCTTTGCTTCGTCTGCAGTGGACAAACACCGTCCATACGCCTGCTTGTCGTGTCCACTGCAGACGAAGCAAAGGCGAAGCCACCAACGAAAGCGAGTCAAAAA (SEQ ID NO: 12) |
| Cleavage strand 1 | — | — | Standard | CCUGCUUGUCGUGUCCCGCUUUGCCUGUCUUUUUGACUC (SEQ ID NO: 13) |
| Ligation 1 | — | — | Standard | AGACAGGCAAAGCGGGACACGACAAGCAGGGAAGCGGAAAACCGAGACGAGTCAAAAA (SEQ ID NO: 14) |
| Cleavage strand 2 | — | — | Standard | UGUUGUGCGUUUGGCGGUCCGCUUGUCUUGUUUUUGACUC (SEQ ID NO: 15) |
| Ligation 2 | — | — | Standard | CAAGACAAGCGGACCGCCAAACGCACAACAGAACACAACGAAGCAGCAGAGTCAAAAA (SEQ ID NO: 16) |
| Cleavage strand 3 | — | — | Standard | UUUUUGACUCCGACGAACGUGAUAC (SEQ ID NO: 17) |
| Detection oligo 1 | 5' Cy3 | — | HPLC | TGCGTTTGGCGGTCCGCTTG (SEQ ID NO: 18) |
| Detection oligo 2 | 5' Cy5 | — | HPLC | TTGTCGTGTCCCGCTTTGCC (SEQ ID NO: 19) |
| Two part RCA probes | | | | |
| Target | 5' Biotin | — | HPLC | AAAAAAAAAACGCGTCCGCCCCGCGAAAGCCTCGCCTTTGCCGAAACCGCGCTCGTCGTCG (SEQ ID NO: 20) |
| Continuous RCA two part probe part 1 | — | — | Standard | CGACGACGAGCGCGGAAAAGACAGGCAAAGCGGAGGGGAAACAAGGAAAAAUUCCUUGUUUCCCCUCCGCUUUGCCUGUCUGAAGCGGTTTTTGACTCGAGACGAAGTCTCGAGTCAAAAACCGCTTTGCCTGTCTCGTGCTTG (SEQ ID NO: 21) |
| Continuous RCA probe two part probe part 2 | — | 3' Biotin | HPLC | TGCAGTGAGGGCTCGTTTGCGGTTCTAAATTCCTTGTTTCCCCTCACTGCACAAGCACGAAACGCGGGGCGGACGCGAGTGAGCTAGAC (SEQ ID NO: 22) |
| Cleavage strand RCA probe RCA template strand | — | — | PAGE | CGACGACGAGCGCGGAAAAGACAGGCAAAGCGGAGGGGAAACAAGGAAGAGTCAAAAACCGCTTTGCCTGTCTCGTGCTTGTGCAGTGAGGGCTCGTTTGCGGTTCTGAATTCCTTGTTTCCCCTCACTGCACAAGCACGGAACGCGGGGCGGACGCG (SEQ ID NO: 23) |
| Cleavage strand | — | — | Standard | UUUUUGACUCUUCCUUGUUUCCCCUCCGCUUUGCCUGUCU (SEQ ID NO: 24) |
| Two part linear RCA template strand | — | — | | TCTCTCTCTCAAGAGTGTCTAGTTCTGTCATAGAAAGACAGGCAAGCGGAGGGGAAACAAGGAAGAGTCAAAAACCGCTTTGCCTGTCTATTGCTTGTGCAGTGAGGGCTCGTTTGCGGTTCTGAATTCCTTGTTTCCCCTCACTGCACAAGCAATGAAAAGCGTCTTAACTATTAGCGTC (SEQ ID NO: 25) |
| Cleavage strand | — | — | | UUUUUGACUCUUCCUUGUUUCCCCUCCGCUUUGCCUGUCU (SEQ ID NO: 24) |
| Two-part RCA template strand | 5' phosphorylation | — | PAGE | CGACGACGAGCGCGGAAAAGACAGGCAAAGCGGAGGGGAAACAAGGAAGAGTCAAAAACCGCTTTGCCTGTCTCGTGCTTGTGCAGTGAGGGCTCGTTTGCGGTTCTGAATTCCTTGTTTCCCCTCACTGCACAAGCACGGAACGCGGGGCGGACGCG (SEQ ID NO: 26) |

TABLE 1-continued

| Oligonucleotide name | 5' modification | 3' modification | Purification | Sequence (5'-3') |
| --- | --- | --- | --- | --- |
| Detection oligonucleotide | 5'Cy3 | | HPLC | TTCCTTGTTTCCCCTCCGCTTTGCCTGTCT (SEQ ID NO: 27) |
| Cleavage strand | — | | Standard | UUUUUGACUCUUCCUUGUUUCCCCUCCGCUUUGCCUGUCU (SEQ IDNO: 24) |

The invention claimed is:

1. A method for performing a localised RCA reaction comprising at least two rounds of RCA, wherein the product of a second RCA reaction is attached, and hence localised, to a product of a first RCA reaction, said method comprising:
   (a) providing a first RCA product comprising tandem repeat units, wherein each repeat unit is a complementary copy of a template circle of a first RCA reaction;
   (b) directly or indirectly hybridising to multiple repeat units of said first RCA product first probes which comprise or provide a RCA primer for a second RCA reaction; and
   (c) performing a second RCA reaction using said RCA primer to form a second RCA product, wherein in said reaction:
   (i) said first probes and said RCA primer are not able to prime extension using said first RCA product as template, or said first probes and said RCA primer are able to prime extension but said extension is unable to displace first probes which are hybridised to the first RCA product,
   wherein:
   if a said first probe comprises or releases a 3' end which is not hybridised to the first RCA product, said first probe comprises one or more modified regions between the 3' end of the probe or primer and a region of the first probe which is hybridised to the first RCA product which act to inhibit 3' exonuclease degradation, or
   if a said first probe comprises a 3' end which hybridises to the first RCA product and the 3' end is not required for ligation, said first probe comprises a modification at or near its 3' end which acts to inhibit extension, or if a said first probe comprises a 3' end which hybridises to the first RCA product and is required for ligation, said first probe is modified at or near a hybridised ligatable 5' end to include a displacement block,
   and/or blocking oligonucleotides are used which hybridise to the first RCA product to avoid displacement of any probe hybridised to the first RCA product;
   (ii) the direct or indirect hybridisation of the RCA primer to the first RCA product is maintained and, by virtue of said hybridisation, the second RCA product is attached to the first RCA product; and
   (iii) a RCA template for said second RCA reaction is comprised in or provided by each of said first probes, or is provided separately from each of said first probes.

2. The method of claim 1, wherein said first probes hybridise to a probe-binding site present in monomers of the first RCA product or to an intermediate nucleic acid molecule hybridised to a complementary sequence present in a monomer of the first RCA product.

3. The method of claim 1, wherein step (a) comprises generating the first RCA product.

4. The method claim 1, wherein steps (a), (b) and (c) are performed simultaneously.

5. The method of claim 1, wherein steps (a), (b) and (c) are repeated one or more times.

6. The method of claim 1, wherein each of said first probes comprises:

(i) at least one binding domain comprising a region of complementarity to a target nucleic acid molecule, which is the first RCA product or an intermediate molecule hybridised, directly or indirectly, to the first RCA product;

(ii) a primer domain comprising or capable of providing the RCA primer; and (iii) at least one RCA-template complementary domain comprising a region of complementarity to a circular or circularisable template for said second RCA reaction; and optionally (iv) at least one ligation-template domain comprising or capable of providing a ligation template for circularisation of a circularisable template for the second RCA; and/or (v) at least one RCA template domain comprising or capable of providing a circular or circularisable template for the second RCA reaction;

wherein the domains are separate or overlapping.

7. The method of claim 1, wherein each of said first probes comprises one or more constituent nucleic acid strands, and one or more double-stranded regions, which may be formed by intra-molecular hybridisation or by inter-molecular hybridisation of separate nucleic acid strands.

8. The method of claim 6, wherein each of said first probes is or comprises a linear oligonucleotide, and wherein two binding domains are provided at each of the 3' and 5' ends of the oligonucleotide and first probes are hybridised to the first RCA product such that the ends of a said first probe are juxtaposed for ligation, directly or indirectly, to each other, the method further comprising ligating the probe ends, directly or indirectly, to each other.

9. The method of claim 1, wherein the RCA primer is unable to prime a second RCA reaction unless a first probe has hybridised directly or indirectly to the first RCA product.

10. The method of claim 1, wherein said first RCA product is immobilised on a solid support; and said method comprises an additional step of washing to remove any unbound first probes before performing the second RCA reaction of step (c).

11. The method of claim 1, wherein said first probes are cleaved and/or unfolded to release said RCA primer.

12. The method of claim 11, wherein said cleavage and/or unfolding is dependent upon hybridisation of a said first probe, directly or indirectly, to the first RCA product.

13. The method of claim 11, wherein
(i) each of said first probes comprises a hairpin structure which upon said hybridisation is unfolded to release a primer domain capable of functioning as the RCA primer; or
(ii) upon hybridisation of a said first probe to the first RCA product, a cleavage recognition site is created, and the first probe is cleaved to release the RCA primer; or
(iii) each of said first probes comprises a cleavage recognition site, and a first probe is cleaved to release the RCA primer.

14. The method of claim 1, wherein a circular or circularisable second RCA template is provided separately from each of said first probes.

15. The method of claim 14, wherein a circular second RCA template is provided separately from each of said first probes.

16. The method of claim 1, comprising:
(a) providing the first RCA product immobilised on a solid support;

(b) directly or indirectly hybridising to multiple repeat units of said first RCA second probes, a said second probe optionally being hybridised in juxtaposition for ligation directly or indirectly to a first probe, wherein said first and second probes each comprise at least one binding site complementary to a cognate binding site in one or more RCA template oligonucleotides, which oligonucleotides are ligatable together to form a circular RCA template for the second RCA reaction;

(c) hybridising to a said first probe and a said second probe the said one or more RCA template oligonucleotides, wherein said oligonucleotides are hybridised in juxtaposition for ligation to circularise the oligonucleotides;

(d) performing a ligation step to ligate together and circularise said RCA template oligonucleotides thereby generating a circular RCA template for the second RCA reaction, and optionally ligating together said first and second hybridised probes;

(e) washing one or more times to remove unbound probes and/or unligated probes, wherein to remove unbound probes said washing step may be performed before or after step (c) and to remove any unbound and unligated or any unligated probes, washing may be performed after step (d); and (f) performing said second RCA reaction using said circular RCA template.

17. The method of claim 1, wherein each of said first probes is a RCA reporter probe, which comprises or provides all the nucleic acid components for an RCA reaction as follows:
(i) the RCA primer for a second RCA reaction;
(ii) a circular or circularisable RCA template for the second RCA reaction; and
where said RCA template is circularisable,
(iii) a ligation template for circularisation of said RCA template;
wherein said first probes are cleavable and/or unfoldable to release at least the RCA primer to enable the second RCA reaction to be performed; and
wherein the method further comprises:
cleaving and/or unfolding the first probes to release the RCA primer, and optionally the RCA template, and the ligation template if present; and
where said RCA template is circularisable, performing a ligation step to circularise the RCA template prior to performing said second RCA reaction using said RCA primer and said RCA template.

18. The method of claim 8, wherein first probes that have hybridised to the first RCA product but have not been ligated are removed by stringent washing.

19. The method of claim 17, wherein the RCA primer and ligation template are provided by the same part of a first probe.

20. The method of claim 1, wherein a preformed circular nucleic acid molecule able to function as an RCA template for the second RCA reaction is provided as part of each of said first probes.

21. The method of claim 1, wherein each of said first probes comprises one or more hairpin and/or linear double-stranded structures comprising a cleavage recognition site, which are cleaved to release the RCA primer, a circularisable RCA template and ligation template.

22. The method of claim 1, wherein said blocking oligonucleotides are hybridised to the first RCA template in between first probes.

23. The method of claim 1, wherein said modified region comprises nuclease-resistant nucleotide residues, 2'O-Me-RNA residues, Locked Nucleic Acid (LNA) residues, Peptide Nucleic Acid (PNA) residues, phosphothiate-modified nucleic acids, a polyethylene-linker backbone moiety incorporated in between nucleotide residues, modified nucleotide residues which form more stable hybrids with DNA and/or RNA than unmodified residues, an abasic site, an intercalating group, and/or a hairpin structure.

24. The method of claim 1, wherein exonuclease-deficient and/or exonuclease-free reagents are used.

25. The method of claim 1, further comprising detecting a said attached second RCA product.

26. A method for detecting an analyte in a sample, comprising performing the method of claim 1, wherein
in step (a), the first RCA product is provided by performing a first RCA reaction using a first circular RCA template to generate the first RCA product, wherein the first circular RCA template is generated from a nucleic acid analyte, or is used or generated as a marker for said analyte, and wherein the method further comprises detecting said second RCA product, and optionally said first RCA product, thereby to detect said analyte.

27. The method of claim 26, wherein the first RCA product is generated by an immunoRCA or proximity probe assay.

28. The method of claim 26, for detecting more than one analyte in a sample, wherein the second RCA template for each analyte comprises a different reporter domain for detection of the second RCA product, or said analytes are detected sequentially.

29. The method of claim 26, wherein the second RCA product is detected using a labelled detection oligonucleotide which hybridises specifically to the second RCA product, by using a nucleic acid stain or by using labelled nucleotides for incorporation into the second RCA product, and optionally, the first RCA product is also detected using a labelled detection oligonucleotide which hybridises specifically to the first RCA product, by using a nucleic acid stain or by using labelled nucleotides for incorporation into the first RCA product.

30. The method claim 26, wherein the second RCA product is detected using liquid chromatography, electrophoresis, mass spectrometry, microscopy, real-time PCR, fluorescent probes, microarray, colorimetric analysis, flow cytometry, or CyTOF.

31. The method claim 1, wherein steps (a), (b) and (c) are performed sequentially.

32. The method of claim 14, wherein said RCA template is a circularisable template which is circularised by direct or indirect ligation of its ends using a ligation template comprised in or provided by a said first probe.

33. The method claim 26, wherein the second RCA product is detected by a turbidometric, magnetic, particle counting, electric, surface sensing, or weight-based detection technique.

* * * * *

SEQUENCE LISTING

<160> NUMBER OF SEQ ID NOS: 27

<210> SEQ ID NO 1
<211> LENGTH: 32
<212> TYPE: DNA
<213> ORGANISM: Artificial sequence
<220> FEATURE:
<223> OTHER INFORMATION: 1 RCA primer
<220> FEATURE:
<221> NAME/KEY: modified_base
<222> LOCATION: (1)..(1)
<223> OTHER INFORMATION: 5' Biotin

<400> SEQUENCE: 1
aaaaaaaaaa tatgacagaa ctagacactc tt         32

<210> SEQ ID NO 2
<211> LENGTH: 65
<212> TYPE: DNA
<213> ORGANISM: Artificial sequence
<220> FEATURE:
<223> OTHER INFORMATION: 1 RCA padlock
<220> FEATURE:
<221> NAME/KEY: modified_base
<222> LOCATION: (1)..(1)
<223> OTHER INFORMATION: 5' Phosphate

<400> SEQUENCE: 2
gttctgtcat acagtgaatg cgagtccgtc taagagagta gtacagcagc cgtcaagagt         60
gtcta         65

<210> SEQ ID NO 3
<211> LENGTH: 26
<212> TYPE: DNA
<213> ORGANISM: Artificial sequence
<220> FEATURE:
<223> OTHER INFORMATION: 1 Detection oligo
<220> FEATURE:
<221> NAME/KEY: modified_base
<222> LOCATION: (1)..(1)
<223> OTHER INFORMATION: 5' FITC

<400> SEQUENCE: 3
aaaaaacagt gaatgcgagt ccgtct         26

<210> SEQ ID NO 4
<211> LENGTH: 62
<212> TYPE: DNA
<213> ORGANISM: Artificial sequence
<220> FEATURE:
<223> OTHER INFORMATION: 2 RCA primer (probe)
<220> FEATURE:
<221> NAME/KEY: modified_base
<222> LOCATION: (35)..(37)
<223> OTHER INFORMATION: m2a

```
<400> SEQUENCE: 4
aagagagtag tacagcagcc gtcaagagtg tctaaaaaat cgggcgacat aagcagatac     60
gc                                                                   62

<210> SEQ ID NO 5
<211> LENGTH: 60
<212> TYPE: DNA
<213> ORGANISM: Artificial sequence
<220> FEATURE:
<223> OTHER INFORMATION: 2 RCA padlock
<220> FEATURE:
<221> NAME/KEY: modified_base
<222> LOCATION: (1)..(1)
<223> OTHER INFORMATION: 5' Phosphate

<400> SEQUENCE: 5
atgtcgcccg atatcactgc cccgacaggc ctcagacatc ataatagcgc gtatctgctt     60

<210> SEQ ID NO 6
<211> LENGTH: 20
<212> TYPE: DNA
<213> ORGANISM: Artificial sequence
<220> FEATURE:
<223> OTHER INFORMATION: 2 Detection oligo
<220> FEATURE:
<221> NAME/KEY: modified_base
<222> LOCATION: (1)..(1)
<223> OTHER INFORMATION: 5' Cy3

<400> SEQUENCE: 6
gtatctgctt atgtcgcccg                                                 20

<210> SEQ ID NO 7
<211> LENGTH: 103
<212> TYPE: DNA
<213> ORGANISM: Artificial sequence
<220> FEATURE:
<223> OTHER INFORMATION: Target
<220> FEATURE:
<221> NAME/KEY: modified_base
<222> LOCATION: (1)..(1)
<223> OTHER INFORMATION: 5' Biotin
<220> FEATURE:
<221> NAME/KEY: modified_base
<222> LOCATION: (103)..(103)
<223> OTHER INFORMATION: 3' RNA Ome

<400> SEQUENCE: 7
tctctctctc tgctgcttcg ttgtggaagt ctcggttttc cgcgaagctt tcgttggtgg     60
cgaactcgtt tgcggttctg aattccttgt ttcccctgaa uuu                     103

<210> SEQ ID NO 8
<211> LENGTH: 55
<212> TYPE: DNA
<213> ORGANISM: Artificial sequence
<220> FEATURE:
<223> OTHER INFORMATION: RCA primer part
<220> FEATURE:
<221> NAME/KEY: modified_base
<222> LOCATION: (1)..(1)
<223> OTHER INFORMATION: 5' Biotin

<400> SEQUENCE: 8
agtgagctag acaggggaaa caaggaagaa cgacgaacgt gatacgagtc aaaaa          55

<210> SEQ ID NO 9
<211> LENGTH: 20
```

```
<212> TYPE: DNA
<213> ORGANISM: Artificial sequence
<220> FEATURE:
<223> OTHER INFORMATION: Connection template 1

<400> SEQUENCE: 9
ggcaaagcgg uuuuugacuc                                              20

<210> SEQ ID NO 10
<211> LENGTH: 137
<212> TYPE: DNA
<213> ORGANISM: Artificial sequence
<220> FEATURE:
<223> OTHER INFORMATION: Padlock 1

<400> SEQUENCE: 10
ccgctttgcc tgtctgaacg tgcttgtttc cgtgcagtgg ccagtatcac gttcgtcgtg   60
tgcgactttc tcatgttgtg cgtttggcca ctgcacggaa acaagcacgg aaagaaccgc  120
aaacgaggag tcaaaaa                                                 137

<210> SEQ ID NO 11
<211> LENGTH: 20
<212> TYPE: DNA
<213> ORGANISM: Artificial sequence
<220> FEATURE:
<223> OTHER INFORMATION: Connection template 2

<400> SEQUENCE: 11
caagcggacc uuuuugacuc                                              20

<210> SEQ ID NO 12
<211> LENGTH: 122
<212> TYPE: DNA
<213> ORGANISM: Artificial sequence
<220> FEATURE:
<223> OTHER INFORMATION: Padlock 2

<400> SEQUENCE: 12
ggtccgcttg tcttggaagc ctttgcttcg tctgcagtgg acaaacaccg tccatacgcc   60
tgcttgtcgt gtccactgca gacgaagcaa aggcgaagcc accaacgaaa gcgagtcaaa  120
aa                                                                 122

<210> SEQ ID NO 13
<211> LENGTH: 40
<212> TYPE: DNA
<213> ORGANISM: Artificial sequence
<220> FEATURE:
<223> OTHER INFORMATION: Cleavage strand 1

<400> SEQUENCE: 13
ccugcuuguc gugcccgcu uugccugucu uuuuugacuc                         40

<210> SEQ ID NO 14
<211> LENGTH: 58
<212> TYPE: DNA
<213> ORGANISM: Artificial sequence
<220> FEATURE:
<223> OTHER INFORMATION: Ligation 1

<400> SEQUENCE: 14
agacaggcaa agcgggacac gacaagcagg gaagcggaaa accgagacga gtcaaaaa    58

<210> SEQ ID NO 15
```

```
<211> LENGTH: 40
<212> TYPE: DNA
<213> ORGANISM: Artificial sequence
<220> FEATURE:
<223> OTHER INFORMATION: Cleavage strand 2

<400> SEQUENCE: 15
uguugugcgu uuggcggucc gcuugucuug uuuuugacuc                           40

<210> SEQ ID NO 16
<211> LENGTH: 58
<212> TYPE: DNA
<213> ORGANISM: Artificial sequence
<220> FEATURE:
<223> OTHER INFORMATION: Ligation 2

<400> SEQUENCE: 16
caagacaagc ggaccgccaa acgcacaaca gaacacaacg aagcagcaga gtcaaaaa       58

<210> SEQ ID NO 17
<211> LENGTH: 25
<212> TYPE: DNA
<213> ORGANISM: Artificial sequence
<220> FEATURE:
<223> OTHER INFORMATION: Cleavage strand 3

<400> SEQUENCE: 17
uuuuugacuc cgacgaacgu gauac                                           25

<210> SEQ ID NO 18
<211> LENGTH: 20
<212> TYPE: DNA
<213> ORGANISM: Artificial sequence
<220> FEATURE:
<223> OTHER INFORMATION: Detection oligo 1
<220> FEATURE:
<221> NAME/KEY: modified_base
<222> LOCATION: (1)..(1)
<223> OTHER INFORMATION: 5' Cy3

<400> SEQUENCE: 18
tgcgtttggc ggtccgcttg                                                 20

<210> SEQ ID NO 19
<211> LENGTH: 20
<212> TYPE: DNA
<213> ORGANISM: Artificial sequence
<220> FEATURE:
<223> OTHER INFORMATION: Detection oligo 2
<220> FEATURE:
<221> NAME/KEY: modified_base
<222> LOCATION: (1)..(1)
<223> OTHER INFORMATION: 5' Cy5

<400> SEQUENCE: 19
ttgtcgtgtc ccgctttgcc                                                 20

<210> SEQ ID NO 20
<211> LENGTH: 61
<212> TYPE: DNA
<213> ORGANISM: Artificial sequence
<220> FEATURE:
<223> OTHER INFORMATION: Target
<220> FEATURE:
<221> NAME/KEY: modified_base
<222> LOCATION: (1)..(1)
<223> OTHER INFORMATION: 5' Biotin

<400> SEQUENCE: 20
```

```
aaaaaaaaaa cgcgtccgcc ccgcgaaagc ctcgcctttg ccgaaaccgc gctcgtcgtc    60
g                                                                    61

<210> SEQ ID NO 21
<211> LENGTH: 144
<212> TYPE: DNA
<213> ORGANISM: Artificial sequence
<220> FEATURE:
<223> OTHER INFORMATION: Continuous RCA two part probe part 1

<400> SEQUENCE: 21
cgacgacgag cgcggaaaag acaggcaaag cggaggggaa acaaggaaaa auuccuuguu    60
uccccuccgc uuugccuguc ugaagcggtt tttgactcga gacgaagtct cgagtcaaaa   120
accgctttgc ctgtctcgtg cttg                                          144

<210> SEQ ID NO 22
<211> LENGTH: 89
<212> TYPE: DNA
<213> ORGANISM: Artificial sequence
<220> FEATURE:
<223> OTHER INFORMATION: Continuous RCA two part probe part 2
<220> FEATURE:
<221> NAME/KEY: modified_base
<222> LOCATION: (89)..(89)
<223> OTHER INFORMATION: 3' Biotin

<400> SEQUENCE: 22
tgcagtgagg gctcgtttgc ggttctaaat tccttgtttc ccctcactgc acaagcacga    60
aacgcggggc ggacgcgagt gagctagac                                     89

<210> SEQ ID NO 23
<211> LENGTH: 158
<212> TYPE: DNA
<213> ORGANISM: Artificial sequence
<220> FEATURE:
<223> OTHER INFORMATION: Cleavage strand RCA probe RCA template strand

<400> SEQUENCE: 23
cgacgacgag cgcggaaaag acaggcaaag cggaggggaa acaaggaaga gtcaaaaacc    60
gctttgcctg tctcgtgctt gtgcagtgag ggctcgtttg cggttctgaa ttccttgttt   120 ccctcactg cacaagcacg gaacgcgggg cggacgcg                            158

<210> SEQ ID NO 24
<211> LENGTH: 40
<212> TYPE: DNA
<213> ORGANISM: Artificial sequence
<220> FEATURE:
<223> OTHER INFORMATION: Cleavage strand

<400> SEQUENCE: 24
uuuuugactc uuccuuguuu ccccuccgcu uugccugucu                          40

<210> SEQ ID NO 25
<211> LENGTH: 182
<212> TYPE: DNA
<213> ORGANISM: Artificial sequence
<220> FEATURE:
<223> OTHER INFORMATION: Two part linear RCA template strand

<400> SEQUENCE: 25
tctctctctc aagagtgtct agttctgtca tagaaagaca ggcaaagcgg aggggaaaca    60
```

```
aggaagagtc aaaaaccgct tgcctgtct attgcttgtg cagtgagggc tcgtttgcgg    120
ttctgaattc cttgtttccc ctcactgcac aagcaatgaa aagcgtctta actattagcg    180
tc                                                                  182

<210> SEQ ID NO 26
<211> LENGTH: 158
<212> TYPE: DNA
<213> ORGANISM: Artificial sequence
<220> FEATURE:
<223> OTHER INFORMATION: Two part RCA template strand
<220> FEATURE:
<221> NAME/KEY: modified_base
<222> LOCATION: (1)..(1)
<223> OTHER INFORMATION: 5' Phosphate

<400> SEQUENCE: 26
cgacgacgag cgcggaaaag acaggcaaag cggaggggaa acaaggaaga gtcaaaaacc     60
gctttgcctg tctcgtgctt gtgcagtgag ggctcgtttg cggttctgaa ttccttgttt    120
cccctcactg cacaagcacg gaacgcgggg cggacgcg                            158

<210> SEQ ID NO 27
<211> LENGTH: 30
<212> TYPE: DNA
<213> ORGANISM: Artificial sequence
<220> FEATURE:
<223> OTHER INFORMATION: Detection oligonucleotide
<220> FEATURE:
<221> NAME/KEY: modified_base
<222> LOCATION: (1)..(1)
<223> OTHER INFORMATION: 5' Cy3

<400> SEQUENCE: 27
ttccttgttt cccctccgct tgcctgtct                                       30
```